US012077576B2

(12) United States Patent
Shoemaker

(10) Patent No.: US 12,077,576 B2
(45) Date of Patent: Sep. 3, 2024

(54) **VHH POLYPEPTIDES THAT BIND TO *CLOSTRIDIUM DIFFICILE* TOXIN B AND METHODS OF USE THEREOF**

(71) Applicant: Trustees of Tufts College, Medford, MA (US)

(72) Inventor: Charles B. Shoemaker, Medford, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 18/013,195

(22) PCT Filed: Jun. 30, 2021

(86) PCT No.: PCT/US2021/039798
§ 371 (c)(1),
(2) Date: Dec. 27, 2022

(87) PCT Pub. No.: WO2022/006219
PCT Pub. Date: Jan. 6, 2022

(65) Prior Publication Data
US 2023/0192825 A1    Jun. 22, 2023

Related U.S. Application Data

(60) Provisional application No. 63/047,436, filed on Jul. 2, 2020.

(51) Int. Cl.
*C07K 16/12* (2006.01)
*A61P 31/04* (2006.01)
*C07K 14/47* (2006.01)
*A61K 39/00* (2006.01)

(52) U.S. Cl.
CPC .......... *C07K 16/1282* (2013.01); *A61P 31/04* (2018.01); *C07K 14/47* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 5,194,596 A | 3/1993 | Tischer et al. |
| 5,196,193 A | 3/1993 | Carroll |
| 5,225,539 A | 7/1993 | Winter |
| 5,455,030 A | 10/1995 | Ladner et al. |
| 5,530,101 A | 6/1996 | Queen et al. |
| 5,585,089 A | 12/1996 | Queen et al. |
| 5,624,659 A | 4/1997 | Bigner et al. |
| 5,693,761 A | 12/1997 | Queen et al. |
| 5,693,762 A | 12/1997 | Queen et al. |
| 5,731,168 A | 3/1998 | Carter et al. |
| 5,840,526 A | 11/1998 | Casterman et al. |
| 6,015,695 A | 1/2000 | Casterman et al. |
| 6,180,370 B1 | 1/2001 | Queen et al. |
| 6,187,287 B1 | 2/2001 | Leung et al. |
| 7,345,161 B2 | 3/2008 | Masuda et al. |
| 7,745,587 B2 | 6/2010 | Devy et al. |
| 7,763,445 B2 | 7/2010 | Moore et al. |
| 7,807,184 B2 | 10/2010 | Vermeij |
| 7,867,724 B2 | 1/2011 | Alexandru et al. |
| 7,879,333 B2 | 2/2011 | Gerber |
| 7,943,345 B2 | 5/2011 | Park et al. |
| 8,114,634 B2 | 2/2012 | Park et al. |
| 8,349,326 B2 | 1/2013 | Shoemaker et al. |
| 8,865,169 B2 | 10/2014 | Shoemaker et al. |
| 8,865,871 B2 | 10/2014 | Park et al. |
| 8,975,382 B2 | 3/2015 | Revets et al. |
| 9,023,352 B2 | 5/2015 | Shoemaker et al. |
| 9,834,616 B2 | 12/2017 | Shoemaker et al. |
| 10,131,870 B2 | 11/2018 | Takeuchi et al. |
| 10,202,441 B2 | 2/2019 | Shoemaker |
| 10,550,174 B2 | 2/2020 | Stortelers et al. |
| 10,766,950 B2 | 9/2020 | Shoemaker |
| 11,001,625 B2 | 5/2021 | Shoemaker |
| 11,091,563 B2 | 8/2021 | Shoemaker et al. |

(Continued)

FOREIGN PATENT DOCUMENTS

| | | |
|---|---|---|
| CN | 103866401 A | 6/2014 |
| EP | 0239400 A2 | 9/1987 |

(Continued)

OTHER PUBLICATIONS

Benton et al., "Screening λgt Recombinant Clones by Hybridization to Single Plaques in situ," Science, Apr. 8, 1977, vol. 196, pp. 180-182.
Brizzard et al., "Epitope Tagging of Recombinant Proteins," Current Protocols in Neuroscience, 1997, pp. 5.8.1-5.8.10.
Chen et al., "A Mouse Model of Clostridium difficile-Associated Disease," Gastroenterology, Dec. 2008, vol. 135, No. 6, pp. 1984-1992.
Cohen, Jon, "Naked DNA Points Way to Vaccines," Science, Mar. 19, 1993, vol. 259, pp. 1691-1692.

(Continued)

Primary Examiner — Meera Natarajan
Assistant Examiner — Cheom-Gil Cheong
(74) Attorney, Agent, or Firm — Melissa Hunter-Ensor; Leslie Serunian; Greenberg Traurig, LLP

(57) ABSTRACT

Polypeptide products, methods, pharmaceutical compositions, and kits are provided for treating a subject exposed to, or at risk for exposure to, *C. difficile* microbial pathogens and toxin B produced by *C. difficile* (TcdB) pathogens. The methods, compositions and kits include a single domain, anti-TedB VHH polypeptide (antibody), or toxin B binding portion thereof, that specifically binds to and/or neutralizes TedB and treats or prevents illness and disease associated with *C. difficile* infection and TedB intoxication. The anti-TcdB VHHs, or toxin B binding portion thereof, may be recombinantly produced.

17 Claims, 11 Drawing Sheets
Specification includes a Sequence Listing.

(56) References Cited

U.S. PATENT DOCUMENTS

| | | |
|---|---|---|
| 2004/0053340 A1 | 3/2004 | De Haard et al. |
| 2005/0287129 A1 | 12/2005 | Ciccarelli et al. |
| 2006/0018911 A1 | 1/2006 | Ault-Riche et al. |
| 2006/0149041 A1 | 7/2006 | Silence |
| 2009/0098608 A1 | 4/2009 | Park et al. |
| 2010/0092511 A1 | 4/2010 | Waldor et al. |
| 2010/0136018 A1 | 6/2010 | Dolk et al. |
| 2010/0278830 A1 | 11/2010 | Shoemaker et al. |
| 2011/0010782 A1 | 1/2011 | Horvitz et al. |
| 2011/0129474 A1 | 6/2011 | Shoemaker et al. |
| 2013/0058962 A1* | 3/2013 | Shoemaker ............. A61P 31/04 530/358 |
| 2014/0072581 A1 | 3/2014 | Dixit et al. |
| 2014/0294826 A1 | 10/2014 | Shoemaker |
| 2015/0093384 A1 | 4/2015 | Shoemaker et al. |
| 2016/0031971 A9 | 2/2016 | Shoemaker |
| 2016/0159866 A1 | 6/2016 | Ichtchenko et al. |
| 2016/0362501 A1 | 12/2016 | Shoemaker et al. |
| 2016/0368972 A1 | 12/2016 | Shoemaker |
| 2017/0204169 A1 | 7/2017 | Shoemaker et al. |
| 2017/0362310 A1 | 12/2017 | Shoemaker |
| 2019/0225675 A1 | 7/2019 | Shoemaker |
| 2020/0129444 A1 | 4/2020 | Whitehead et al. |
| 2021/0188953 A1 | 6/2021 | Shoemaker |
| 2021/0221874 A1 | 7/2021 | Shoemaker |
| 2021/0363275 A1 | 11/2021 | Shoemaker et al. |

FOREIGN PATENT DOCUMENTS

| | | |
|---|---|---|
| EP | 0519596 A1 | 12/1992 |
| EP | 0592106 A1 | 4/1994 |
| WO | 1991009967 A1 | 7/1991 |
| WO | 2009139919 A2 | 11/2009 |
| WO | 2011068953 A2 | 6/2011 |
| WO | 2015100409 A2 | 7/2015 |
| WO | 2016040499 A1 | 3/2016 |
| WO | 2019094095 A1 | 5/2019 |

OTHER PUBLICATIONS

Daeron, Marc, "Fc Receptor Biology," Annual Review of Immunology, Apr. 1997, vol. 15, pp. 203-234.

Davies et al., "Defective Fc-Dependent Processing of Immune Complexes in Patients With Systemic Lupus Erythematosus," Arthritis & Rheumatism, Apr. 2002, vol. 46, No. 4, pp. 1028-1038.

Einhauer et al., "The FLAG™ peptide, a versatile fusion tag for the purification of recombinant proteins, " Journal of Biochemical and Biophysical Methods, 2001, vol. 49, pp. 455-465.

Fritze et al., "Epitope tagging: General method for tracking recombinant proteins," Methods in Enzymology, 2000, vol. 327, pp. 3-16.

Gronbach et al., "Safety of Probiotic Escherichia coli Strain Nissle 1917 Depends on Intestinal Microbiota and Adaptive Immunity of the Host," Infection and Immunity, Jul. 2010, vol. 78, No. 7, pp. 3036-3046.

Grunstein et al., "Colony hybridization: a method for the isolation of cloned DNAs that contain a specific gene," Proceedings of the National Academy of Sciences of the United States of America, Oct. 1975, vol. 72, No. 10, pp. 3961-3965.

Hernan et al., "Multiple Epitope Tagging of Expressed Proteins for Enhanced Detection," BioTechniques, 2000, vol. 28, No. 4, pp. 789-793.

Johansson et al., "Liver cell uptake and degradation of soluble immunoglobulin G immune complexes in vivo and in vitro in rats," Hepatology, Jul. 1996, vol. 24, No. 1, pp. 169-175.

Kashmiri et al., "SDR grafting—a new approach to antibody humanization," Methods, 2005, vol. 36, pp. 25-34.

Killgore et al., "Comparison of Seven Techniques for Typing International Epidemic Strains of Clostridium difficile: Restriction Endonuclease Analysis, Pulsed-Field Gel Electrophoresis, PCR-Ribotyping, Multilocus Sequence Typing, Multilocus Variable-Number Tandem-Repeat Analysis, Amplified Fragment Length Polymorphism, and Surface Layer Protein A Gene Sequence Typing," Journal of Clinical Microbiology, Feb. 2008, vol. 46, No. 2, pp. 431-437.

Kimmel, Alan R., "[54] Identification and Characterization of Specific Clones: Strategy for Confirming the Validity of Presumptive Clones," Methods in Enzymology, 1987, vol. 152, pp. 507-511.

Lovdal et al., "Fc receptor mediated endocytosis of small soluble immunoglobulin G immune complexes in Kupffer and endothelial cells from rat liver," Journal of Cell Science, 2000, vol. 113, pp. 3255-3266.

Maass et al., "Alpaca (Lama pacos) as a convenient source of recombinant camelid heavy chain antibodies (VHHs)," Journal of Immunological Methods, Jul. 31, 2007, vol. 324, No. 1-2, pp. 13-25.

Maass et al., "Three surface antigens dominate the mucosal antibody response to gastrointestinal L3-stage strongylid hematodes in field immune sheep," International Journal for Parasitology, 2007, vol. 37, pp. 953-962.

Mitchell et al., "Comparative analysis of nanobody sequence and structure data," Proteins: Structure, Function, and Bioinformatics, 2018, vol. 86, pp. 697-706.

Moayeri et al., "Adenoviral Expression of a Bispecific VHH-Based Neutralizing Agent That Targets Protective Antigen Provides Prophylactic Protection from Anthrax in Mice," Clinical and Vaccine Immunology, Mar. 2016, vol. 23, No. 3, pp. 213-218.

Mohamed et al., "A High-Affinity Monoclonal Antibody to Anthrax Protective Antigen Passively Protects Rabbits before and after Aerosolized Bacillus anthracis Spore Challenge," Infection and Immunity, Feb. 2005, vol. 73, No. 2, pp. 795-802.

Mukherjee et al., "A Novel Strategy for Development of Recombinant Antitoxin Therapeutics Tested in a Mouse Botulism Model," PLoS One, Jan. 2012, vol. 7, No. 1, e29941, pp. 1-12.

Mukherjee et al., "Human Stx2-Specific Monoclonal Antibodies Prevent Systemic Complications of Escherichia coli O157:H7 Infection," Infection and Immunity, Feb. 2002, vol. 70, No. 2, pp. 612-619.

Mukherjee et al., "Prolonged Prophylactic Protection from Botulism with a Single Adenovirus Treatment Promoting Serum Expression of a VHH-Based Antitoxin Protein," PLoS One, Aug. 2014, vol. 9, No. 8, e106422, pp. 1-13.

Nowakowski et al., "Potent neutralization of botulinum neurotoxin by recombinant oligoclonal antibody," Proceedings of the National Academy of Sciences of the United States of America, Aug. 20, 2002, vol. 99, No. 17, pp. 11346-11350.

Patra et al., "Nano based drug delivery systems: recent developments and future prospects," Journal of Nanobiotechnology, 2018, vol. 16, Article No. 71, pp. 1-33.

Riechmann et al., "Reshaping human antibodies for therapy," Nature, Mar. 24, 1988, vol. 332, pp. 323-327.

Sepulveda et al., "Efficient Serum Clearance of Botulinum Neurotoxin Achieved Using a Pool of Small Antitoxin Binding Agents," Infection and Immunity, Feb. 2010, vol. 78, No. 2, pp. 756-763.

Sheoran et al., "Adenovirus Vector Expressing Stx1/Stx2-Neutralizing Agent Protects Piglets Infected with Escherichia coli O157:H7 against Fatal Systemic Intoxication," Infection and Immunity, Jan. 2015, vol. 83, No. 1, pp. 286-291.

Sponseller et al., "Hyperimmune Bovine Colostrum as a Novel Therapy to Combat Clostridium difficile Infection," The Journal of Infectious Diseases, Apr. 15, 2015, vol. 211, pp. 1334-1341.

Thran et al., "mRNA mediates passive vaccination against infectious agents, toxins, and tumors," EMBO Molecular Medicine, 2017, vol. 9, No. 10, pp. 1434-1447.

Tremblay et al., "A Single VHH-Based Toxin-Neutralizing Agent and an Effector Antibody Protect Mice against Challenge with Shiga Toxins 1 and 2," Infection and Immunity, Dec. 2013, vol. 81, No. 12, pp. 4592-4603.

Tremblay et al., "Camelid single domain antibodies (VHHs) as neuronal cell intrabody binding agents and inhibitors pf Clostridium botulinum neurotoxin (BoNT) proteases," Toxicon, Nov. 2010, vol. 56, No. 6, pp. 990-998.

Tzipori et al., "The Role of the eaeA Gene in Diarrhea and Neurological Complications in a Gnotobiotic Piglet Model of Enterohemorrhagic Escherichia coli Infection," Infection and Immunity, Sep. 1995, vol. 63, No. 9, pp. 3621-3627.

(56) References Cited

OTHER PUBLICATIONS

Ulmer et al., "Heterologous Protection Against Influenza by Injection of DNA Encoding a Viral Protein," Science, Mar. 19, 1993, vol. 259, pp. 1745-1749.
Vattekatte et al., "Discrete analysis of camelid variable domains: sequences, structures, and in-silico structure prediction," PeerJ, 2020, vol. 8, e8408, pp. 1-28.
Voth et al., "Clostridium difficile Toxins: Mechanism of Action and Role in Disease," Clinical Microbiology Reviews, Apr. 2005, vol. 18, No. 2, pp. 247-263.
Wahl et al., "[43] Molecular Hybridization of Immobilized Nucleic Acids: Theoretical Concepts and Practical Considerations," Methods in Enzymology, 1987, vol. 152, pp. 399-407.
Walker, K., "Interscience Conference on Antimicrobial Agents and Chemotherapy—50th Annual Meeting—Research on Promising New Agents: Part 1," Idrugs: The Investigational Drugs Journal, Nov. 2010, vol. 13, No. 11, pp. 743-745. [Abstract].
Yang et al., "A Novel Multivalent, Single-Domain Antibody Targeting TcdA and TcdB Prevents Fulminant Clostridium difficile Infection in Mice," The Journal of Infectious Diseases, Sep. 15, 2014, vol. 210, pp. 964-972.
International Search Report and Written Opinion mailed Dec. 20, 2021 in corresponding International PCT Patent Application No. PCT/US2021/039798 (14 pages).
Loo et al., "A Predominantly Clonal Multi-Institutional Outbreak of Clostridium difficile-Associated Diarrhea with High Morbidity and Mortality," The New England Journal of Medicine, Dec. 2005, vol. 353, No. 23, pp. 2442-2449.
Lowy et al., "Treatment with Monoclonal Antibodies against Clostridium difficile Toxins," The New England Journal of Medicine, Jan. 2010, vol. 362, No. 3, pp. 197-205.
Manglik et al., "Nanobodies to Study G Protein-Coupled Receptor Structure and Function," Annual Review of Pharmacology and Toxicology, 2017, vol. 57, pp. 19-37.
McCoy et al., "Phaser crystallographic software," Journal of Applied Crystallography, 2007, vol. 40, pp. 658-674.
McDonald et al., "An Epidemic, Toxin Gene-Variant Strain of Clostridium difficile," The New England Journal of Medicine, Dec. 2005, vol. 353, No. 23, pp. 2433-2441.
McNutt et al., "Neuronal delivery of antibodies has therapeutic effects in animal models of botulism," Science Translational Medicine, Jan. 6, 2021, vol. 13, eabd7789, pp. 1-12.
Miyashita et al., "Delivery of single-domain antibodies into neurons using a chimeric toxin-based platform is therapeutic in mouse models of botulism," Science Translational Medicine, Jan. 6, 2021, vol. 13, eaaz4197, pp. 1-12.
Mizanur et al., "The C Terminus of the Catalytic Domain of Type A Botulinum Neurotoxin May Facilitate Product Release from the Active Site," The Journal of Biological Chemistry, Aug. 16, 2013, vol. 288, No. 33, pp. 24223-24233.
Moayeri et al., "A Heterodimer of a VHH (Variable Domains of Camelid Heavy Chain-only) Antibody That Inhibits Anthrax Toxin Cell Binding Linked to a VHH Antibody That Blocks Oligomer Formation Is Highly Protective in an Anthrax Spore Challenge Model," The Journal of Biological Chemistry, Mar. 6, 2015, vol. 290, No. 10, pp. 6584-6595.
Moayeri et al., "Anthrax Protective Antigen Cleavage and Clearance from the Blood of Mice and Rats," Infection and Immunity, Nov. 2007, vol. 75, No. 11, pp. 5175-5184.
Moayeri et al., "Inflammasome Sensor Nlrp1b-Dependent Resistance to Anthrax Is Mediated by Caspase-1, IL-1 Signaling and Neutrophil Recruitment," PLoS Pathogens, Dec. 2010, vol. 6, No. 12, e1001222, pp. 1-9.
Nayak et al., "Safety and Pharmacokinetics of Xoma 3AB, a Novel Mixture of Three Monoclonal Antibodies against Botulinum Toxin A," Antimicrobial Agents and Chemotherapy, Sep. 2014, vol. 58, No. 9, pp. 5047-5053.
Nguyen et al., "The pharmacokinetics of an albumin-binding Fab (AB.Fab) can be modulated as a function of affinity for albumin," Protein Engineering, Design & Selection, 2006, vol. 19, No. 7, pp. 291-297.
Ohtsuka et al., "An Alternative Approach to Deoxyoligonucleotides as Hybridization Probes by Insertion of Deoxyinosine at Ambiguous Codon Positions," The Journal of Biological Chemistry, Mar. 10, 1985, vol. 260, No. 5, pp. 2605-2608.
Owens Jr. et al., "Antimicrobal-Associated Risk Factors for Clostridium difficile Infection," Clinical Infectious Diseases, 2008, vol. 46, Suppl. 1, pp. S19-31.
Pardon et al., "A general protocol for the generation of Nanobodies for structural biology," Nature Protocols, 2014, vol. 9, No. 3, pp. 674-693.
Park et al., "Generation and Application of New Rat Monoclonal Antibodies Against Synthetic FLAG and OLLAS Tags for Improved Immunodetection," Journal of Immunological Methods, Feb. 2008, vol. 331, Nos. 1-2, pp. 27-38.
Park et al., "Optimized Production and Purification of Bacillus anthracis Lethal Factor," Protein Expression and Purification, 2000, vol. 18, pp. 293-302.
Petsch et al., "Protective efficacy of in vitro synthesized, specific mRNA vaccines against influenza A virus infection," Nature Biotechnology, Dec. 2012, vol. 30, No. 12, pp. 1210-1216.
Pfeifer et al., "Cellular Uptake of Clostridium difficile Toxin B: Translocation of the N-terminal Catalytic Domain into the Cytosol of Eukaryotic Cells," The Journal of Biological Chemistry, Nov. 2003, vol. 278, No. 45, pp. 44535-44541.
Pomerantsev et al., "Genome Engineering in Bacillus anthracis Using Cre Recombinase," Infection and Immunity, Jan. 2006, vol. 74, No. 1, pp. 682-693.
Pothoulakis et al., "Microbes and Microbial Toxins: Paradigms for Microbial-Mucosal Interactions II. The integrated response of the intestine to Clostridium difficile toxins," American Journal of Physiology- Gastrointestinal and Liver Physiology, 2001, vol. 280, pp. G178-G183.
Qa'Dan et al., "pH-Induced Conformational Changes in Clostridium difficile Toxin B," Infection and Immunity, May 2000, vol. 68, No. 5, pp. 2470-2474.
Reineke et al., "Autocatalytic cleavage of Clostridium difficile toxin B," Nature, Mar. 2007, vol. 446, pp. 415-419.
Riegler et al., "Clostridium difficile Toxin B Is More Potent than Toxin A in Damaging Human Colonic Epithelium In Vitro," The Journal of Clinical Investigation, May 1995, vol. 95, pp. 2004-2011.
Riemer et al., "Matching of trastuzumab (Herceptin®) epitope mimics onto the surface of Her-2/neu—a new method of epitope definition," Molecular Immunology, 2005, vol. 42, pp. 1121-1124.
Rosovitz et al., "Alanine-scanning Mutations in Domain 4 of Anthrax Toxin Protective Antigen Reveal Residues Important for Binding to the Cellular Receptor and to a Neutralizing Monoclonal Antibody," The Journal of Biological Chemistry, Aug. 15, 2003, vol. 278, No. 33, pp. 30936-30944.
Rossolini et al., "Use of deoxyinosine-containing primers vs degenerate primers for polymerase chain reaction based on ambiguous sequence information," Molecular and Cellular Probes, 1994, vol. 8, pp. 91-98.
Rupnik et al., "Characterization of the cleavage site and function of resulting cleavage fragments after limited proteolysis of Clostridium difficile toxin B (TcdB) by host cells," Microbiology, 2005, vol. 151, pp. 199-208.
Sakurai et al., "Liver Abscess Caused by Clostridium difficile," Scandinavian Journal of Infectious Diseases, 2001, vol. 33, pp. 69-70.
Sandvig et al., "Entry of ricin and Shiga toxin into cells: molecular mechanisms and medical perspectives," The EMBO Journal, 2000, vol. 19, No. 22, pp. 5943-5950.
Savidge et al., "Clostridium difficile Toxin B Is an Inflammatory Enterotoxin in Human Intestine" Gastroenterology, Aug. 2003, vol. 125, No. 2, pp. 413-420.
Schmidt et al., "A Tetraspecific VHH-Based Neutralizing Antibody Modifies Disease Outcome in Three Animal Models of Clostridium difficile Infection," Clinical and Vaccine Immunology, Sep. 2016, vol. 23, No. 9, pp. 774-784.

(56) References Cited

OTHER PUBLICATIONS

Sehr et al., "Glucosylation and ADP Ribosylation of Rho Proteins: Effects on Nucleotide Binding, GTPase Activity, and Effector Coupling," Biochemistry, 1998, vol. 37, pp. 5296-5304.
Siemann et al., "Clostridium difficile-associated diseases: The clinical courses of 18 fatal cases" Intensive Care Medicine, 2000, vol. 26, pp. 416-421.
Sikorra et al., "Identification of the Amino Acid Residues Rendering TI-VAMP Insensitive toward Botulinum Neurotoxin B," Journal of Molecular Biology, 2006, vol. 357, pp. 574-582.
Sikorra et al., "Substrate Recognition Mechanism of VAMP/Synaptobrevin-cleaving Clostridial Neurotoxins," The Journal of Biological Chemistry, Jul. 25, 2008, vol. 283, No. 30, pp. 21145-21152.
Silvaggi et al., "Structures of Clostridium botulinum Neurotoxin Serotype A Light Chain Complexed with Small-Molecule Inhibitors Highlight Active-Site Flexibility," Chemistry & Biology, May 2007, vol. 14, pp. 533-542.
Simpson, "Identification of the Major Steps in Botulinum Toxin Action," Annual Review of Pharmacology and Toxicology, 2004, vol. 44, pp. 167-193.
Singh et al., "The Chymotrypsin-sensitive Site, FFD315, in Anthrax Toxin Protective Antigen Is Required for Translocation of Lethal Factor," The Journal of Biological Chemistry, Nov. 18, 1994, vol. 269, No. 46, pp. 29039-29046.
Skolnick et al., "From genes to protein structure and function: novel applications of computational approaches in the genomic era," Trends in Biotechnology, Jan. 2000, vol. 18, No. 1, pp. 34-39.
Snow et al., "Safety and Pharmacokinetics of a Four Monoclonal Antibody Combination against Botulinum C and D Neurotoxins," Antimicrobial Agents and Chemotherapy, Dec. 2019, vol. 63, No. 12, e01270-19, pp. 1-11.
Spears et al., "A comparison of enteropathogenic and enterohaemorrhagic *Escherichia coli* pathogenesis," FEMS Microbiology Letters, Feb. 2006, vol. 255, pp. 187-202.
Stancovski et al., "Mechanistic aspects of the opposing effects of monoclonal antibodies to the ERBB2 receptor on tumor growth," Proceedings of the National Academy of Sciences of the United States of America, Oct. 1991, vol. 88, pp. 8691-8695.
Thess et al., "Sequence-engineered mRNA Without Chemical Nucleoside Modifications Enables an Effective Protein Therapy in Large Animals," Molecular Therapy, Sep. 2015, vol. 23, No. 9, pp. 1456-1464.
Tomic et al., "Monoclonal Antibody Combinations Prevent Serotype A and Serotype B Inhalational Botulism in a Guinea Pig Model," Toxins, 2019, vol. 11, Article No. 208, pp. 1-15.
Tonegawa, "The genetic principle for generation of antibody diversity," The Nobel Assembly at the Karolinska Institute, 1987, retrieved from the Internet on Feb. 12, 2024, URL: <nobelprize.org/nobel_prizes/medicine/laureates/1987/press.html>.
Tonna et al., "Pathogenesis and treatment of Clostridium difficile infection," Postgraduate Medical Journal, Jun. 2005, vol. 81, pp. 367-369.
Tremblay et al., "Camelid single domain antibodies (VHHs) as neuronal cell intrabody binding agents and inhibitors of Clostridium botulinum neurotoxin (BoNT) proteases," Toxicon, 2010, vol. 56, pp. 990-998.
Tremblay et al., "Camelid VHH Antibodies that Neutralize Botulinum Neurotoxin Serotype E Intoxication or Protease Function," Toxins, 2020, vol. 12, Article No. 611, pp. 1-18.
Fernández-salas et al., "Plasma membrane localization signals in the light chain of botulinum neurotoxin," Proceedings of the National Academy of Sciences of the United States of America, Mar. 2, 2004, vol. 101, No. 9, pp. 3208-3213.
Florin et al., "Internalization of Clostridium difficile cytotoxin into cultured human lung fibroblasts," Biochimica et Biophysica Acta, 1983, vol. 763, pp. 383-392.
Florin et al., "Lysosomal involvement in cellular intoxication with Clostridium difficile toxin B," Microbial Pathogenesis, Aug. 1986, vol. 1, No. 4, pp. 373-385.

Frank et al., "Epidemic Profile of Shiga-Toxin-Producing *Escherichia coli* O104:H4 Outbreak in Germany," The New England Journal of Medicine, Nov. 2011, vol. 365, No. 19, pp. 1771-1780.
Friedman et al., "Bacteriophage lambda: alive and well and still doing its thing," Current Opinion in Microbiology, 2001, vol. 4, pp. 201-207.
Friedrich et al., "*Escherichia coli* Harboring Shiga Toxin 2 Gene Variants: Frequency and Association with Clinical Symptoms," The Journal of Infectious Diseases, Jan. 2002, vol. 185, pp. 74-84.
Garcia-Rodriguez et al., "A Three Monoclonal Antibody Combination Potently Neutralizes Multiple Botulinum Neurotoxin Serotype E Subtypes," Toxins, 2018, vol. 10, Article No. 105, pp. 1-16.
Gerding et al., "Treatment of Clostridium difficile Infection," Clinical Infectious Diseases, 2008, vol. 46, Suppl. 1, pp. S32-S42.
Gibbs, "Nanobodies," Scientific American, Aug. 2005, vol. 293, No. 2, pp. 79-83.
Giesemann et al., "Cholesterol-dependent Pore Formation of Clostridium difficile Toxin A," The Journal of Biological Chemistry, Apr. 2006, vol. 281, No. 16, pp. 10808-10815.
Gu et al., "Botulinum Neurotoxin Is Shielded by NTNHA in an Interlocked Complex," Science, Feb. 24, 2012, vol. 335, pp. 977-981.
Hamm et al., "Identification of Clostridium difficile toxin B cardiotoxicity using a zebrafish embryo model of intoxication," Proceedings of the National Academy of Sciences of the United States of America, Sep. 2006, vol. 103, No. 38, pp. 14176-14181.
He et al., "Antibody-Enhanced, Fc Gamma Receptor-Mediated Endocytosis of Clostridium difficile Toxin A," Infection and Immunity, Jun. 2009, vol. 77, No. 6, pp. 2294-2303.
Hedican et al., "Characteristics of O157 versus Non-O157 Shiga Toxin-Producing *Escherichia coli* Infections in Minnesota, 2000-2006," Clinical Infectious Diseases, Aug. 2009, vol. 49, pp. 358-364.
Henriques et al., "Cellular internalisation of Clostridium difficile toxin A," Microbial Pathogenesis, 1987, vol. 2, pp. 455-463.
Higgins et al., "CLUSTAL: a package for performing multiple sequence alignment on a microcomputer," Gene, 1988, vol. 73, pp. 237-244.
Hoerr et al., "In vivo application of RNA leads to induction of specific cytotoxic T lymphocytes and antibodies," European Journal of Immunology, 2000, vol. 30, pp. 1-7.
Hunt, "Shiga Toxin-Producing *Escherichia coli* (STEC)," Clinics in Laboratory Medicine, 2010, vol. 30, pp. 21-45.
Hussack et al., "Toxin-Specific Antibodies for the Treatment of Clostridium difficile: Current Status and Future Perspectives," Toxins, 2010, vol. 2, pp. 998-1018.
Jacob et al., "Clostridium difficile and acute respiratory distress syndrome," Heart & Lung, Jul.-Aug. 2004, vol. 33, No. 4, pp. 265-268.
Janeway et al., "The interaction of the antibody molecule with specification antigen," Immunobiology: The Immune System in Health and Disease, 2001, 5th edition, 5 pages.
Jank et al., "Structure and mode of action of clostridial glucosylating toxins: the ABCD model," Trends in Microbiology, 2008, vol. 16, No. 5, pp. 222-229.
Jaskiewicz et al., "Identification and characterization of a new 34 kDa MORN motif-containing sporozoite surface- exposed protein, Cp-P34, unique to Cryptosporidium," International Journal for Parasitology, 2021, vol. 51, pp. 761-775.
Jirikowski et al., "Reversal of Diabetes Insipidus in Brattleboro Rats: Intrahypothalamic Injection of Vasopressin mRNA," Science, Feb. 21, 1992, vol. 255, pp. 996-998.
Johnson et al., "Fatal Pseudomembranous Colitis Associated with a Variant Clostridium difficile Strain Not Detected by Toxin A Immunoassay," Annals of Internal Medicine, Sep. 2001, vol. 135, No. 6, pp. 434-438.
Jubala et al., "CD20 Expression in Normal Canine B Cells and in Canine non-Hodgkin Lymphoma," Veterinary Pathology, 2005, vol. 42, No. 4, pp. 468-476.
Just et al., "Glucosylation of Rho proteins by Clostridium difficile toxin B," Nature, Jun. 1995, vol. 375, pp. 500-503.
Kabsch, Wolfgang, "XDS," Acta Crystallographica Section D: Biological Crystallography, 2010, vol. 66, pp. 125-132.

(56) References Cited

OTHER PUBLICATIONS

Karikó et al., "Increased Erythropoiesis in Mice Injected With Submicrogram Quantities of Pseudouridine-containing mRNA Encoding Erythropoietin," Molecular Therapy, May 2012, vol. 20, No. 5, pp. 948-953.

Karlsson et al., "Microbial recognition of target-cell glycoconjugates," Current Opinion in Structural Biology, 1995, vol. 5, pp. 622-635.

Karmali et al., "The Association Between Idiopathic Hemolytic Uremic Syndrome and Infection by Verotoxin- Producing *Escherichia coli*" The Journal of Infectious Diseases, May 1985, vol. 151, No. 5, pp. 775-782.

Kawano et al., "Relationship between pathogenicity for humans and stx genotype in Shiga toxin-producing Escherichia coli serotype O157," European Journal of Clinical Microbiology & Infectious Diseases, 2008, vol. 27, pp. 227-232.

Kelly et al., "Clostridium difficile Infection," Annual Review of Medicine, 1998, vol. 49, pp. 375-390.

Kelly et al., "Neutrophil Recruitment in Clostridium difficile Toxin A Enteritis in the Rabbit," The Journal of Clinical Investigation, Mar. 1994, vol. 93, pp. 1257-1265.

Krautz-Peterson et al., "Intracellular Neutralization of Shiga Toxin 2 by an A Subunit-Specific Human Monoclonal Antibody," Infection and Immunity, May 2008, vol. 76, No. 5, pp. 1931-1939.

Kuijper et al., "Clostridium difficile: changing epidemiology and new treatment options," Current Opinion in Infectious Diseases, 2007, vol. 20, pp. 376-383.

Kumaran et al., "Interactions of a potent cyclic peptide inhibitor with the light chain of botulinum neurotoxin A: Insights from X-ray crystallography," Bioorganic & Medicinal Chemistry, 2015, vol. 23, pp. 7264-7273.

Kumaran et al., "Substrate Binding Mode and Its Implication on Drug Design for Botulinum Neurotoxin A," PLoS Pathogens, Sep. 2008, vol. 4, No. 9, e1000165, pp. 1-9.

Kuroda et al., "Shape complementarity and hydrogen bond preferences in protein-protein interfaces: implications for antibody modeling and protein-protein docking," Bioinformatics, 2016, vol. 32, No. 16, pp. 2451-2456.

Kyne et al. "Health Care Costs and Mortality Associated with Nosocomial Diarrhea Due to Clostridium difficile," Clinical Infectious Diseases, 2002, vol. 34, pp. 346-353.

Lacy et al., "Crystal structure of botulinum neurotoxin type A and implications for toxicity," Nature Structural Biology, Oct. 1998, vol. 5, No. 10, pp. 898-902.

Lam et al., "Probing the structure and function of the protease domain of botulinum neurotoxins using single-domain antibodies," PLoS Pathogens, 2022, vol. 18, No. 1, e1010169, pp. 1-25.

Lam et al., "Structural Insights into Rational Design of Single-Domain Antibody-Based Antitoxins against Botulinum Neurotoxins," Cell Reports, 2020, vol. 30, pp. 2526-2539.

Lam et al., "Two VHH Antibodies Neutralize Botulinum Neurotoxin E1 by Blocking Its Membrane Translocation in Host Cells," Toxins, 2020, vol. 12, Article No. 616, pp. 1-14.

Lauwereys et al., "Potent enzyme inhibitors derived from dromedary heavy-chain antibodies," The Embo Journal, 1998, vol. 17, No. 13, pp. 3512-3520.

Lawrence et al., "Shape Complementarity at Protein/Protein Interfaces," Journal of Molecular Biology, 1993, vol. 234, pp. 946-950.

Lederman et al., "A Single Amino Acid Substitution in a Common African Allele of the CD4 Molecule Ablates Binding of the Monoclonal Antibody, OKT4," Molecular Immunology, 1991, vol. 28, No. 11, pp. 1171-1181.

Li et al., "β-Endorphin omission analogs: Dissociation of immunoreactivity from other biological activities," Proceedings of the National Academy of Sciences of the United States of America, Jun. 1980, vol. 77, No. 6, pp. 3211-3214.

Libby et al., "Effects of the Two Toxins of Clostridium difficile in Antibiotic-Associated Cecitis in Hamsters," Infection and Immunity, May 1982, vol. 36, No. 2, pp. 822-829.

Little et al., "Production and Characterization of Monoclonal Antibodies to the Protective Antigen Component of Bacillus anthracis Toxin," Infection and Immunity, Jul. 1988, vol. 56, No. 7, pp. 1807-1813.

Abaza et al., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," Journal of Protein Chemistry, 1992, vol. 11, No. 5, pp. 433-444.

Adams et al., "PHENIX: a comprehensive Python-based system for macromolecular structure solution," Acta Crystallographica Section D: Biological Crystallography, 2010, vol. 66, pp. 213-221.

Adelman et al., "In Vitro Deletional Mutagenesis for Bacterial Production of the 20,000-Dalton Form of Human Pituitary Growth Hormone," DNA, 1983, vol. 2, No. 3, pp. 183-193.

Agarwal et al., "Mode of VAMP substrate recognition and inhibition of Clostridium botulinum neurotoxin F," Nature Structural & Molecular Biology, Jul. 2009, vol. 16, No. 7, pp. 789-794.

Ahmed et al., "Identification of Residues Surrounding the Active Site of Type A Botulinum Neurotoxin Important for Substrate Recognition and Catalytic Activity," The Protein Journal, 2008, vol. 27, pp. 151-162.

Altschul et al., "Basic Local Alignment Search Tool," Journal of Molecular Biology, 1990, vol. 215, pp. 403-410.

Altschul et al., "Gapped BLAST and PSI-BLAST: a new generation of protein database search programs," Nucleic Acids Research, 1997, vol. 25, No. 17, pp. 3389-3402.

Babcock et al., "Human Monoclonal Antibodies Directed against Toxins A and B Prevent Clostridium difficile- Induced Mortality in Hamsters," Infection and Immunity, Nov. 2006, vol. 74, No. 11, pp. 6339-6347.

Baldwin et al., "The C-terminus of botulinum neurotoxin type A light chain contributes to solubility, catalysis, and stability," Protein Expression and Purification, 2004, vol. 37, pp. 187-195.

Battye et al., "iMOSFLM: a new graphical interface for diffraction-image processing with MOSFLM," Acta Crystallographica Section D: Biological Crystallography, 2011, vol. 67, pp. 271-281.

Batzer et al., "Enhanced evolutionary PCR using oligonucleotides with inosine at the 3'-terminus," Nucleic Acids Research, 1991, vol. 19, No. 18, p. 5081.

Barbut et al., "Epidemiology of Recurrences or Reinfections of Clostridium difficile-Associated Diarrhea," Journal of Clinical Microbiology, Jun. 2000, vol. 38, No. 6, pp. 2386-2388.

Bartlett, "Antibiotic-Associated Diarrhea," The New England Journal of Medicine, Jan. 2002, vol. 346, No. 5, pp. 334-339.

Bilge et al., "Translocation of Ricin A-chain into Proteoliposomes Reconstituted from Golgi and Endoplasmic Reticulum," The Journal of Biological Chemistry, Oct. 1995, vol. 270, No. 40, pp. 23720-23725.

Borriello et al., "Clostridium difficile infections of the gut: the unanswered questions," Journal of Antimicrobial Chemotherapy, 1998, vol. 41, Suppl. C, pp. 67-69.

Boerlin et al., "Associations between Virulence Factors of Shiga Toxin-Producing *Escherichia coli* and Disease in Humans" Journal of Clinical Microbiology, Mar. 1999, vol. 37, No. 3, pp. 497-503.

Buck et al., "Fusion of an Fc chain to a VHH boosts the accumulation levels in *Arabidopsis* seeds," Plant Biotechnology Journal, 2013, vol. 11, pp. 1006-1016.

Breidenbach et al., "Substrate recognition strategy for botulinum neurotoxin serotype A," Nature, Dec. 16, 2004, vol. 432, pp. 925-929.

Brown et al., "Cloning and characterization of an extracellular Ca2+-sensing receptor from bovine parathyroid," Nature, Dec. 1993, vol. 366, pp. 575-580.

Brown et al., "Identification and Characterization of a Neutralizing Monoclonal Antibody Against Botulinum Neurotoxin, Serotype F, Following Vaccination With Active Toxin," Hybridoma, 1997, vol. 16, No. 5, pp. 447-456.

Brunger et al., "Botulinum Neurotoxin Heavy Chain Belt as an Intramolecular Chaperone for the Light Chain," PLoS Pathogens, Sep. 2007, vol. 3, No. 9, e113, pp. 1191-1194.

(56) References Cited

OTHER PUBLICATIONS

Brünger, Axel T., "Free R value: a novel statistical quantity for assessing the accuracy of crystal structures," Nature, Jan. 30, 1992, vol. 355, pp. 472-475.
Bucholz et al., "German Outbreak of *Escherichia coli* O104: H4 Associated with Sprouts," The New England Journal of Medicine, Nov. 2011, vol. 365, No. 19, pp. 1763-1770.
Butterworth et al., "Ricin and Ricinus communis agglutinin subunits are all derived from a single-size polypeptide precursor," European Journal of Biochemistry, 1983, vol. 137, pp. 57-65.
Chen et al., "Insights into the Different Catalytic Activities of Clostridium Neurotoxins," Biochemistry, 2012, vol. 51, pp. 3941-3947.
Chen et al., "Mechanism of Substrate Recognition by Botulinum Neurotoxin Serotype A," The Journal of Biological Chemistry, Mar. 30, 2007, vol. 282, No. 13, pp. 9621-9627.
Chen et al., "MolProbity: all-atom structure validation for macromolecular crystallography," Acta Crystallographica Section D: Biological Crystallography, 2010, vol. 66, pp. 12-21.
Chen et al., "Novel Chimpanzee/Human Monoclonal Antibodies That Neutralize Anthrax Lethal Factor, and Evidence for Possible Synergy with Anti-Protective Antigen Antibody," Infection and Immunity, Sep. 2009, vol. 77, No. 9, pp. 3902-3908.
Chen et al., "Substrate Recognition of VAMP-2 by Botulinum Neurotoxin B and Tetanus Neurotoxin," The Journal of Biological Chemistry, Jul. 25, 2008, vol. 283, No. 30, pp. 21153-21159.
Cherla et al., "Shiga toxins and apoptosis," FEMS Microbiology Letters, 2003, vol. 228, pp. 159-166.
Cogburn et al., "Growth, Metabolic and Endocrine Responses of Broiler Cockerels Given a Daily Subcutaneous Injection of Natural or Biosynthetic Chicken Growth Hormone," The Journal of Nutrition, 1989, vol. 119, pp. 1213-1222.
Cohen et al., "Roles of Globotriosyl- and Galabiosylceramide in Verotoxin Binding and High Affinity Interferon Receptor," The Journal of Biological Chemistry, Dec. 1987, vol. 262, No. 35, pp. 17088-17091.
Cohn et al., "The Immune System: A Look from a Distance," Frontiers in Bioscience, Oct. 1996, vol. 1, pp. d318-d323.
Colman, P.M., "Effects of amino acid sequence changes on antibody-antigen interactions," Research in Immunology, 1994, vol. 145, No. 1, pp. 33-36.
Cunney et al., "Clostridium difficile colitis associated with chronic renal failure," Nephrology Dialysis Transplantation, 1998, vol. 13, pp. 2842-2846.
Desmyter et al., "Camelid nanobodies: killing two birds with one stone," Current Opinion in Structural Biology, 2015, vol. 32, pp. 1-8.
Dobson et al., "Clostridium difficile colitis causing toxic megacolon, severe sepsis and multiple organ dysfunction syndrome," Intensive Care Medicine, 2003, vol. 29, p. 1030.
Dong et al., "A Single-Domain Llama Antibody Potently Inhibits the Enzymatic Activity of Botulinum Neurotoxin by Binding to the Non-Catalytic α-Exosite Binding Region," Journal of Molecular Biology, 2010, vol. 397, pp. 1106-1118.
Donohue-Rolfe et al., "Purification of Shiga Toxin and Shiga-Like Toxins I and II by Receptor Analog Affinity Chromatography with Immobilized P1 Glycoprotein and Production of Cross-Reactive Monoclonal Antibodies," Infection and Immunity, 1989, vol. 57, No. 12, pp. 3888-3893.
Dowling et al., "Phase 1 Safety and Pharmacokinetic Study of Chimeric Murine-Human Monoclonal Antibody cαStx2 Administered Intravenously to Healthy Adult Volunteers," Antimicrobial Agents and Chemotherapy, May 2005, vol. 49, No. 5, pp. 1808-1812.
Dupuy et al., "Regulation of toxin and bacteriocin synthesis in *Clostridium* species by a new subgroup of RNA polymerase σ-factors," Research in Microbiology, 2006, vol. 157, pp. 201-205.
Emsley et al., "Features and development of Coot," Acta Crystallographica Section D: Biological Crystallography, 2010, vol. 66, pp. 486-501.
Eubanks et al., "An in vitro and in vivo disconnect uncovered through high-throughput identification of botulinum neurotoxin A antagonists," Proceedings of the National Academy of Sciences of the United States of America, Feb. 2007, vol. 104, No. 8, pp. 2602-2607.
Eubanks et al., "Identification of a Natural Product Antagonist against the Botulinum Neurotoxin Light Chain Protease," ACS Medicinal Chemistry Letters, 2010, vol. 1, pp. 268-272.
Fan et al., "A three monoclonal antibody combination potently neutralizes multiple botulinum neurotoxin serotype F subtypes," PLoS One, 2017, vol. 12, No. 3, e0174187, pp. 1-16.
Fan et al., "Monoclonal Antibodies Targeting the Alpha-Exosite of Botulinum Neurotoxin Serotype/A Inhibit Catalytic Activity," PLoS One, 2015, vol. 10, No. 8, e0135306, pp. 1-23.
Fernie et al., "Active and passive immunization to protect against antibiotic associated caecitis in hamsters," Developments in Biological Standardization, 1983, vol. 53, pp. 325-332.
Tucker et al., "Toxin A of Clostridium difficile Binds to the Human Carbohydrate Antigens I, X, and Y" Infection and Immunity, Jan. 1991, vol. 59, No. 1, pp. 73-78.
Vance et al., "Stepwise Engineering of Heterodimeric Single Domain Camelid VHH Antibodies That Passively Protect Mice from Ricin Toxin," The Journal of Biological Chemistry, Dec. 20, 2013, vol. 288, No. 51, pp. 36538-36547.
Von Eichel-Streiber et al., "Large clostridial cytotoxins—a family of glycosyltransferases modifying small GTP- binding proteins," Trends in Microbiology, Oct. 1996, vol. 4, No. 10, pp. 375-382.
Wahl et al., "Molecular Hybridization of Immobilized Nucleic Acids: Theoretical Concepts and Practical Considerations," Methods in Enzymology, 1987, vol. 152, pp. 399-407.
Wang et al., "A Dileucine in the Protease of Botulinum Toxin A Underlies Its Long-lived Neuroparalysis," The Journal of Biological Chemistry, Feb. 25, 2011, vol. 286, No. 8, pp. 6375-6385.
Winn et al., "Overview of the CCP4 suite and current developments," Acta Crystallographica Section D: Biological Crystallography, 2011, vol. 67, pp. 235-242.
Witte et al., "Monoclonal antibodies targeting the VEGF receptor-2 (Flk1/KDR) as an anti-angiogenic therapeutic strategy," Cancer and Metastasis Reviews, 1998, vol. 17, pp. 155-161.
Wolff et al., "Direct Gene Transfer into Mouse Muscle in Vivo," Science, Mar. 23, 1990, vol. 247, pp. 1465-1468.
Yao et al., "A camelid single-domain antibody neutralizes botulinum neurotoxin A by blocking host receptor binding," Scientific Reports, 2017, vol. 7, Article No. 7438, pp. 1-12.
Yu et al., "Interaction between Bevacizumab and Murine VEGF-A: A Reassessment," Investigative Ophthalmology & Visual Science, Feb. 2008, vol. 49, No. 2, pp. 522-527.
Zar et al., "A Comparison of Vancomycin and Metronidazole for the Treatment of Clostridium difficile-Associated Diarrhea, Stratified by Disease Severity," Clinical Infectious Diseases, 2007, vol. 45, pp. 302-307.
Zuniga et al., "A Potent Peptidomimetic Inhibitor of Botulinum Neurotoxin Serotype A Has a Very Different Conformation than SNAP-25 Substrate," Structure, Oct. 8, 2008, vol. 16, pp. 1588-1597.
Zuniga et al., "Iterative Structure-Based Peptide-Like Inhibitor Design against the Botulinum Neurotoxin Serotype A," PLoS One, Jun. 2010, vol. 5, No. 6, e11378, pp. 1-15.

* cited by examiner

FIG. 6B

```
              FR1                                    FR2
JZS-C2    QVQLAESGGGLVQPGGSLRLSCAASGF----TSNSYYIGWFRQAPGKGREAVSSISSSGG    56
JZS-F6    QLQLAESGGGLVQPGGSLRLSCAASGI----TFSNVAMSWVRQAPGKGLEWVSTISTGGS    56
JZS-H4    QLQLVESGGGLVQPGGSLRLSCVASGF----NFSVQIMSWVRQAPGKGLEWVSAISTGGA    56
JZS-B9    QLQLVESGGGLVQPGGSLRLSCTSARF----SLINYAIGWFRQAPGQKREGVSLLTSGG-    55
JZS-H9    QVQLVESGGGLVQPGGSLTINCTVSGT----APSLDTMTWYRQAPGKQRELAADISSSG-    55
JZS-E6    QVQLAETGGGLVQAGGSLRLSCAASGRLSERIPMISTMAWYRQVPGKQRELVAEISRLG-    59
JZS-E4    QVQLVESGGGLAQAGGSLRLSCAASGS----SFSNNVMGWYRQPPGKQRELVATIRSDG-    55
JZS-B2    QVQLAESGGGLVQAGGSLRLSCVGSGT----SFPRNYMGWYRQAPGKQRELVAAISHDG-    55
JZS-C10   QLQLVE-TGGLVQAGGSLRLSCVGSGR----GPGINVMGWYRQAPGTERELVATWQTGG-    54
JZT-G9    QVQLAETGGGLVQAGGSLRLSCVSSER----NPGINAMGWYRQAPGSQRELVAVWQTGG-    55
JZS-A2a   QVQLAESGGGLVQAGGSLRLSCAASGS------VYTFMGWYRQAPGKTRELVAGISGGT-    53
JZT-F7    QVQLVETGGGLVQAGGSLRLSCAASGS------ILSSMGWYRQAPGNQREFVASISRTG-    53

FR3
JZS-C2    SPNYANAVKGRFTITRDNANNTV-YLQMDNLKPEDTAVYYCAASKFPLTT----MASNRY    111
JZS-F6    STSYLDSVKSRFTISRDNAKKTV-YLQMNSLKPEDTAVYYCVKGPKYSAT----I----R    107
JZS-H4    SKSYADFAKGRFTISRDNAKNTL-YLQMNSLQLEDTAVYFCSKGPRTWI------N----S    106
JZS-B9    ATYYADSARDRFTISRDNARNTV-YLQMNSLKPEDTAVYSCAAGPYSRTLVSRWKVGDGM    114
JZS-H9    ASNYLASVKGRFTISRDNAKSAL-YLQMNSLKPEDTGTYYCYRGRVRG----VWPLDSGM    110
JZS-E6    RANYSDSVTDRFIISRDNTKNTV-DLQMNSLKPEDTAVYYCNLKPFV-------------D    106
JZS-E4    ITNYAESVKGRFTISRDNVKNTV-HLEMNRLKAEDTAVYYCFHGRART------GNNADL    108
JZS-B2    NVEYADSVKGRFTISRGNFVNTV-ALQMNSLKSEDTAVYYCKLVTLRR------------D    103
JZS-C10   TTNYADSVKGRFTISRDNLKNTV-SLQMDSLKPEDTAVYYCYLKK-WR------------D    101
JZT-G9    SLSYADSVKGRFTISRDNLKNTV-YLQMNSLKPEDAAVYYCYLKK-WR------------D    102
JZS-A2a   ITKYADSVKGRFIISRDSPKNTI-YLQMNELKVEDTGVYYCNAGDTIAQ--AMGTRRFPF    110
JZT-F7    ATDYADSVAGRFIISRDRGKNTVLALQMDSLKPEDTAVYCNAGL-------GMGDPRRPG    107

FR4
JZS-C2    HYWGQGTQVTVSS    124
JZS-F6    RPEGQGTQVTVSS    120
JZS-H4    SPRGQGTQVTVSS    119
JZS-B9    EYWGKGTLVTVSS    127
JZS-H9    MYWGKGTLVTVSS    123
JZS-E6    NYRGPGTQVTVSS    119
JZS-E4    GSWGQGTQVTVSS    121
JZS-B2    EYWGQGTQVTVSS    116
JZS-C10   EYWGQGTQVTVSS    114
JZT-G9    QYWGQGTRVTVSS    115
JZS-A2a   DRWGQGTQVTVAS    123
JZT-F7    PWWGQGTQVTVSS    120
```

```
                   CDR1                                        CDR2                                              CDR3
JZS-C10  SGGGLVQAGGSLRLSCVSSQRGIPGINVMGWYRQAPGTEREIVATWQIGTTNIADSVRGRFTISRDNLRNTVSLQMDSLKPEDTAVYYCYLKWHDEYWGQGTQVTVSS
JZS-D5   SGGGSLVQAGGSLRLSCVSGRNPGINAMGWYRQAPGSQREIVAVWQTGRTIGRTNIADSVRGRFTISRDNLRNTVTLQMNSLKPEDTAVYYCYLKWHDETWGQGTQVTVSS
JZT-G9   TGGGSLVQAGGSLRLSCVSSERNPGINAMGWYRQAPGSQREIVAVWQTGSSLKPEDSVRGRFTISRDNLRNTVTLQMNSLKPEDAAVYYCYLKRWHDQTWGQGTRVTVTS
JZS-B3   SGGGSLVQAGGSLRLSCATSGANGINAMGWYRQAPGSQREIVATWQTGSTNIADSVRGRATISRDTAKNTVNLQMNSLKPEDTAVYYCILKRWHDYRWGQGTQVTVTS
JZT-G6   SGGGSLVQAGGSLRLSCVSSERNPGINAMGWYRQAPGSQREIVAVWQTGGSINIADSVRGRFTISRDNLRNTVTLQMNSLKPEDTAVYYCYLKWHDRIWGQGTQVTVSS
```

VHH POLYPEPTIDES THAT BIND TO *CLOSTRIDIUM DIFFICILE* TOXIN B AND METHODS OF USE THEREOF

CROSS REFERENCE TO RELATED APPLICATIONS

This application is the U.S. National Stage Application, pursuant to 35 U.S.C. § 371, of International PCT Application No. PCT/US2021/039798, filed Jun. 30, 2021, designating the United States and published in English, which claims priority to and benefit of U.S. Provisional Application No. 63/047,436, filed Jul. 2, 2020, the contents of all of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Aug. 2, 2021, is named 167774_012401PCT_SL.txt and is 94,095 bytes in size.

BACKGROUND

*Clostridium difficile* (*C. difficile* or *C. diff.*) microorganisms are enteric pathogens that infect many people worldwide causing loss of life and great economic cost. *C. diff.* is the most prevalent cause of hospital-acquired infectious diarrhea and life-threatening colitis worldwide. Yearly costs in the United States alone are estimated at $4.8 billion.

*C. diff.* infection (CDI) typically results from an unchecked growth and colonization of the pathogenic microorganism following anti-microbial therapies. The primary cause of CDI pathology is the production and release of exotoxins, especially toxin B, by the *C. diff.* pathogen. The toxin wreaks havoc with organs in the gastrointestinal system of infected individuals and severely disrupts the normal microflora that maintain gut health and homeostasis.

The emergence of hypervirulent drug-resistant *C. diff.* microorganisms has resulted in a global CDI epidemic that is largely due to high level production of *C. diff.* exotoxins, which cause CDI pathology.

Binding molecules, other than classical antibodies, that specifically bind to *C. diff.* toxins are needed for the treatment of disease and intoxication caused by *C. diff.* infection. The production and storage of classical antibodies involve labor-intensive and costly processes. In fact, the development of a single antibody therapeutic agent frequently requires years of clinical study and testing. Often, multiple, different therapeutic antibodies are necessary for the effective treatment of patients exposed to *C. diff.* or an outbreak of infection caused by this microorganism and its toxins. In addition, the shelf-life and stability of stored, classical antibodies are often relatively short (e.g., weeks or months), thus requiring the production of new batches of antibodies to replace those that have expired due to degradation or other adverse effects on the integrity of antibody proteins.

Thus, there is a need for new and cost effective therapeutic agents for treating the disease-causing microorganism *C. diff.*, as well as for treating subjects afflicted with CDI and its serious symptoms resulting from the toxins produced by *C. diff.* A profound need also exists for alternative therapeutics that are easier to develop and produce and have a longer shelf life for use against disease-causing *C. diff.* The present products, compositions and methods provide a solution to these needs.

SUMMARY

Described herein are VHH-based polypeptides (antibodies) that specifically bind to toxin B (also termed TcdB) produced by *Clostridium difficile* (*C. difficile*) microorganisms. The VHH polypeptides described herein are monomeric, single chain antibodies that bind to TcdB, i.e., anti-TcdB VHHs or anti-TcdB VHH molecules. In some embodiments, the anti-TcdB VHHs both bind to and neutralize TcdB produced by *C. difficile*. In some embodiments, the anti-TcdB VHHs bind to and neutralize TcdB in vitro and/or in vivo.

In an aspect, a polypeptide that specifically binds to *C. difficile* toxin B (TcdB), or a TcdB-binding portion thereof, is provided, wherein the polypeptide comprises three complementarity determining regions (CDRs), CDR1, CDR2 and CDR3, and four VHH framework regions (FRs), FR1, FR2, FR3 and FR4, with the general structure FR1-CDR1-FR2-CDR2-FR3-CDR3-FR4, wherein CDR1 comprises amino acid sequence GSVYTF (SEQ ID NO: 25); CDR2 comprises amino acid sequence SGGTITK (SEQ ID NO: 26); and CDR3 comprises amino acid sequence NAGDTIAQAMGTRRFPFDR (SEQ ID NO: 27);

wherein CDR1 comprises amino acid sequence GTSFPRNY (SEQ ID NO: 28); CDR2 comprises amino acid sequence SHDGNVE (SEQ ID NO: 29); and CDR3 comprises amino acid sequence KLVTLRRDEY (SEQ ID NO: 30);

wherein CDR1 comprises amino acid sequence RFSLINYA (SEQ ID NO: 31); CDR2 comprises amino acid sequence TSGGATY (SEQ ID NO: 32); and CDR3 comprises amino acid sequence AAGPYSRTLVSRWKVGDGMEY (SEQ ID NO: 33);

wherein CDR1 comprises amino acid sequence GFTSNSYY (SEQ ID NO: 34); CDR2 comprises amino acid sequence SSSGGSPN (SEQ ID NO: 35); and CDR3 comprises amino acid sequence AASKFPLTTMASNRYHY (SEQ ID NO: 36);

wherein CDR1 comprises amino acid sequence GRGPGINV (SEQ ID NO: 37); CDR2 comprises amino acid sequence QTGGTTN (SEQ ID NO: 38); and CDR3 comprises amino acid sequence YLKKWRDEY (SEQ ID NO: 39);

wherein CDR1 comprises amino acid sequence GSSFSMNV (SEQ ID NO: 40); CDR2 comprises amino acid sequence RSDGITN (SEQ ID NO: 41); and CDR3 comprises amino acid sequence FHGRARTGNNADLGS (SEQ ID NO: 42);

wherein CDR1 comprises amino acid sequence GRLSERIFMIST (SEQ ID NO: 43); CDR2 comprises amino acid sequence SRLGRAN (SEQ ID NO: 44); and CDR3 comprises amino acid sequence NLKPFVDNYR (SEQ ID NO: 45);

wherein CDR1 comprises amino acid sequence GITFSNVA (SEQ ID NO: 46); CDR2 comprises amino acid sequence STGGSSTS (SEQ ID NO: 47); and CDR3 comprises amino acid sequence VKGPKYSATIRRPE (SEQ ID NO: 48);

wherein CDR1 comprises amino acid sequence GFNFSVQI (SEQ ID NO: 49); CDR2 comprises amino acid sequence STGGASKS (SEQ ID NO: 50); and CDR3 comprises amino acid sequence SKGPRTWINSSPR (SEQ ID NO: 51);

wherein CDR1 comprises amino acid sequence GTAFSLDT (SEQ ID NO: 52); CDR2 comprises amino acid sequence SSSGASN (SEQ ID NO: 53); and CDR3 comprises amino acid sequence YRGRVRGVWPLDSGMMY (SEQ ID NO: 54);

wherein CDR1 comprises amino acid sequence GSILSS (SEQ ID NO: 55); CDR2 comprises amino acid sequence SRTGATD (SEQ ID NO: 56); and CDR3 comprises amino acid sequence NAGLGMGDPRRPGPW (SEQ ID NO: 57); or wherein CDR1 comprises amino acid sequence ERNP-GINA (SEQ ID NO: 58); CDR2 comprises amino acid sequence WQTGGSLS (SEQ ID NO: 59); and CDR3 comprises amino acid sequence YLKKWRDQY (SEQ ID NO: 60). In an embodiment, the four VHH FRs are camelid VHH FRs. In an embodiment, the polypeptide neutralizes *C. difficile* toxin B (TcdB) activity. In an embodiment, the polypeptide is a camelid-derived single domain anti-TcdB VHH antibody. In an embodiment, the polypeptide is in the form of a dimer or multimer. In an embodiment, the polypeptide comprises one or more epitope tag sequences specifically bindable by an anti-epitope tag antibody or binding portion thereof.

In an aspect, a polypeptide that specifically binds to *C. difficile* toxin B (TcdB) is provided, wherein the polypeptide or a TcdB-binding portion thereof has at least 85% amino acid sequence identity to a sequence selected from the group consisting of SEQ ID NOs: 1, 3, 5, 7, 9, 11, 13, 15, 17, 19, 21 and 23.

In an aspect, a polypeptide that specifically binds to *C. difficile* toxin B (TcdB) is provided, wherein the polypeptide or a TcdB-binding portion thereof has at least 90% amino acid sequence identity to a sequence selected from the group consisting of SEQ ID NOs: 1, 3, 5, 7, 9, 11, 13, 15, 17, 19, 21 and 23.

In an aspect, a polypeptide that specifically binds to *C. difficile* toxin B (TcdB) is provided, wherein the polypeptide or an antigen binding portion thereof has at least 95% amino acid sequence identity to a sequence selected from the group consisting of SEQ ID NOs: 1, 3, 5, 7, 9, 11, 13, 15, 17, 19, 21 and 23.

In an aspect, a polypeptide that specifically binds to *C. difficile* toxin B (TcdB) wherein the polypeptide or a TcdB-binding portion thereof has at least 98% amino acid sequence identity to a sequence selected from the group consisting of SEQ ID NOs: 1, 3, 5, 7, 9, 11, 13, 15, 17, 19, 21 and 23.

In an embodiment of any of the above-delineated aspects and embodiments, conservative amino acid substitutions in the polypeptide comprise the at least 85%, at least 90%, at least 95%, or at least 98% amino acid sequence identity.

In an aspect, a polypeptide that specifically binds to *C. difficile* toxin B (TcdB) is provided, wherein the polypeptide or a TcdB-binding portion thereof comprises a sequence selected from the group consisting of SEQ ID NOs: 1, 3, 5, 7, 9, 11, 13, 15, 17, 19, 21 and 23. In an aspect, a polypeptide that specifically binds to *C. difficile* toxin B (TcdB) wherein the polypeptide or a TcdB-binding portion thereof consists of a sequence selected from the group consisting of SEQ ID NOs: 1, 3, 5, 7, 9, 11, 13, 15, 17, 19, 21 and 23. In an embodiment of the above-delineated aspects, the polypeptide neutralizes TcdB activity. In an embodiment, the polypeptide is a camelid-derived single domain VHH antibody (VHH). In an embodiment, the polypeptide is in the form of a dimer or multimer.

In an embodiment of the above-delineated aspects, the polypeptide comprises one or more epitope tag sequences specifically bindable by an anti-epitope tag antibody or binding portion thereof. In an embodiment, the one or more epitope tag sequences comprises at least one of DEL-GPRLMGK (SEQ ID NO: 61) or GAPVPYPDPLEPR (SEQ ID NO: 62).

In another aspect, a dimeric or multimeric polypeptide comprising two or more anti-TcdB VHH polypeptides is provided, which comprises a sequence selected from the group consisting of SEQ ID NOs: 1, 3, 5, 7, 9, 11, 13, 15, 17, 19, 21 and 23, or TcdB binding regions thereof, wherein the two or more anti-TcdB VHH polypeptides, or TcdB binding regions, are joined with one or more linker peptides. In an embodiment, the one or more linker peptides is selected from GGGGS (SEQ ID NO: 63); GGGGSGGGGSGGGGS (SEQ ID NO: 64), or a functional portion thereof; EPKTPKPQGGGGSGGGGSGGGGSQGVQSQVQLVE (SEQ ID NO: 65); EPKTPKPQ (SEQ ID NO: 66); or a combination thereof. In an embodiment, the dimeric or multimeric polypeptide comprises one or more epitope tag sequences specifically bindable by an anti-epitope tag antibody or binding portion thereof. In an embodiment, the one or more epitope tag sequences comprises at least one of DELGPRLMGK (SEQ ID NO: 61) or GAPVPYPDPLEPR (SEQ ID NO: 62). In an embodiment, the polypeptide is dimeric and comprises two anti-TcdB VHH polypeptides. In an embodiment of the dimeric polypeptide, the two anti-TcdB VHH polypeptides are the same. In an embodiment of the dimeric polypeptide, the two anti-TcdB VHH polypeptides are different. In an embodiment, the polypeptide is multimeric and comprises at least three anti-TcdB VHH polypeptides. In an embodiment, the multimeric polypeptide comprises at least four anti-TcdB VHH polypeptides. In an embodiment, the multimeric polypeptide comprises three or four anti-TcdB VHH polypeptides. In an embodiment, the anti-TcdB VHH polypeptides of the multimeric polypeptide are the same. In an embodiment, the anti-TcdB VHH polypeptides of the multimeric polypeptide are different. In an embodiment, the anti-TcdB VHH polypeptides of the multimeric polypeptide are a combination of the same and different anti-TcdB VHH polypeptides.

In an aspect, an isolated polynucleotide encoding the polypeptide of the above-delineated aspects and embodiments is provided.

In an aspect, an isolated polynucleotide encoding the dimeric or multimeric polypeptide of the above-delineated aspects and embodiments is provided.

In an aspect, an isolated polynucleotide having at least 90% sequence identity to a nucleic acid sequence selected from the group consisting of SEQ ID NOs: 2, 4, 6, 8, 10, 12, 14, 16, 18, 20, 22 and 24 is provided.

In an aspect, an isolated polynucleotide having at least 95% sequence identity to a nucleic acid sequence selected from the group consisting of SEQ ID NOs: 2, 4, 6, 8, 10, 12, 14, 16, 18, 20, 22 and 24 is provided.

In an aspect, an isolated polynucleotide having at least 98% sequence identity to a nucleic acid sequence selected from the group consisting of SEQ ID NOs: 2, 4, 6, 8, 10, 12, 14, 16, 18, 20, 22 and 24 is provided.

In an aspect, an isolated polynucleotide comprising a sequence selected from the group consisting of SEQ ID NOs: 2, 4, 6, 8, 10, 12, 14, 16, 18, 20, 22 and 24 is provided. In an aspect, an isolated polynucleotide consisting of a sequence selected from the group consisting of SEQ ID NOs: 2, 4, 6, 8, 10, 12, 14, 16, 18, 20, 22 and 24 is provided.

In an aspect, an isolated polynucleotide comprising a nucleic acid sequence encoding an anti-TcdB VHH of any one of SEQ ID NOs: 1, 3, 5, 7, 9, 11, 13, 15, 17, 19, 21, or 23 is provided.

In an aspect, an isolated polynucleotide having at least 85% sequence identity to a nucleic acid sequence encoding an anti-TcdB VHH of any one of SEQ ID NOs: 1, 3, 5, 7, 9, 11, 13, 15, 17, 19, 21, or 23 is provided.

In an aspect, an isolated polynucleotide having at least 90% sequence identity to a nucleic acid sequence encoding an anti-TedB VHH of any one of SEQ ID NOs: 1, 3, 5, 7, 9, 11, 13, 15, 17, 19, 21, or 23 is provided.

In an aspect, an isolated polynucleotide having at least 95% sequence identity to a nucleic acid sequence encoding an anti-TcdB VHH of any one of SEQ ID NOs: 1, 3, 5, 7, 9, 11, 13, 15, 17, 19, 21, or 23 is provided.

In an aspect, an isolated polynucleotide having at least 98% sequence identity to a nucleic acid sequence encoding an anti-TcdB VHH of any one of SEQ ID NOs: 1, 3, 5, 7, 9, 11, 13, 15, 17, 19, 21, or 23 is provided.

In an aspect, a vector comprising a nucleic acid molecule that encodes a polypeptide as delineated in the above aspects is provided.

In an aspect, a vector comprising a nucleic acid molecule that encodes the dimeric or multimeric polypeptide as delineated in the above aspects is provided.

In an aspect, a vector comprising the isolated polynucleotide as delineated in the above aspects is provided. In an embodiment of the above-delineated aspects, the vector is an expression vector. In an embodiment, the expression vector is a viral or non-viral expression vector.

In an aspect, a host cell comprising the vector of any of the above-delineated aspects and embodiments is provided.

In an aspect, a non-naturally occurring *Spirulina* cyanobacterium ("*Spirulina* cyanobacterium") expressing the polypeptide of any of the above-delineated aspects and embodiments is provided. In an aspect, a non-naturally occurring *Spirulina* cyanobacterium comprising the isolated polynucleotide of any of the above-delineated aspects and embodiments is provided. In an embodiment, the *Spirulina* cyanobacterium is a stable transformant comprising at least one introduced targeted nucleotide mutation in its genome. In an embodiment, the *Spirulina* cyanobacterium is *Arthrospira platensis* or *Arthrospira maxima*. In an embodiment, the *Spirulina* cyanobacterium is *Arthrospira platensis* NIES-39 or *Arthrospira* sp. PCC 8005. In an embodiment, the *Spirulina* cyanobacterium is provided for treating disease, pathology and/or symptoms thereof caused by *C. difficile* infection or intoxication (CDI). In an embodiment, the *Spirulina* cyanobacterium is administered orally to a subject in need thereof. In an embodiment, the *Spirulina* cyanobacterium is administered enterically to a subject in need thereof.

In an aspect, a probiotic microorganism molecularly engineered to contain the isolated polynucleotide of any of the above-delineated aspects and embodiments is provided. In an embodiment, the probiotic microorganism is *E. coli* strain Nissle.

In an aspect, an enteric coated particle comprising the polypeptide of any of the above-delineated aspects or embodiments, or the isolated polynucleotide of any of the above-delineated aspects and embodiments is provided. In an embodiment, the particle comprises a protease resistant polypeptide, or a TcdB binding fragment thereof, of any of the above-delineated aspects or embodiments.

In an aspect, a pharmaceutical composition comprising an effective amount of the polypeptide of any of the above-delineated aspects or embodiments, or a TcdB binding fragment thereof, and a pharmaceutically acceptable excipient, carrier, or diluent is provided.

In an aspect, a pharmaceutical composition comprising an effective amount of the isolated polynucleotide of any of the above-delineated aspects or embodiments, and a pharmaceutically acceptable excipient, carrier, or diluent is provided.

In an aspect, a pharmaceutical composition comprising an effective amount of the probiotic microorganism of the above-delineated aspects and embodiments, or of the particle of the above-delineated aspects and embodiments, and a pharmaceutically acceptable excipient, carrier, or diluent is provided.

In an aspect, a pharmaceutical composition comprising an effective amount of the non-naturally occurring *Spirulina* cyanobacterium of any of the above-delineated aspects or embodiments, and a pharmaceutically acceptable excipient, carrier, or diluent is provided. In an aspect, a method of reducing, ameliorating, alleviating, abating, or eradicating intoxication of a cell by *C. difficile* toxin B (TcdB) is provided, in which the method comprises contacting the cell with an effective amount of the polypeptide of any one of the above-delineated aspects and embodiments, thereby reducing, ameliorating, alleviating, abating, or eradicating intoxication of the cell by TcdB.

In an aspect, a method of reducing, ameliorating, alleviating, abating, or eradicating intoxication of a cell by *C. difficile* toxin B (TcdB) is provided, in which the method comprises contacting the cell with an effective amount of the isolated polynucleotide of any one of the above-delineated aspects and embodiments: the non-naturally occurring *Spirulina* cyanobacterium of any one of the above-delineated aspects and embodiments: or the probiotic microorganism of the above-delineated aspects and embodiments, thereby reducing, ameliorating, alleviating, abating, or eradicating intoxication of the cell by TcdB.

In an embodiment of the above methods, the cell is an enteric cell of the gastrointestinal (GI) tract or the gut. In an embodiment of the above methods, the cell is in vitro. In an embodiment of the above methods, the cell is in vivo.

In an aspect, a method of treating *C. difficile* infection (CDI) and/or the symptoms thereof in a subject is provided, in which the method comprises administering to a subject in need thereof an effective amount of the polypeptide of any one of the above-delineated aspects and embodiments: the isolated polynucleotide of any one of the above-delineated aspects and embodiments: the non-naturally occurring *Spirulina* cyanobacterium of any one of the above-delineated aspects and embodiments: the probiotic microorganism of the above-delineated aspects and embodiments, or a pharmaceutical composition thereof, thereby treating CDI and/or the symptoms thereof in the subject.

In an aspect, a method of reducing the severity of *C. difficile* infection (CDI) or intoxication by *C. difficile* and/or the symptoms thereof in a subject who has, who is susceptible to, or who is at risk of CDI or intoxication by *C. difficile* is provided, in which the method comprises administering to a subject in need thereof an effective amount of the polypeptide of any one of the above-delineated aspects and embodiments: the isolated polynucleotide of any one of the above-delineated aspects and embodiments: the non-naturally occurring *Spirulina* cyanobacterium of any one of the above-delineated aspects and embodiments: the probiotic microorganism of the above-delineated aspects and embodiments, or a pharmaceutical composition thereof, thereby reducing the severity of *C. difficile* infection (CDI) or intoxication by *C. difficile* and/or the symptoms thereof in the subject.

In an aspect, a method of preventing *C. difficile* infection (CDI) and/or the symptoms thereof in a subject is provided, in which the method comprises administering to a subject in need thereof an effective amount of the polypeptide of any one of the above-delineated aspects and embodiments: the isolated polynucleotide of any one of the above-delineated aspects and embodiments: the non-naturally occurring *Spirulina* cyanobacterium of any one of the above-delineated aspects and embodiments: the probiotic microorganism of the above-delineated aspects and embodiments, or a pharmaceutical composition thereof, thereby preventing CDI and/or the symptoms thereof in the subject.

In an aspect, a method of treating or preventing *C. difficile* infection (CDI) and/or the symptoms thereof in a subject is provided, in which the method comprises administering to a subject in need thereof an effective amount of the particle of the above-delineated aspects and embodiments, or a pharmaceutical composition thereof, thereby treating CDI and/or the symptoms thereof in the subject.

In an embodiment of the above-delineated methods of reducing the severity or, preventing, or treating or preventing CDI, the CDI and the symptoms thereof cause one or more of *C. difficile*-associated diarrhea (CDAD), pseudomembranous colitis (PMC), bowel inflammation, enterocytic detachment, alteration, disruption, or elimination of natural intestinal microflora, and/or paralytic ileus. In another embodiment, the methods further comprise administering to the subject an anti-epitope tag antibody that specifically binds to an epitope tag, if present, and facilitates clearance of a complex of TcdB bound to the anti-TcdB VHH polypeptide from the subject.

In another aspect, a polypeptide that specifically binds to and neutralizes *C. difficile* toxin B (TcdB), or a TcdB-binding portion thereof, is provided, wherein the polypeptide comprises three complementarity determining regions (CDRs), CDR1, CDR2 and CDR3, and four VHH framework regions (FRs), FR1, FR2, FR3 and FR4, with the general structure FR1-CDR1-FR2-CDR2-FR3-CDR3-FR4,
wherein CDR1 comprises amino acid sequence RFSLINYA (SEQ ID NO: 31); CDR2 comprises amino acid sequence TSGGATY (SEQ ID NO: 32); and CDR3 comprises amino acid sequence AAGPYSRTLVSRWKVGDGMEY (SEQ ID NO: 33);
wherein CDR1 comprises amino acid sequence GFTSNSYY (SEQ ID NO: 34); CDR2 comprises amino acid sequence SSSGGSPN (SEQ ID NO: 35); and CDR3 comprises amino acid sequence AASKFPLTTMASNRYHY (SEQ ID NO: 36);
wherein CDR1 comprises amino acid sequence GRGPGINV (SEQ ID NO: 37);
CDR2 comprises amino acid sequence QTGGTTN (SEQ ID NO: 38); and CDR3 comprises amino acid sequence YLKKWRDEY (SEQ ID NO: 39);
wherein CDR1 comprises amino acid sequence GSSFSMNV (SEQ ID NO: 40); CDR2 comprises amino acid sequence RSDGITN (SEQ ID NO: 41); and CDR3 comprises amino acid sequence FHGRARTGNNADLGS (SEQ ID NO: 42);
wherein CDR1 comprises amino acid sequence GRLSERIFMIST (SEQ ID NO: 43); CDR2 comprises amino acid sequence SRLGRAN (SEQ ID NO: 44); and CDR3 comprises amino acid sequence NLKPFVDNYR (SEQ ID NO: 45);
wherein CDR1 comprises amino acid sequence GITFSNVA (SEQ ID NO: 46); CDR2 comprises amino acid sequence STGGSSTS (SEQ ID NO: 47); and CDR3 comprises amino acid sequence VKGPKYSATIRRPE (SEQ ID NO: 48);
wherein CDR1 comprises amino acid sequence GFNFSVQI (SEQ ID NO: 49); CDR2 comprises amino acid sequence STGGASKS (SEQ ID NO: 50); and CDR3 comprises amino acid sequence SKGPRTWINSSPR (SEQ ID NO: 51);
wherein CDR1 comprises amino acid sequence GSILSS (SEQ ID NO: 55); CDR2 comprises amino acid sequence SRTGATD (SEQ ID NO: 56); and CDR3 comprises amino acid sequence NAGLGMGDPRRPGPW (SEQ ID NO: 57); or
wherein CDR1 comprises amino acid sequence ERNPGINA (SEQ ID NO: 58); CDR2 comprises amino acid sequence WQTGGSLS (SEQ ID NO: 59); and CDR3 comprises amino acid sequence YLKKWRDQY (SEQ ID NO: 60). In an embodiment, the four VHH FRs are camelid VHH FRs.

In an aspect, a polypeptide that specifically binds to and neutralizes *C. difficile* toxin B (TcdB) is provided, wherein the polypeptide or a TcdB-binding portion thereof has at least 90% sequence identity to a sequence selected from the group consisting of SEQ ID NOs: 5, 7, 9, 11, 13, 15, 17, 21 and 23.

In an aspect, a polypeptide that specifically binds to and neutralizes *C. difficile* toxin B (TcdB) is provided, wherein the polypeptide or a TcdB-binding portion thereof has at least 95% sequence identity to a sequence selected from the group consisting of SEQ ID NOs: 5, 7, 9, 11, 13, 15, 17, 21 and 23 is provided.

In an aspect, a polypeptide that specifically binds to and neutralizes *C. difficile* toxin B (TcdB) is provided, wherein the polypeptide or an antigen binding portion thereof comprises a sequence selected from the group consisting of SEQ ID NOs: 5, 7, 9, 11, 13, 15, 17, 21 and 23.

In an embodiment of the above-delineated aspects of the polypeptide, conservative amino acid substitutions in the polypeptide comprise the at least 90% or the at least 95% amino acid sequence identity. In an embodiment, the polypeptide is a camelid-derived single domain anti-TcdB VHH antibody. In an embodiment, the polypeptide is in the form of a dimer or multimer. In an embodiment, the polypeptide comprises one or more epitope tag sequences specifically bindable by an anti-epitope tag antibody or binding portion thereof.

In an aspect, an isolated polynucleotide encoding the polypeptide of the above-delineated aspects and embodiments is provided.

In an aspect, a pharmaceutical composition comprising an effective amount of the polypeptide of any of the above-delineated aspects and embodiments, or a TcdB-binding fragment thereof, or an effective amount of the above-delineated isolated polynucleotide, and a pharmaceutically acceptable excipient, carrier, or diluent is provided.

In an aspect, a non-naturally occurring *Spirulina* cyanobacterium expressing the polypeptide of any one of the above-delineated aspects and embodiments, or comprising the above-delineated isolated polynucleotide and embodiments thereof is provided.

In an aspect, a probiotic microorganism molecularly engineered to contain the above-delineated isolated polynucleotide and embodiments thereof, optionally wherein the microorganism is *E. coli* strain Nissle, is provided.

In an aspect, an enteric coated particle comprising the polypeptide of any one of the above-delineated aspects and embodiments or the above-delineated isolated polynucleotide and embodiments thereof is provided. In an embodiment, the polypeptide or the TcdB-binding fragment thereof, is protease resistant.

In an aspect, a method of treating or preventing *C. difficile* infection (CDI) and/or the symptoms thereof in a subject is provided, wherein the method comprises administering to a subject in need thereof an effective amount of the above-delineated pharmaceutical composition, thereby treating CDI and/or the symptoms thereof in the subject.

In an aspect, a method of treating or preventing *C. difficile* infection (CDI) and/or the symptoms thereof in a subject is provided, in which the method comprises administering to a subject in need thereof an effective amount of the above-delineated non-naturally occurring *Spirulina* cyanobacterium, thereby treating CDI and/or the symptoms thereof in the subject.

In an aspect, a kit comprising the polypeptide of any one of the above-delineated aspects or embodiments, or a pharmaceutical composition thereof, is provided for treating or protecting against disease or intoxication and/or the symptoms thereof caused by *C. difficile* toxin B.

In an aspect, a kit comprising the isolated polynucleotide of any one of the above-delineated aspects or embodiments, or a pharmaceutical composition thereof, is provided for treating or protecting against disease or intoxication and/or the symptoms thereof caused by *C. difficile* toxin B.

In an aspect, a kit comprising the non-naturally occurring *Spirulina* cyanobacterium of the above-delineated aspects and embodiments: the probiotic microorganism of the above-delineated aspects and embodiments: the particle of the above-delineated aspects and embodiments, or a pharmaceutical composition thereof, is provided for treating or protecting against disease or intoxication and/or the symptoms thereof caused by *C. difficile* toxin B.

In an embodiment, the kit of any one of the above-delineated aspects further comprises instructions for use.

In an aspect, a polypeptide that specifically binds to *C. difficile* toxin B (TcdB), or a TcdB-binding portion thereof, is provided, wherein the polypeptide comprises three complementarity determining regions (CDRs), CDR1, CDR2 and CDR3, and four VHH framework regions (FRs), FR1, FR2, FR3 and FR4, with the general structure FR1-CDR1-FR2-CDR2-FR3-CDR3-FR4, wherein CDR1 comprises 8 amino acids, $X_1$-$X_8$, wherein $X_1$ is G or E; $X_2$ is R or A; $X_3$ is G or N; $X_4$ is P or L; $X_5$ is G; $X_6$ is I; $X_7$ is N; and $X_8$ is V or A;

wherein CDR2 comprises 7 amino acids, $X_1$-$X_7$, wherein $X_1$ is Q; $X_2$ is T; $X_3$ is G; $X_4$ is G; $X_5$ is T, R, or S; $X_6$ is T or L; and $X_7$ is N or S; and wherein CDR3 comprises 9 amino acid, $X_1$-$X_9$, wherein $X_1$ is Y; $X_2$ is L or Q; $X_3$ is K; $X_4$ is K or R; $X_5$ is W; $X_6$ is R; $X_7$ is D or N; $X_8$ is E, Q, D, or R; and $X_9$ is Y.

In an embodiment, the four VHH FRs are camelid VHH FRs. In an embodiment, the polypeptide neutralizes *C. difficile* toxin B (TcdB) activity. In an embodiment, the polypeptide is a camelid-derived single domain anti-TcdB VHH antibody. In an embodiment, the polypeptide is in the form of a dimer or multimer. In an embodiment, the polypeptide or dimeric or multimeric form thereof comprises one or more epitope tag sequences specifically bindable by an anti-epitope tag antibody or binding portion thereof.

In an aspect, a method of reducing the severity of *C. difficile* infection (CDI) or intoxication by *C. difficile* and/or the symptoms thereof in a subject who has, who is susceptible to, or who is at risk of CDI or intoxication by *C. difficile*, wherein the method comprises administering to a subject in need thereof an effective amount of the above-delineated polypeptide and embodiments thereof, or a pharmaceutical composition thereof, thereby reducing the severity of *C. difficile* infection (CDI) or intoxication by *C. difficile* and/or the symptoms thereof in the subject. In an embodiment of the method, the polypeptide or the pharmaceutical composition thereof is administered to the subject prior or subsequent to infection by *C. difficile*.

In an embodiment of any of the above-delineated methods and embodiments thereof, the polypeptide, any composition or pharmaceutical composition thereof, is administered to the subject prior or subsequent to infection by *C. difficile*. In another embodiment of any of the above-delineated methods and embodiments thereof, the subject is to receive or has received antibiotics or a course of antibiotics to treat a non-*C. difficile* bacterial infection.

Definitions

Unless defined otherwise, all technical and scientific terms used herein have the meaning commonly understood by a person skilled in the art to which the described aspects and embodiments belongs. The following references provide one of skill with a general definition of many of the terms used in the aspects and embodiments described herein: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). The following terms have the meanings ascribed to them below, unless specified otherwise.

In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used in the specification and claim(s) herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions and products of the present disclosure can be used to achieve methods of the present disclosure.

Unless specifically stated or obvious from context, as used herein, the term "about" or "approximately" means within an acceptable error range for the particular value as determined by one of ordinary skill in the art, which will depend, in part, on how the value is measured or determined, i.e., the limitations of the measurement system. For example, "about" can mean within 1 standard deviation or more than 1 standard deviation, e.g., 2 standard deviations of the mean, as typically practiced in the art. Alternatively, and without intending to be limiting. "about" can mean a range of up to 20%, up to 10%, up to 5%, up to 2%, or up to 1% of a given value. Alternatively, and particularly for biological systems or processes, the term can mean within an order of magnitude, e.g., within 5-fold, within 3-fold, within 2.5-fold, or within 2-fold of a value. Where particular values are described in the application and claims, unless otherwise stated, the term "about" means within an acceptable error range for the particular value.

Reference herein to "some embodiments," "an embodiment," "one embodiment" or "other embodiments" means that a particular feature, structure, or characteristic described in connection with the embodiments is included in at least some embodiments, but not necessarily all embodiments, of the disclosure.

By "agent" is meant any small molecule chemical compound, antibody, nucleic acid molecule, or polypeptide (e.g., antibody or VHH antibody), or fragments thereof.

By "ameliorate" is meant decrease, reduce, diminish, suppress, attenuate, arrest, or stabilize the development or progression of a disease or pathology.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "antibody" is meant any immunoglobulin polypeptide, or fragment thereof, having immunogen or antigen binding ability. Antibody structure is well known in the art. Briefly, the variable (V) regions or domains of antibody heavy (H) and light (L) chains contain Complementarity-Determining Regions (CDRs), which bind to specific antigens or immunogens (e.g., protein antigens or immunogens). CDRs are situated within framework (FR) sequences of the V regions of the heavy ($V_H$) and light chains ($V_L$) of an antibody. CDRs are the most variable parts of antibodies and are critical components in the diversity of antigen specificities of antibodies produced by B lymphocytes. In general, three CDRs (CDR1, CDR2 and CDR3) are arranged consecutively in a V domain of an antibody. Because a VHH, such as a camelid VHH, is essentially a single chain antibody polypeptide, it contains three CDRs that bind to an antigen or target protein such as a toxin (e.g., TcdB) in the context of four framework (FR) regions, as follows: FR1-CDR1-FR2-CDR2-FR3-CDR3-FR4. Thus, as would be appreciated by the skilled practitioner in the art, in a VHH polypeptide sequence, FR1 comprises the amino acids positioned to the left of CDR1; FR2 comprises the amino acids positioned between CDR1 and CDR2; FR3 comprises the amino acids positioned between CDR2 and CDR3; and FR4 comprises the amino acids positioned to the right of CDR3. Because most of the sequence variability associated with immunoglobulins and antigen binding is found in the CDRs, these regions are sometimes referred to as hypervariable regions. Typically, CDR1, CDR2 and CDR3 of VHHs contribute to and/or do not interfere with antigen binding. The CDRs of a number of anti-TcdB VHHs described herein are shown, for example, in Table 1, FIGS. 5A-5C and FIGS. 7A and 7B.

The FRs of a number of anti-TcdB VHHs described herein are shown, for example, in FIG. 6B.

A "chimeric antibody" refers to an antibody in which the constant region of an antibody of one species (e.g., rodent, mouse or rat) is replaced with that from a human to achieve a more human-like antibody. Chimeric antibodies may be recombinantly generated by combining the variable light and heavy chain regions obtained from antibody producing cells of one species with the constant light and heavy chain regions from another. In general, chimeric antibodies utilize rodent (or other species, such as rabbit or camelid) variable regions and human constant regions in order to produce an antibody with predominantly human constant domains. The production of chimeric antibodies is well known in the art, and may be achieved by standard means, for example, as described in U.S. Pat. No. 5,624,659, incorporated fully herein by reference.

By "binding to" a molecule is meant having a physicochemical affinity for that molecule or a region of the molecule, e.g., an epitope. Binding may be measured by any of the methods practiced in the art, e.g., using an antibody binding assay or an in vitro translation binding assay.

"Detect" refers to identifying or determining the presence, absence or amount of an analyte to be detected.

By "detectable label" is meant a compound, substance, or composition that, when linked to a molecule of interest, renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition, disorder, or pathology that damages or interferes with the normal function of a cell, tissue, or organ. Examples of diseases include, without limitation, *C. difficile* infection (CDI), *C. difficile*-associated diarrhea (CDAD), pseudomembranous colitis (PMC), bowel inflammation, enterocytic detachment, alteration, disruption, or elimination of natural intestinal microflora, and/or paralytic ileus caused by *C. difficile* infection, or one or more symptoms of these diseases. The production of toxins by the pathogenic and infectious *C. difficile* microorganisms results in intoxication of the subject (or patient), which is an abnormal state that is a poisoning of the subject (and the subject's cells, tissues and organs) by the presence and activity of the produced toxins.

By "effective amount" is meant the amount of a required to ameliorate, or optimally eliminate, the symptoms of a disease relative to an untreated patient. The effective amount of active compound(s) used to practice the present aspects and embodiments for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

An "epitope tag" refers to a peptide or amino acid sequence (epitope) that is fused, linked, or coupled to a protein, such as a recombinant protein produced by recombinant techniques, and that can be specifically bound by an antibody, e.g., an anti-tag monoclonal antibody or binding molecule that is directed to or generated against the tag peptide or amino acid sequence. Epitope tags are typically short peptide sequences (e.g., from about 5-30 amino acids, or sometimes up to 40 amino acids, that are selected because high-affinity antibodies can be reliably produced in many different species. Such anti-epitope tag antibodies are optimally not cross-reactive with other human peptides or polypeptides and typically do not generate an antibody response, e.g., an anti-tag antibody response, when administered or delivered to a subject. An epitope tag sequence that is fused to a protein provides for the detection and/or purification of the protein using an antibody, e.g., a monoclonal antibody, that specifically binds to the epitope tag. In an embodiment, the protein to which an epitope tag is fused, linked, or coupled is an antibody or VHH protein, e.g., a recombinantly produced antibody or VHH protein. In an embodiment, the VHH is an anti-TcdB VHH antibody. In an embodiment, the protein, or a dimeric or multimeric form thereof, may include one or more epitope tags. In an embodiment, an epitope tag is coupled to the amino (NH) terminus of the protein, e.g., a VHH antibody as described herein. In an embodiment, an epitope tag is coupled to the carboxy (COOH) terminus of the protein, e.g., a VHH antibody as described herein. In an embodiment, an epitope tag is coupled to the NH and the COOH termini of the protein, e.g., a VHH antibody as described herein. In an embodiment, a dimeric or multimeric form of the protein includes one or more, e.g., two, three or four, epitope tags linked to one or more of the VHHs comprising the dimeric or multimeric form of the protein. Such epitope tags may be coupled to the VHH components at locations within the dimer or multimer molecule, or at the NH and/or COOH termini of the molecule. In some embodiments, two or more epitope tags may be coupled to a VHH protein in tandem within or at the termini of the VHH protein or dimeric or multimeric form thereof. Examples of epitope tags include, without limitation. FLAG tags (peptide sequence DYKDDDDK (SEQ ID NO: 67) recognized by an anti-FLAG antibody). poly Histidine (His) tags (5-10 histidine residues (SEQ ID NO: 68) (HHHHHH (SEQ ID NO: 69)) bound by a nickel or cobalt chelate). E-tag, a peptide comprising amino acid sequence GAPVPYPDPLEPR (SEQ ID NO: 62) recognized by an antibody; and the epitope tag sequences described herein, which are bound by anti-epitope tag antibodies, forming complexes which may facilitate clearance of the protein containing the tags from the body or system. (See, also, B. Brizzard and R. Chubet, 2001, *Curr Protoc Neurosci.*, Chapter 5. Unit 5.8; DOI: 10.1002/0471142301.ns0508s00; R. Hernan et al., 2000, *Biotechniques*, 28(4); 789-793; C. E. Fritze et al., 2000, *Meths Enzymol.*, 327:3-16; doi: 10.1016/s0076-6879(00)27263-7; A. Einhauer et al., 2001, *J Biochem Biophys Methods*, 49(1-3); 455-65, doi: 10.1016/s0165-022x(01)00213-5)).

A "framework (FR) region" or "FR region" includes amino acid residues that are adjacent to the CDRs in $V_H$, and $V_L$ regions, and in VHHs. For example, FR region residues may be present in VHHs as described herein, human antibodies, rodent-derived antibodies (e.g., murine and rat antibodies), humanized antibodies, primatized antibodies, chimeric antibodies, antibody fragments (e.g., Fab fragments), VHHs, single-chain antibody fragments (e.g., scFv fragments), antibody domains, and bispecific antibodies, among others. Also by way of example, in a VHH polypeptide sequence, FR1 comprises the amino acids positioned to the left of CDR1; FR2 comprises the amino acids positioned between CDR1 and CDR2; FR3 comprises the amino acids positioned between CDR2 and CDR3; and FR4 comprises the amino acids positioned to the right of CDR3.

By "fragment" is meant a portion of a polypeptide or nucleic acid molecule. This portion contains, preferably, at least 10%, 20%, 30%, 40%, 50%, 60%, 70%, 80%, 90%, or 95% of the entire length of the reference nucleic acid molecule or polypeptide, including percent values between those enumerated. A fragment may contain 10, 20, 30, 40, 50, 60, 70, 80, 90, or 100, 200, 300, 400, 500, 600, 700, 800, 900, or 1000 nucleotides or amino acids. In an embodiment, a fragment or portion possesses or retains activity or function of the polypeptide from which it is derived.

The term "humanized" antibodies refers to forms of non-human (e.g., murine) antibodies, camelid-derived single domain antibody (sdAb) binding molecules, which are comprised of the heavy chain variable (Vu) region of heavy-chain-only antibodies (Abs) or VHHs. Humanized antibodies include chimeric immunoglobulins, immunoglobulin chains or fragments thereof (such as Fv, Fab, Fab', F(ab')$_2$ or other target-binding subdomains of antibodies) which contain minimal sequences derived from non-human immunoglobulin. In general, a humanized antibody or VHH may comprise substantially all of at least one variable domain (or two variable domains in the case of non-VHH antibodies), in which all or substantially all of the CDR regions correspond to those of a non-human immunoglobulin. All or substantially all of the FR regions of a humanized antibody may also be derived from a human immunoglobulin sequence. In the case of non-VHH antibodies, a humanized antibody can also comprise at least a portion of an immunoglobulin constant region (Fc), which may be that of a human immunoglobulin consensus sequence. Techniques and protocols for humanizing antibodies (as well as VHHs) are known and practiced in the art, as described, for examples, in Riechmann et al., *Nature*, 332:323-7, 1988; Kasmiri et al., *Methods*, 36(1); 25-34, 2005; U.S. Pat. Nos. 5,530,101; 5,585,089; 5,693,761; 5,693,762; and 6,180,370 to Queen et al: EP239400; WO 1991/09967; U.S. Pat. No. 5,225,539; EP592106; and EP519596, the contents of which are incorporated herein by reference. Humanized antibodies or VHHs are molecularly engineered to contain even more human-like immunoglobulin domains, and incorporate only the CDRs of the VHH or animal-derived monoclonal antibody by carefully examining the sequence of the hypervariable loops of the V regions of the monoclonal antibody or VHH, and fitting them to the structure of the human antibody chains. This process is routinely and commonly carried out by one having skill in the art. See, e.g., U.S. Pat. No. 6,187,287, the contents of which are incorporated by reference herein.

The terms "isolated," "purified," or "biologically pure" refer to material that is free to varying degrees from components which normally accompany it as found in its native state. "Isolate" denotes a degree of separation from original source or surroundings. "Purify." denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of the aspects and embodiments disclosed and described herein is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

As used herein, the terms "polynucleotide," "DNA molecule" or "nucleic acid molecule" include both sense and anti-sense strands, cDNA, genomic DNA, recombinant DNA, RNA, mRNA, and wholly or partially synthesized nucleic acid molecules. A nucleotide "variant" is a sequence that differs from the recited nucleotide sequence in having one or more nucleotide deletions, substitutions or additions. Such modifications are readily introduced using standard mutagenesis techniques, such as oligonucleotide-directed site-specific mutagenesis as described, for example, in Adelman et al., 1983, DNA 2:183. Nucleotide variants are naturally-occurring allelic variants, or non-naturally occurring variants. Variant nucleotide sequences in various embodiments exhibit at least about 70%. 75%, 80%, 85%, 90%, 95%, 98%, 99%, or 100% sequence homology or sequence identity to the recited sequence. Such variant nucleotide sequences hybridize to the recited nucleotide sequence under stringent hybridization conditions. In one embodiment, "stringent conditions" refers to prewashing in a solution of 6×SSC, 0.2% SDS; hybridizing at 65° Celsius, 6×SSC, 0.2% SDS overnight; followed by two washes of 30 minutes each in 1×SSC. 0.1% SDS at 65°C, and two washes of 30 minutes each in 0.2×SSC, 0.1% SDS at 65° C.

By "isolated polynucleotide" is meant a nucleic acid (e.g., DNA, cDNA, RNA, mRNA) that is free of the genes, which, in the naturally-occurring genome of the organism from which the nucleic acid molecule of the aspects and embodiments described herein is derived, flank the gene. The term therefore includes, for example, a recombinant DNA that is incorporated into a vector: into an autonomously replicating plasmid or virus: or into the genomic DNA of a prokaryote or eukaryote: or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, e.g., mRNA, as well as a recombinant DNA that is part of a hybrid gene encoding additional polypeptide sequence.

The terms "protein", "peptide" and "polypeptide" are used herein to describe any chain of amino acid residues, regardless of length or post-translational modification (for example, glycosylation or phosphorylation). Thus, these terms can be used interchangeably herein to refer to a polymer of amino acid residues. The terms also apply to amino acid polymers in which one or more amino acid residue is an artificial chemical mimetic of a corresponding naturally occurring amino acid. Thus, the term "polypeptide" includes full-length proteins, which may be, but need not be, naturally occurring, as well as recombinantly or synthetically produced polypeptides that correspond to a full-length protein, or to particular domains or portions of a protein, which may be, but need not be, naturally occurring. The term also encompasses mature proteins which have an added amino-terminal methionine to facilitate expression in prokaryotic cells. The binding molecules of the aspects and embodiments described herein are encoded by polynucleotides and can be chemically synthesized or synthesized by recombinant DNA methods.

By an "isolated polypeptide" is meant a polypeptide of the aspects and embodiments described herein that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the aspects and embodiments described herein. An isolated polypeptide of the aspects and embodiments described herein may be obtained, for example, by extraction from a natural source, by expression of a recombinant nucleic acid encoding such a polypeptide: or by chemically synthesizing the protein. Purity can be measured by any appropriate method, for example, column chromatography, polyacrylamide gel electrophoresis, or by HPLC analysis.

As used herein, "obtaining" as in "obtaining an agent" includes synthesizing, purchasing, deriving, isolating, or otherwise acquiring the agent.

By "operably linked" is meant the connection between regulatory elements and one or more polynucleotides (genes) or a coding region. That is, gene expression is typically placed under the control of certain regulatory elements, including constitutive or inducible promoters, tissue-specific regulatory elements, and enhancers. A polynucleotide (gene or genes) or coding region is said to be "operably linked to" or "operatively linked to" or "operably associated with" the regulatory elements, meaning that the polynucleotide (gene or genes) or coding region is controlled or influenced by the regulatory elements. The one or more polynucleotides may be separated by spacers or linkers.

By "pathogen" is meant any harmful microorganism, bacterium, virus, fungus, or protozoan capable of interfering with the normal function of a cell. Pathogens as referred to herein produce toxins, e.g., protein toxins, that intoxicate the cells, tissues and organs of a host or recipient organism and cause disease and pathology, often severe, unless they are bound by, neutralized and eliminated from the organism to the extent possible, such as by action of the VHH binding molecules (antibodies) described herein. As described herein, the bacterial pathogen *Clostridium difficile* produces toxin proteins that intoxicate a subject after infection. Toxin A and toxin B proteins produced by *C. difficile* translocate to the cytosol of target cells (mainly of the intestinal epithelium, but also in other cells) and inactivate cellular GTP-binding proteins, e.g., Rho, Rac and Cdc42, by monoglucosylation, which causes actin condensation, cell rounding and death. (reviewed by D. Voth and D. Ballard, 2005, *Clin. Microbiol. Rev.*, Vol. 18 (2); 247-263). In particular, the VHH antibodies described herein are directed against and bind toxin B of *C. difficile* (TcdB). In embodiments, the anti-TcdB VHHs described herein neutralize TcdB, thereby inhibiting, blocking, or reducing its toxicity and toxic effects in vitro or in vivo.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

By "reduces" is meant a negative or lowering alteration of at least 5%, 10%, 15%, 10%, 25%, 50%, 75%, or 100%.

By "reference" is meant a standard or control condition typically used as a comparator in an assay, test, experiment, or trial, as would be understood by one having skill in the pertinent art. In various nonlimiting embodiments, a reference or control is a different or nonpathogenic protein or cell, such as a non-toxin (or different toxin) protein or a normal cell, a wild-type (unmutated or unaltered) protein, or a healthy subject or individual.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant a compound, molecule, antibody, or VHH that recognizes and binds a protein, peptide, or polypeptide (e.g., an amino acid sequence of the protein, peptide, or polypeptide), but which does not substantially recognize and bind other molecules in a sample, for example, a biological sample, which may contain the protein, peptide, or polypeptide that is specifically bound.

"Nucleic acid" (also called polynucleotide herein) refers to deoxyribonucleotides or ribonucleotides and polymers thereof in either single- or double-stranded form. The term encompasses nucleic acids (polynucleotides) containing known nucleotide analogs or modified backbone residues or linkages, which are synthetic, naturally occurring, and non-naturally occurring, which have similar binding properties as a reference nucleic acid, and which are metabolized in a manner similar to the reference nucleic acid. Examples of such analogs include, without limitation, phosphorothioates, phosphoramidates, methyl phosphonates, chiral methyl phosphonates, 2-O-methyl ribonucleotides, and peptide-nucleic acids (PNAs). Unless otherwise indicated, a particular nucleic acid sequence also implicitly encompasses conservatively modified variants thereof (for example, degenerate codon substitutions) and complementary sequences, as well as the sequence explicitly indicated. Specifically, degenerate codon substitutions may be achieved by generating sequences in which the third position of one or more selected (or all) codons is substituted with suitable mixed base and/or deoxyinosine residues (Batzer et al., 1991, *Nucleic Acid Res,* 19:081; Ohtsuka et al., 1985, *J. Biol. Chem.,* 260:2600-2608; Rossolini et al., 1994, *Mol. Cell Probes,* 8:91-98). The term nucleic acid can be used interchangeably with gene, cDNA, mRNA, oligonucleotide, and polynucleotide.

Nucleic acid molecules or polynucleotides useful in the aspects and embodiments described herein include any nucleic acid molecule or polynucleotide that encodes a polypeptide, e.g., a heteromultimeric binding molecule, of the described aspects and embodiments, or a component or portion thereof. Nucleic acid molecules useful in the methods described herein include any polynucleotide or nucleic acid molecule that encodes a polypeptide e.g., heteromultimeric binding molecule, as described in the aspects and embodiments herein, or a component or portion thereof that has substantial identity to the binding molecule. Such nucleic acid molecules need not be 100% identical with the nucleic acid sequence of the binding molecule, but will typically exhibit substantial identity. Polynucleotides having "substantial identity" to a binding molecule sequence are typically capable of hybridizing with at least one strand of a double-stranded nucleic acid molecule.

By "hybridize" is meant pair to form a double-stranded molecule between complementary polynucleotide sequences (e.g., a gene described herein), or portions thereof, under various conditions of stringency. (See. e.g., Wahl, G. M, and S. L. Berger, 1987, *Methods Enzymol.* 152:399; Kimmel, A. R., 1987, *Methods Enzymol.* 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° ° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° ° C. in 250 mM NaCl, 25 mM trisodium citrate, 1% SDS, 50% formamide, and 200 g/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

"Percentage of sequence identity" means the value determined by comparing two optimally aligned sequences over a comparison window, wherein the portion of the polynucleotide sequence in the comparison window may comprise additions, substitutions, or deletions (i.e., gaps) as compared to the reference sequence (which does not comprise additions, substitutions, or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "homologous" in their various grammatical forms in the context of polynucleotides means that a polynucleotide comprises a sequence that has a desired identity, for example, at least 60% identity, at least 70% sequence identity, at least 80%, at least 85% identity, at least 90% identity; and at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like.

Substantial identity of amino acid sequences, for example, the anti-TcdB polypeptides (*C. diff.* toxin B-binding VHH polypeptides) refers to sequence identity between or among amino acid sequences of at least 60%, at least 65%, at least 70%, at least 75%, at least 80%, at least 85%, at least 88%, at least 90%, at least 95%, at least 98%, at least 99% or greater sequence identity. In embodiments, 100% identity between or among the amino acid sequences, e.g., the CDR1-3 sequences of the anti-TcdB VHHs as described herein is not required for binding of these polypeptides to toxin B and/or neutralization of toxin. In a particular embodiment, variations between or among VHH amino acid sequences encompass one or more conservative amino acid substitutions in the sequence, for example, as described and presented in Table 3 herein. In an embodiment, one or more conservative amino acid substitutions in an anti-TcdB VHH amino acid sequence may be in one or more CDR sequences, one or more FR sequences, or a combination thereof.

As will be appreciated by the skilled practitioner in the art, some amino acids in a VHH antibody can be modified without significantly altering antigen binding of the VHH antibody. For example, such amino acid sequence modification occurs frequently during in vivo affinity maturation of VHH antibodies, and the best mutations, e.g., for specific and/or high affinity binding to antigen, are positively selected for in the animal during the molecular production of antibodies. It is possible to isolate different VHH intermediates in the affinity maturation process that possess acceptable and specific antigen binding properties and that have significant variations in their CDR sequences.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

By "subject" is meant a mammal, including, but not limited to, a human or non-human mammal, such as, without limitation, a human, a non-human primate, or a bovine, equine, canine, ovine, or feline mammal. Other mammals include rabbits, goats, llamas, mice, rats, guinea pigs, camels and gerbils. In particular, a "subject" as used herein refers to a human subject, such as a human patient or individual. In some cases, the terms subject, patient and individual are used interchangeably herein.

A "VHH binding molecule" or "VHH antibody," or simply "VHH," as referred to herein is, in general, a single domain immunoglobulin molecule (antibody) isolated from camelid animals or alpacas, e.g., as described in Maass, D. R., 2007, *J. Immunol. Methods,* 324(1-2); 13-15). A VHH (or VHH antibody) corresponds to the heavy chain of a camelid antibody having a single variable domain (or single variable region), e.g., a camelid-derived single variable H ($V_H$) domain antibody. A VHH has a molecular weight (MW) of about 15 kDa. VHH technology is based on fully functional antibodies from camelids that lack light chains. These heavy-chain antibody molecules contain a single variable domain (VHH) and, typically, two constant domains ($CH_2$ and $CH_3$). A cloned (recombinantly produced) and isolated VHH domain is a stable polypeptide harboring the antigen-binding capacity of the original heavy-chain antibody. See, e.g., U.S. Pat. Nos. 5,840,526 and 6,015,695, each of which is incorporated by reference herein in its entirety. VHHs, called NANOBODIES™, may be produced commercially (Ablynx Inc., Ghent, Belgium).

VHHs are efficiently expressed in *E. coli*, coupled to detection markers, such as a fluorescent marker, or conjugated with enzymes. The small size of VHHs permits their binding to epitopes (antigenic determinants in antigen proteins), e.g., "hidden epitopes" that are not accessible to whole antibodies of much larger size. As a therapeutic, a VHH is capable of efficient penetration and rapid clearance. Its single domain nature allows a VHH to be expressed in a cell without a requirement for supramolecular assembly, as is needed for whole antibodies which are typically tetrameric (two heavy chains and two light chains, having a MW of about 150 kDa). VHHs are also exhibit stability over time and have a longer half-life versus non-VHH antibody molecules, which comprise disulfide bonds that are susceptible to chemical reduction or enzymatic cleavage. Similar to immunoglobulins, VHHs may be modified post-translationally, e.g. to add chemical linkers, detectable moieties, such as fluorescent dyes, enzymes, substrates, chemiluminescent moieties, etc., or specific binding moieties, such as streptavidin, avidin, or biotin, etc., for use in the compositions and methods described herein.

An anti-TcdB VHH polypeptide that specifically binds to and neutralizes the activity of TcdB, may also be referred to as a "VHH-based neutralizing agent (VNA)" a "VNA polypeptide or protein" or a "VNA binding molecule."

As used herein, the terms "treat," treating," "treatment," and the like refer to reducing, diminishing, abating, alleviating, improving, or ameliorating a disorder and/or symptoms associated therewith. It will be appreciated that, although not precluded, treating a disorder or condition does not require that the disorder, condition or symptoms associated therewith be completely eliminated.

The term "multimeric binding molecule" refers in general to a multi-component protein or polypeptide containing two or more, same or different, VHH binding molecules, which are coupled or linked, e.g., via spacer sequences, to each other and/or other components of the molecule. Multimeric binding molecules may be dimeric, in that the binding molecule contains two VHH polypeptides that bind to toxin B of *C. difficile*. The anti-TcdB VHH polypeptides in a dimeric multimer may be the same or they may be different VHH polypeptides. The different anti-TcdB VHH polypeptides in a multimeric binding molecule may bind to different regions, portions, or epitopes (e.g., non-overlapping epitopes) of TcdB. Alternatively, the multimeric binding molecules may be heteromultimeric, in that the binding molecule contains more than one, e.g., two, three or four, different anti-TcdB VHH polypeptides such as described herein. In some embodiments, a heteromultimeric binding molecule contains two or more different anti-TcdB VHH polypeptides, each of which specifically binds to toxin B of *C. difficile*, e.g., at different or non-overlapping epitopes. In embodiments, dimeric multimers and heteromultimeric binding molecules comprising two or more anti-TcdB VHHs bind to and neutralize the activity of TcdB.

As used herein, the terms "prevent," "preventing," "prevention," "prophylactic treatment," "protection" and the like refer to reducing the probability of developing a disorder or condition in a subject, who does not have, but who is at risk of, is susceptible to, or disposed to (e.g., genetically disposed to), developing a disease, disorder, pathology, or condition.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, inclusive of the first and last values.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Although various features of the present disclosure can be described in the context of a single embodiment, the features can also be provided in separate embodiments, or in any suitable combination or combination of embodiments. The section headings used herein are for organizational purposes only and are not intended to be limiting to the subject matter described.

The features of the present disclosure are set forth with particularity in the appended claims. The features and advantages of the present disclosure will be better understood and obtained by reference to the detailed description infra, which sets forth illustrative embodiments, in which the principles of the disclosure are utilized, and in view of the accompanying drawings as described hereinbelow.

BRIEF DESCRIPTION OF THE DRAWINGS

In FIG. 1, the anti-TcdB VHHs JZS-C2, JZS-C10, and JZS-E4 displayed $IC_{50}$ TcdB-neutralization potency near 0.5 nM.

In FIG. 2, the anti-TcdB VHH JZS-E6 displayed $IC_{50}$ TcdB-neutralization potency close to 1 nM; JZS-F6 displayed $IC_{50}$ TcdB-neutralization potency near 0.5 nM; and JZS-H9 displayed $IC_{50}$ TcdB-neutralization potency about 15 nM.

In FIG. 3, the anti-TcdB VHH JZS-H4 displayed $IC_{50}$ TcdB-neutralization potency near 0.5 nM; JZT-F7 displayed $IC_{50}$ TcdB-neutralization potency close to 1 nM; and JZT-G9 displayed $IC_{50}$ TcdB-neutralization potency about 3 nM.

In FIG. 4, the anti-TcdB VHHs JZS-A2a and JZS-B2 displayed minimal TcdB-neutralizing activity, while JZS-B9 displayed $IC_{50}$ TcdB-neutralization potency close to 1 nM.

FIGS. 5A-5C disclose SEQ ID NOs: 123-131, 131-145 and 145-146, respectively, in order of appearance.

FIGS. 6A and 6B illustrate the sequence relatedness of representative anti-TcdB VHH polypeptides in a phylogram or phylogenetic tree (FIG. 6A) and in an amino acid sequence alignment (FIG. 6B). The amino acid sequences of the anti-TcdB VHH polypeptides described in Example 1 are presented in a phylogram (FIG. 6A), which demonstrates that, comparatively, these VHH polypeptides have approximately 78% to approximately 91% amino acid sequence identity. Despite amino acid sequence variations, each of these VHH polypeptides binds to *C. difficile* toxin B (TcdB) and in many cases neutralize the toxin activity. The sequence alignments of the anti-TcdB VHH polypeptides described in Example 1 and presented in FIG. 6B shows the areas of the Framework Regions (FR1-FR4) in the sequences. The relatedness of the FRs as described infra can also be visualized in FIG. 6B. FIG. 6B discloses SEQ ID NOs: 7, 15, 17, 5, 19, 13, 11, 3, 9, 23, 120 and 21, respectively, in order of appearance.

FIGS. 7A and 7B present amino acid sequence comparisons of camelid VHH polypeptides that specifically bind to *C. difficile* toxin B (TcdB). FIG. 7A shows the amino acid sequences and designates the CDR1, CDR2 and CDR3 regions of 15 individual anti-TcdB VHH polypeptides (109 amino acids in length) of a family of anti-TcdB VHHs generated as described herein. FIG. 7B shows the amino acid sequences and designates the CDR1, CDR2 and CDR3 regions of 5 of the most diverse members of the anti-TcdB VHH family. FIG. 7B illustrates that CDR diversity is selected for during the process of affinity maturation of a TcdB antigen binding VHH in the B cells of the immunized animal, yet all of the anti-TcdB VHH polypeptides that were generated specifically and detectably bound to TcdB. In the sequences of this anti-TcdB VHH polypeptide family, the FR regions (FR1, FR2, FR3 and FR4) are essentially invariant between and among the individual sequences, e.g., 97% or greater sequence identity. FIGS. 7A and 7B disclose SEQ ID NOs: 129, 124, 129, 129, 121, 147-150, 147, 151-153, 147, 154, 121, 148, 155, 124 and 153, respectively, in order of appearance.

DETAILED DESCRIPTION OF THE DISCLOSURE

Figure 1:
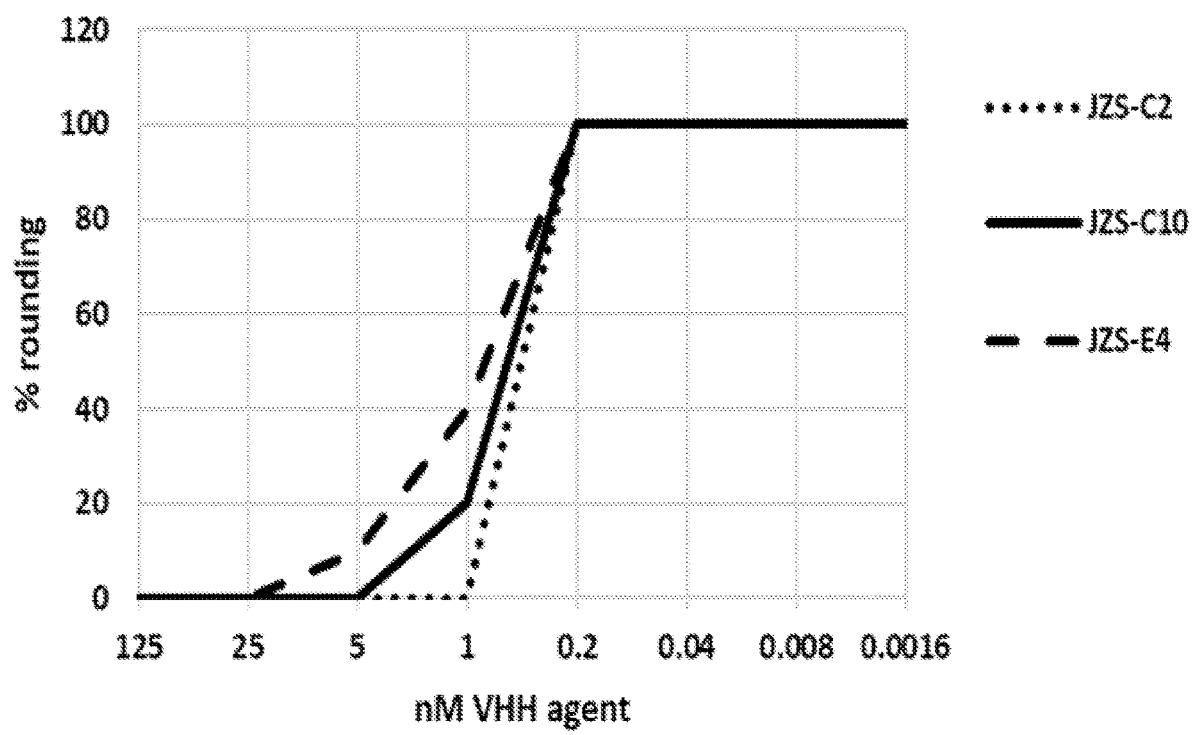
FIG. 1 presents a graph showing the results of neutralization studies performed to assess the neutralization activity of representative anti-TcdB VHH antibodies described herein. The assay was performed as described in Examples 4 and 5 infra.
Figure 2:
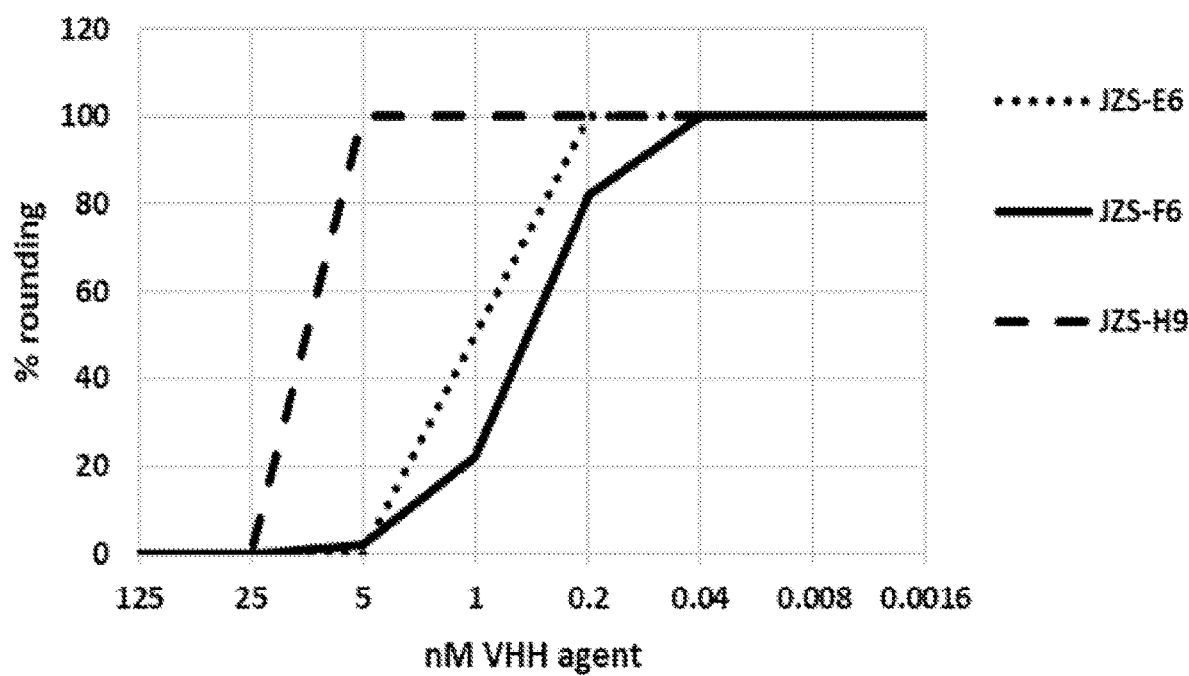
FIG. 2 presents a graph showing the results of neutralization studies performed to assess the neutralization activity of representative anti-TcdB VHH antibodies described herein. The assay was performed as described in Example 4 and 5 infra.
Figure 3:
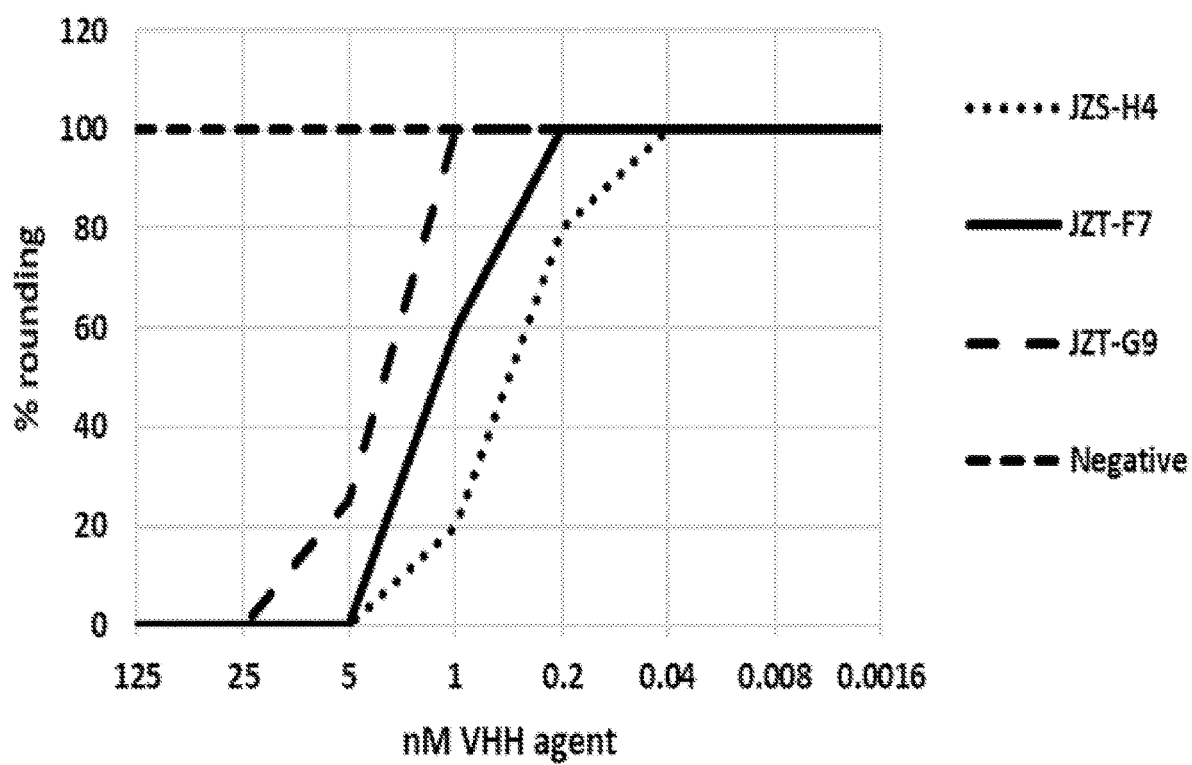
FIG. 3 presents a graph showing the results of neutralization studies performed to assess the neutralization activity of representative anti-TcdB VHH antibodies described herein. The assay was performed as described in Example 4 and 5 infra.
Figure 4:
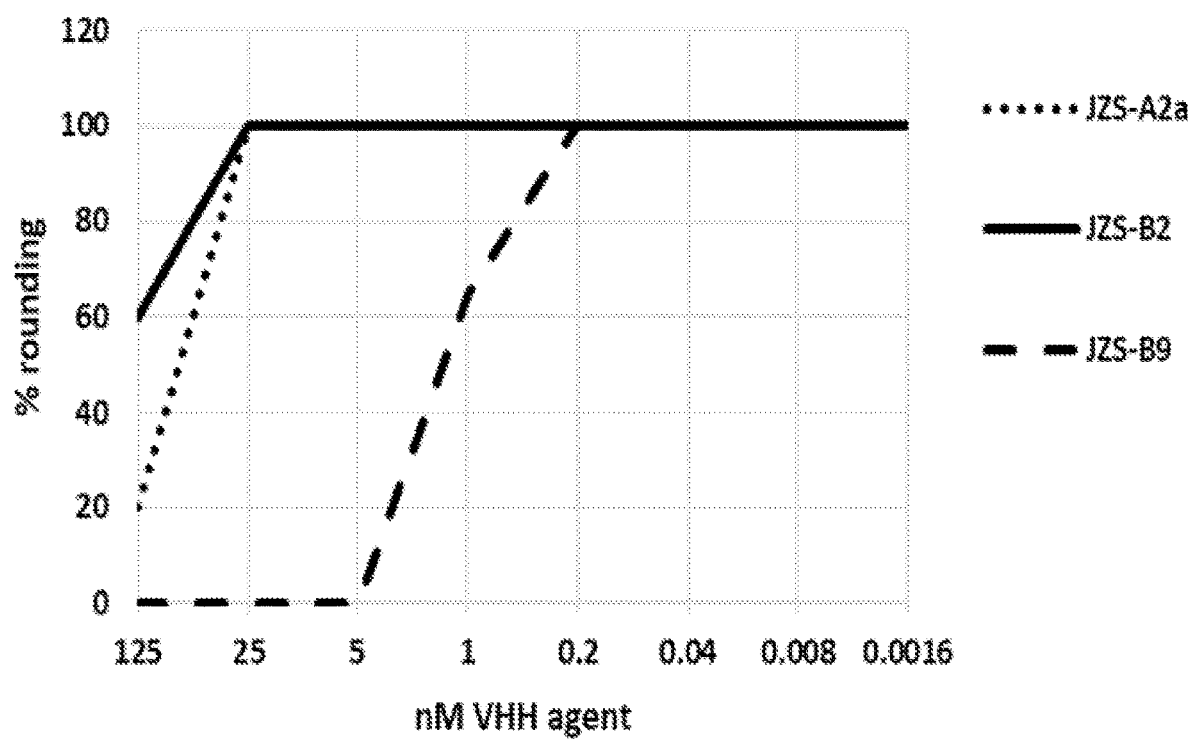
FIG. 4 presents a graph showing the results of neutralization studies performed to assess the neutralization activity of representative anti-TcdB VHH antibodies described herein. The assay was performed as described in Example 4 and 5 infra.

Described and featured herein are single domain antibody (sdAb) binding molecules, which are comprised of the heavy chain variable ($V_H$) region of heavy-chain-only antibodies (Abs), that specifically bind to the toxin B (TcdB) exotoxin virulence factor produced by pathogenic *Clostridium difficile* (*C. diff.*) microorganisms. Single-domain antibodies (camelid single-domain antibodies) are called VHHs as they derive from the $V_H$ region of a class of heavy-chain-only antibodies. The anti-toxin B (TcdB) VHHs were produced from immunized camelids (alpacas) and were selected for their ability to specifically bind to TcdB and, in most cases, to neutralize TcdB and the critical pathogenic functions caused by this toxin. The anti-TcdB VHHs as described herein are *C. diff.* toxin B binding polypeptides comprising hypervariable variable regions (CDRs) within framework (FR) regions. In general, the FRs of the anti-TcdB VHHs are typically highly similar in amino acid sequence, or differ by conservative amino acid substitutions at certain positions of the FR sequences, among different anti-TcdB VHHs or families of anti-TcdB VHHs. The anti-TcdB VHHs as described herein are stable over time and provide therapeutic efficacy in animal models. The anti-TcdB VHHs are employed as therapeutic antitoxin agents for the prevention and treatment of toxin B-mediated diseases, such as CDI and its symptoms, caused by *Clostridium difficile*. It will be understood that the terms "anti-TcdB VHH antibody," "anti-TcdB VHH polypeptide." "anti-TcdB VHH antibody polypeptide," and anti-TcdB VHH" are used interchangeably herein.

The presence of toxins produced by *C. difficile*, in particular, toxin B (TcdB), in the general circulation and locally in the gastrointestinal (GI) tract, causes serious illness in infected humans and other animals. *C. difficile* TcdB is considered to be the key exotoxin that causes CDI pathology. Antitoxins are therapeutic agents that prevent toxin infection or reduce further development of negative and adverse symptoms in patients who have been exposed to the toxin (a process referred to as "intoxication"). Antitoxins have historically included antisera obtained from large animals (e.g., sheep, horse, and pig) that were immunized with inactivated or non-functional toxin. More recently, antitoxin therapies have been developed using combinations of anti-toxin monoclonal antibodies, including yeast-displayed single-chain variable fragment antibodies generated from vaccinated humans or mice. See, e.g., Nowakowski et al. 2002. *Proc Natl Acad Sci USA*, 99: 11346-11350; Mukherjee et al. 2002. *Infect Immun*, 70: 612-619; Mohamed et al. 2005 *Infect Immun*, 73: 795-802; Walker, K. 2010 Interscience Conference on Antimicrobial Agents and Chemotherapy— 50th Annual Meeting—Research on Promising New Agents: Part 1. *IDrugs* 13: 743-745. Draw backs to the production and use of antisera and monoclonal antibodies as antitoxins include their difficulty to produce economically at scale. The production of such products typically requires long development times and frequently results in problematic quality control, shelf-life and safety issues.

In general, antitoxins function through two key mechanisms, namely, neutralization of toxin function and clearance of the toxin from the body. Toxin neutralization occurs through biochemical processes including inhibition of enzymatic activity and prevention of binding to cellular receptors. Antibody mediated serum clearance occurs subsequent to the binding of multiple antibodies to the target antigen (Daeron M. 1997 *Annu Rev Immunol*, 15: 203-234; Davies et al. 2002 *Arthritis Rheum*, 46: 1028-1038; Johansson et al. 1996 *Hepatology.* 24: 169-175; and Lovdal et al. 2000 *J Cell Sci*, 113 (Pt 18); 3255-3266).

The anti-TcdB VHHs or multimeric forms thereof as described herein are provided as beneficial therapeutic agents and/or antitoxins that bind to *C. difficile* toxin B. In some cases, the anti-TcdB VHHs or multimeric forms thereof both promote toxin B neutralization by rapidly and effectively blocking further toxin B activity and also accelerate clearance of toxin B from the system to eliminate future pathology. In addition, increased stability and longevity of the anti-TcdB VHHs or multimeric forms thereof in the GI tract where they can bind to and neutralize the effects of toxin B contribute to the advantages of these molecules as antitoxins that provide greater therapeutic efficacy as a treatment for CDI and other diseases and symptoms caused by *C. diff.* infection and intoxication.

In some embodiments, the binding activity and/or neutralizing activity of the anti-TcdB VHHs described herein, or multimeric forms thereof, in the absence of any epitope tag sequences are significantly effective such that the antitoxin function of these molecules obviates the need for an anti-tag antibody or clearing antibody.

VHHs, such as the anti-TcdB VHHs described herein, have a number of advantages over conventional antibodies and recombinant antibody domains, including (i) they are small monomeric proteins (14 kDa) that express and fold efficiently in recombinant hosts; (ii) they are more stable to extremes of pH and temperature compared with conventional antibodies; (iii) they typically bind conformational epitopes, and thus are more likely to neutralize target functions; and (iv) they are amenable to designed multimerization which often leads to higher potencies and a reduction in the risk that microorganisms (e.g., C'. diff) will develop resistance; and (v) they offer more therapeutic versatility, such as multispecificity, thus supporting their beneficial utility in treating enteric diseases.

The amino acid sequences of representative anti-TcdB VHH antibodies described herein are set forth in SEQ ID NOs: 1, 3, 5, 7, 9, 11, 13, 15, 17, 19, 21 and 23, and the corresponding polynucleotide sequences encoding each of the representative anti-TcdB VHH antibodies are set forth in SEQ ID NOs: 2, 4, 6, 8, 10, 12, 14, 16, 18, 20, 22 and 24 (Example 1). The binding regions of the anti-TcdB VHHs include CDRs (CDR1, CDR2 and CDR3) as set forth in the sequences in Example 1 and in Table 1 below. The CDR binding regions are positioned within framework (FR) regions of the VHH polypeptide, which do not vary substantially in sequence between discrete anti-TcdB VHHs and which provide a "structural scaffold" for the CDRs, which bind to TedB. By way of non-limiting example, the binding of CDRs within FRs to a target protein (antigen) may be via conformational binding or interaction, electrostatic binding interaction, hydrogen bonding, Van der Waals forces, or hydrophobic bonding, or combinations thereof, as would be appreciated by those having skill in the art.

Figure 7A:
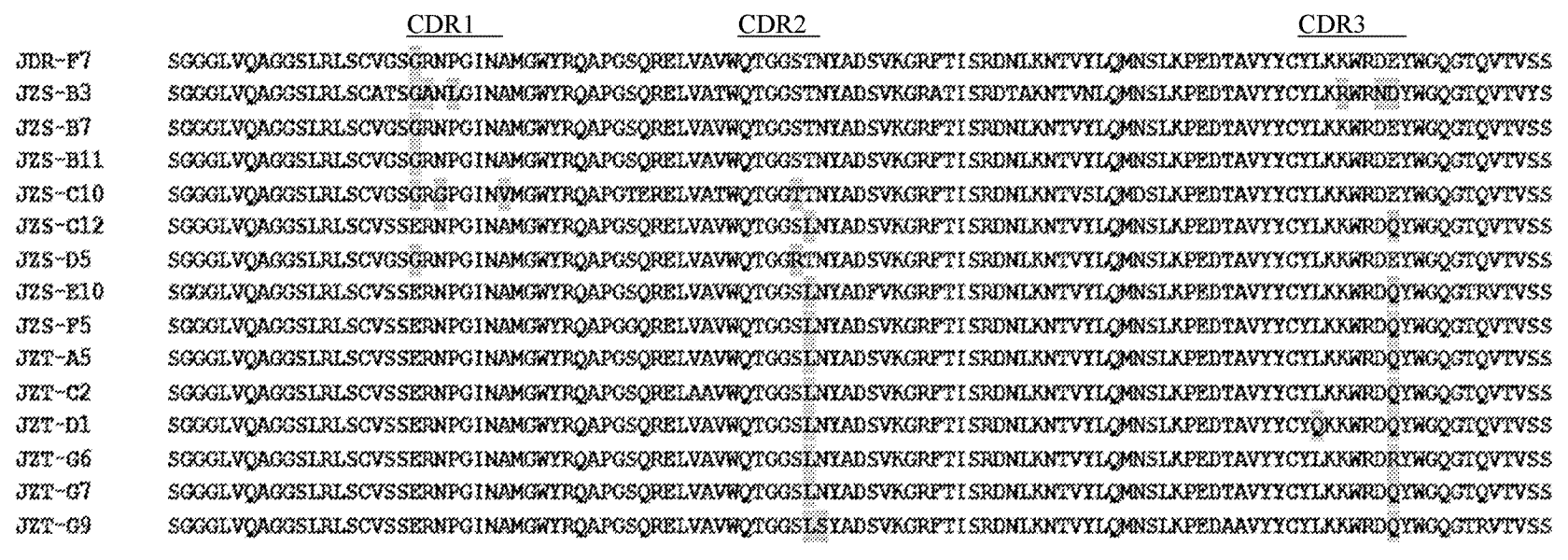

The CDRs of the anti-TcdB VHH polypeptides described herein may vary in amino acid sequence length. By way of nonlimiting example, CDR1 of the anti-TcdB VHH polypeptides as described herein may comprise from about 6 to about 12 amino acid residues; CDR2 may comprise from about 7 to about 12 amino acid residues; and CDR3 may comprise from about 8 to about 21 amino acid residues. It will be appreciated by one skilled in the art that number of amino acids that constitute a CDR is not necessarily precise. In some cases, an amino acid residue, or 2 or 3 amino acid residues, at one end or both ends of a given CDR may be considered as part of the CDR or as part of the neighboring FR region. The CDR regions of representative anti-TcdB VHH antibody polypeptides generated from camelid alpacas as described herein (Example 1) are presented in Table 1 below. In addition, FIG. 7A presents the amino acid sequences of a family of anti-TcdB VHH antibody polypeptides (JZS-C10 family) generated from a camelid alpaca immunized with TcdB as described herein. FIG. 7B presents the amino acid sequences of the most diverse members of anti-TcdB VHH antibody polypeptides in the JZS-C10 family, all of which bind to *C. difficile* toxin B (TcdB). The anti-TcdB VHH antibodies in FIG. 7B demonstrate the CDR diversity that is selected during affinity maturation of TedB binding polypeptides in the same animal. Despite such CDR diversity, the TcdB binding VHHs generated as described herein show detectable binding to TcdB. As observed from the sequence alignments shown in FIGS. 7A and 7B, in the context of the four VHH framework regions, which do not vary significantly in sequence among different anti-TcdB VHH polypeptides, the CDR1 sequences of the anti-TcdB VHH polypeptide members of the JZS-C10 family may vary by about 42% to about 58%: the CDR2 sequences of the anti-TcdB VHH polypeptide members of the JZS-C10 family may vary by about 27%; and the CDR3 sequences of the anti-TcdB VHH polypeptide members of the JZS-C10 family may vary by about 30% to about 40%. Notwithstanding some variation among the CDR sequences in the context of their framework regions, the anti-TcdB VHH polypeptides still bind very well to the TedB antigen.

TABLE 1

| VHH (anti-TcdB VHH) | CDR1 | CDR2 | CDR3 |
|---|---|---|---|
| JZS-A2a (XAF-1) | GSVYTF (SEQ ID NO: 25) | SGGTITK (SEQ ID NO: 26) | NAGDTIAQAMGTRRFPFDR (SEQ ID NO: 27) |
| JZS-B2 (XAF-4) | GTSFPRNY (SEQ ID NO: 28) | SHDGNVE (SEQ ID NO: 29) | KLVTLRRDEY (SEQ ID NO: 30) |
| JZS-B9 (XAF-5) | RFSLINYA (SEQ ID NO: 31) | TSGGATY (SEQ ID NO: 32) | AAGPYSRTLVSRWKVGDGMEY (SEQ ID NO: 33) |
| JZS-C2 (XAF-6) | GFTSNSYY (SEQ ID NO: 34) | SSSGGSPN (SEQ ID NO: 35) | AASKFPLTTMASNRYHY (SEQ ID NO: 36) |
| JZS-C10 (XAF-9) | GRGPGINV (SEQ ID NO: 37) | QTGGTTN (SEQ ID NO: 38) | YLKKWRDEY (SEQ ID NO: 39) |
| JZS-E4 (XAF-10) | GSSFSMNV (SEQ ID NO: 40) | RSDGITN (SEQ ID NO: 41) | FHGRARTGNNADLGS (SEQ ID NO: 25) |
| JZS-E6 (XAF-11) | GRLSERIFMIST (SEQ ID NO: 43) | SRLGRAN (SEQ ID NO: 44) | NLKPFVDNYR (SEQ ID NO: 25) |
| JZS-F6 (XAF-12) | GITFSNVA (SEQ ID NO: 46) | STGGSSTS (SEQ ID NO: 47) | VKGPKYSATIRRPE (SEQ ID NO: 25) |
| JZS-H4 (XAF-13) | GFNFSVQI (SEQ ID NO: 49) | STGGASKS (SEQ ID NO: 50) | SKGPRTWINSSPR (SEQ ID NO: 25) |
| JZS-H9 (XAF-14) | GTAFSLDT (SEQ ID NO: 52) | SSSGASN (SEQ ID NO: 53) | YRGRVRGVWPLDSGMMY (SEQ ID NO: 25) |
| JZT-F7 (XAG-1) | GSILSS (SEQ ID NO: 55) | SRTGATD (SEQ ID NO: 56) | NAGLGMGDPRRPGPW (SEQ ID NO: 57) |
| JZT-G9 (XAG-7) | ERNPGINA (SEQ ID NO: 58) | QTGGSLS (SEQ ID NO: 70) | YLKKWRDQY (SEQ ID NO: 60) |

In view of the representative anti-TcdB VHH amino acid sequences shown in FIGS. 7A and 7B, it will be appreciated by one skilled in the art that individual VHH polypeptides, (e.g., of about 109 amino acids in length and comprising 3 CDRs and 4 FR regions), which comprise at least about or equal to 85%, or 88%, or greater identity in amino acid sequence (e.g., about 12-15% variation in amino acid sequence) bind to TcdB antigen. In addition, the TcdB binding VHHs may further neutralize TcdB toxin. In an embodiment, at least about or equal to 85%, 86%, 87%, 88%, 89%, 90%, 91%, 92%, 93%, 94%, 95%, 96%, 97%, 98%, 99%, or 100% amino acid sequence identity is tolerated among the anti-TcdB VHHs without adversely affecting or eliminating binding of the VHH polypeptides to the TedB antigen. In an embodiment, such amino acid sequence variation among the anti-TcdB VHH polypeptides is tolerated in the CDRs of the VHH polypeptides without adversely affecting binding of the VHHs to TcdB. In a particular embodiment, the amino acid sequence variations between or among anti-TcdB VHHs encompass one or more conservative amino acid substitutions or changes in a VHH amino acid sequence. In an embodiment, the one or more conservative amino acid substitutions or changes in a VHH amino acid sequence occur in one or more CDR sequences of the VHH, in one or more FR sequences of the VHH, or in CDR and FR sequences of the VHH.

Figure 5A:
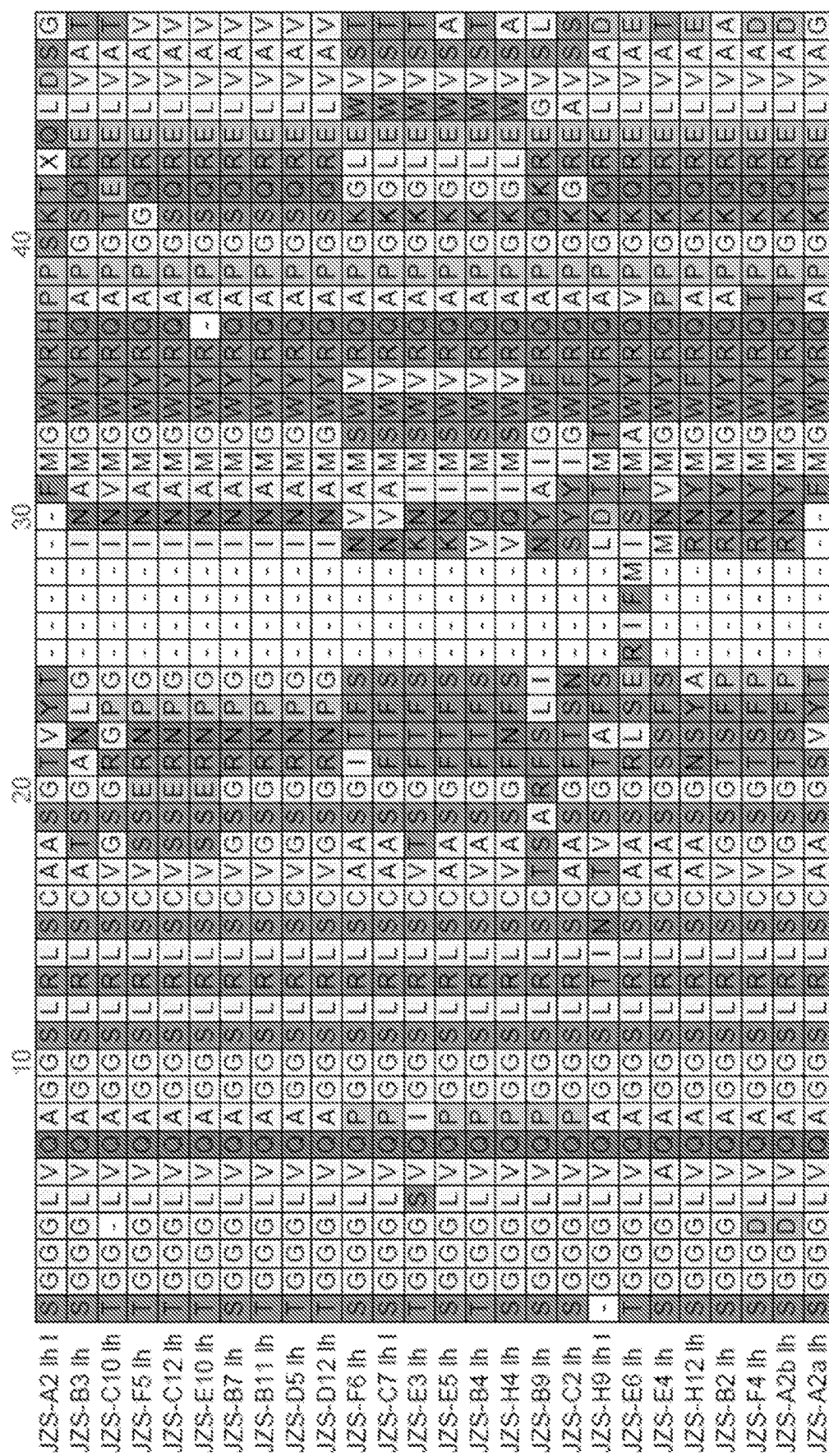
FIGS. 5A-5C provide a table in which *C. difficile* toxin B-binding, anti-TcdB VHH polypeptide sequences of 129 amino acids in length are aligned. In the sequences set forth in FIGS. 5A-5C, linearly from left to right, Framework 1 (FR1) encompasses approximately amino acid residues 5 to 20; complementarity determining region 1 (CDR1) encompasses approximately amino acid residues 21 to 34; Framework 2 (FR2) encompasses approximately amino acid residues 35 to 49/50; complementarity determining region 2 (CDR2) encompasses approximately amino acid residues 49/50 to 59/60; Framework 3 (FR3) encompasses approximately amino acid residues 59/60 to 95/96; complementarity determining region 3 (CDR3) encompasses approximately amino acid residues 95/96 to 117-119; and Framework 4 (FR4) encompasses approximately amino acid residues 117-119 to 129. It will be appreciated that the exact boundaries of the FRs and CDRs are often imprecise, as amino acid sequence variability is typically observed at and near the end of a FR and at and near the start of a hypervariable CDR. Anti-TcdB VHH polypeptide sequences described herein (Example 1) and in Tables 1 and 4, i.e., JZS-C10, JZS-F6, JZS-H4, JZS-B9, JZS-C2, JZS-H9, JZS-E6, JZS-E4, JZS-B2 and JZS-A2a, are representative among the sequences set forth in FIGS. 5A-5C.
Figure 5B:
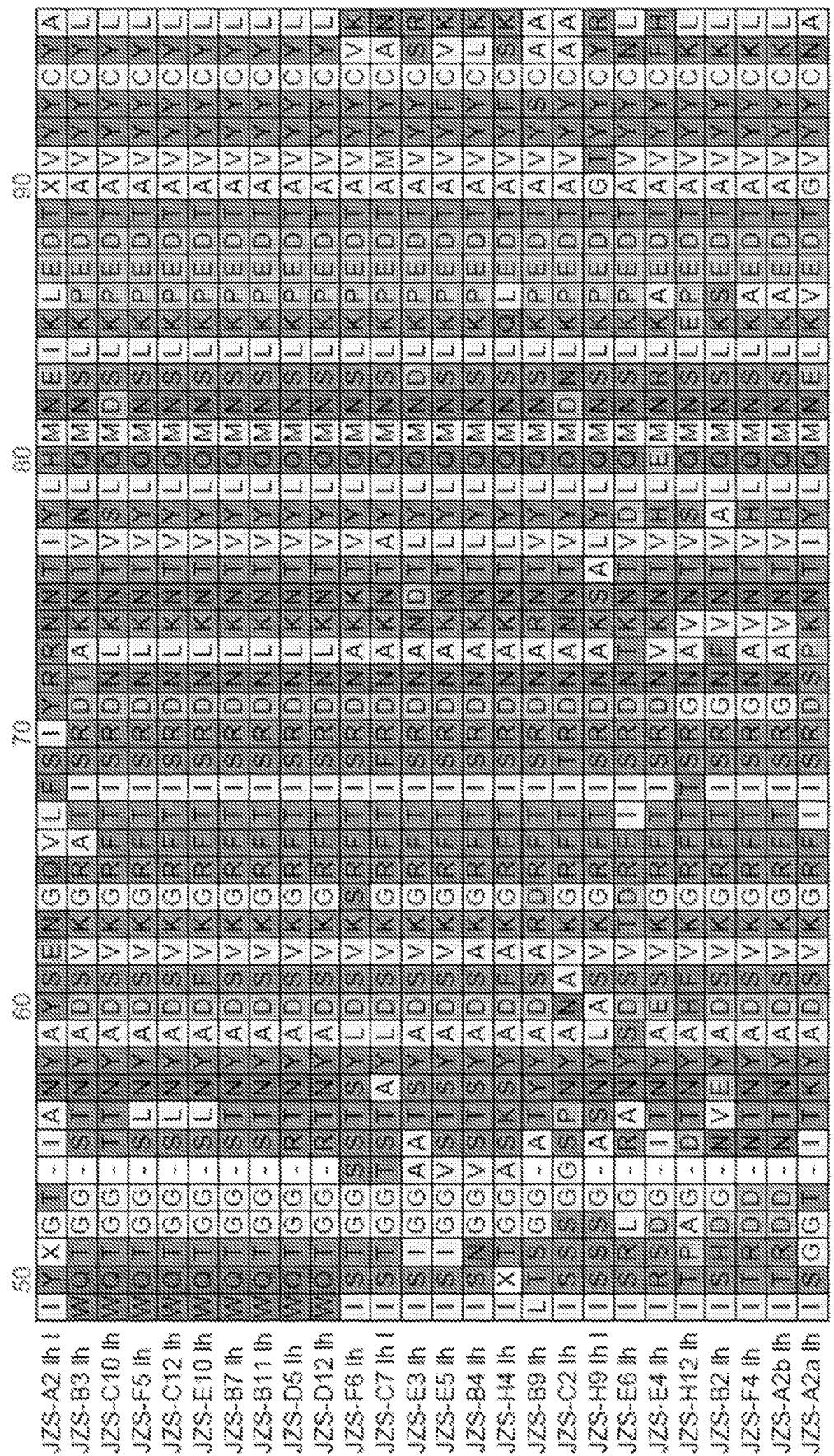
Figure 5C:
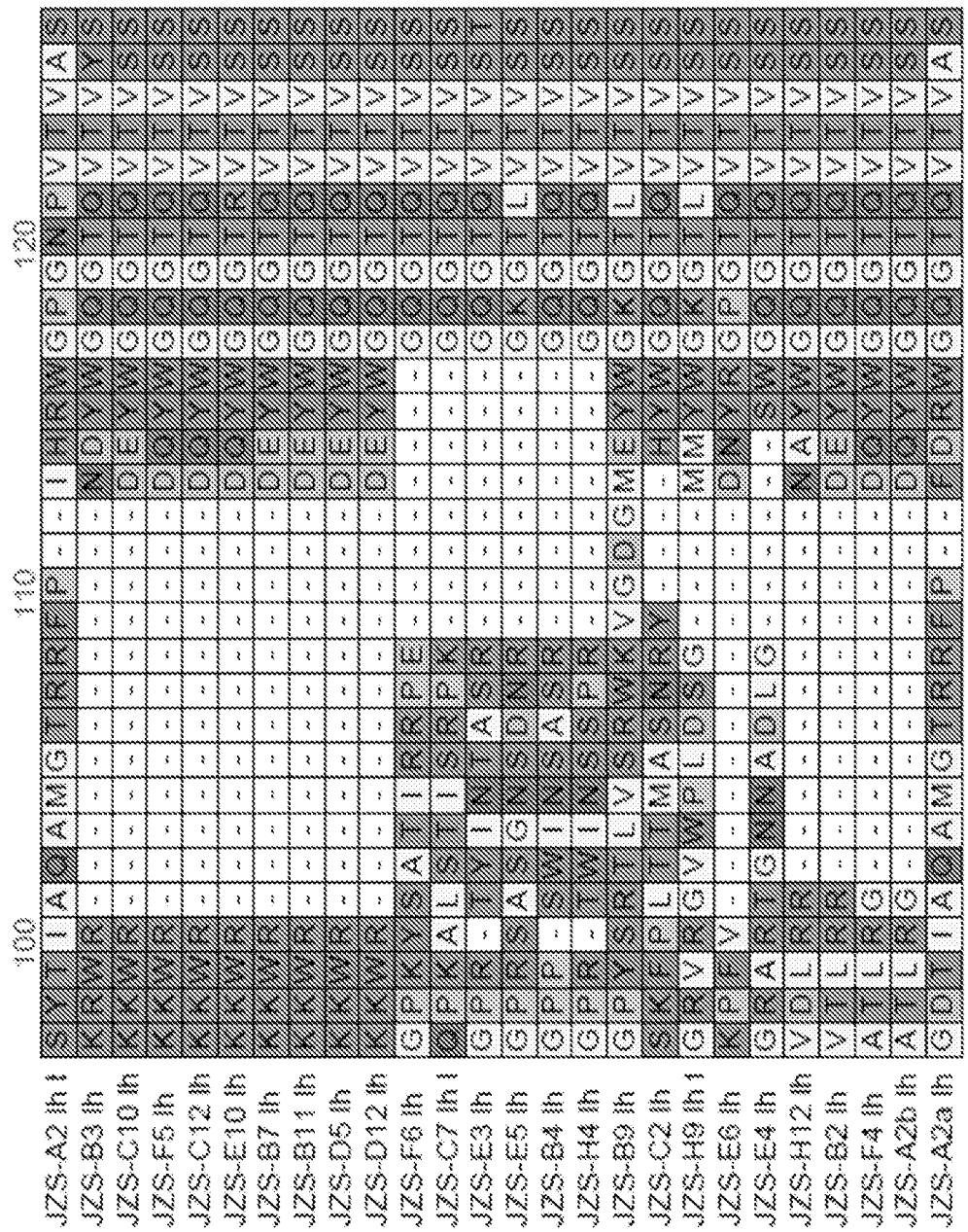

The three CDRs of the anti-TcdB VHH polypeptides are arranged or positioned in the context of four FR regions as follows: FR1-CDR1-FR2-CDR2-FR3-CDR3-FR4, in which FR1 to FR4 refer to the framework regions 1-4, respectively, and in which CDR1 to CDR3 refer to the complementarity determining regions 1-3, respectively. An alignment of anti-TcdB VHHs, all of which specifically bind to toxin B, demonstrates the extensive similarities among the sequences of each of the FRs (FR1, FR2, FR3 and FR4) found in the different toxin B binding VHH polypeptides (FIGS. 5A-5C; FIG. 6B; FIGS. 7A and 7B). Similar to the FRs in conventional antibody polypeptides, the respective FR regions (FR1, FR2, FR3 and FR4) of the anti-TcdB VHH polypeptides described herein are highly similar in sequence not only among different TcdB-binding VHHs but also among camelid VHH polypeptides that bind to other antigens. By way of example and as shown in Table 2, anti-TcdB VHH FR regions are highly similar in sequence to the respective FR1, FR2, FR3 and FR4 sequences of an unrelated camelid VHH polypeptide (see, L. S. Mitchell and L. J. Colwell, 2018, *Proteins*. 86(7); 697-706; A. M. Vattekatte et al., March, 2020, *Peer J.*, 6(8); e8408. DOI: 10.7717/peerj.8408), thus evidencing that the FR regions FR1, FR2, FR3 and FR4 of different VHHs do not vary significantly in sequence. In Table 2, the FRs of the VHH in the publication of Mitchell and Colwell is used as a reference sequence. Accordingly, provided are anti-TcdB VHH polypeptides comprising CDR1-3, in the structural context of FR1-4, that bind to and/or neutralize toxin B protein of *C. difficile*, or to suitable fragments of toxin B, as well as polypeptides that comprise or consist essentially of one or more of the anti-TcdB VHHs and/or toxin B binding fragments thereof.

Table 2 presents the amino acid sequences of the four framework regions, i.e., FR1, FR2, FR3 and FR4, respectively, of ten representative anti-TcdB VHH polypeptides described herein (i.e., JZS-C10, JZS-F6, JZS-H4, JZS-B9, JZS-C2, JZS-H9, JZS-E6, JZS-E4, JZS-B2 and JZS-A2a), relative to the FR1-FR4 of a VHH reference as reported in L. S. Mitchell and L. J. Colwell, 2018, Proteins. 86(7); 697-706, termed "Reference sequence" herein), thus demonstrating the substantial similarities among the structural FRs of camelid VHHs, independent of antigen binding specificity. In Table 2, the amino acid (AA) position numbering of the camelid VHH sequences containing the FRs begins at residue "Q" as #1, as shown in the amino acid sequences of the anti-TcdB VHH polypeptides presented in Example 1. It will be appreciated that in the sequence alignments presented in FIGS. 5A-5C, the amino acid residues #1 and #2, etc., shown in the figure, i.e., "E" and "S/T, etc.," correspond to amino acid positions 6 and 7, etc., respectively, of the sequences presented in Example 1.

TABLE 2

FR1

| | | Position # | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| Reference Sequence | AA | Q | V | Q | L | Q/V | E | S | G | G | G | L/S | V | Q | A/P | G |
| Anti-TcdBVHHs | AA | | | | | | E | S/T | G | G | G | L | V | Q | A/P | G |

FR1

| | | Position # | | | | | | | | | |
|---|---|---|---|---|---|---|---|---|---|---|---|
| | | 16 | 17 | 18 | 19 | 20 | 21 | 22 | 23 | 24 | 25 |
| Reference Sequence | AA | G | S | L | R | L | S | C | A | A | S |
| Anti-TcdBVHHs | AA | G | S | L | R/T | L/I | S/N | C | A/V/T | A/G/V/S | S/A |

TABLE 2-continued

FR2

| | | Position # | | | | | | | | | | | | |
|---|---|---|---|---|---|---|---|---|---|---|---|---|---|---|
| | | 36 | 37 | 38 | 39 | 40 | 41 | 42 | 43 | 44 | 45 | 46 | 47 | 48 | 49 |
| Reference Sequence | AA | W | F/Y/V | R | Q | A | P | G | K | E/C/G | R/L | E | F/G/L/W | V | A/S/T |
| Anti-TcdBVHHs | AA | W | F/Y/V | R | Q | A/P | P | G | K/S/Q | Q/G/E/K/T | R/L | E | L/W/G | V/D | A/S |

FR3

| | | Position # | | | | | | | | |
|---|---|---|---|---|---|---|---|---|---|---|
| | | 60 | 61 | 62 | 63 | 64 | 65 | 66 | 67 | 68 | 69 |
| Reference Sequence | AA | Y | A/Q/T/V | D/E | S | V/A | K | G | R | F | T/A |
| Anti-TcdBVHHs | AA | Y | A/L/S | D/N/A/E | S/F/A | V/A | K/R/T | G/S/D | R | F | T/I |

FR3

| | | | Position # | | | | | | | |
|---|---|---|---|---|---|---|---|---|---|---|
| | | | 70 | 71 | 72 | 73 | 74 | 75 | 76 | 77 | 78 |
| Reference Sequence | AA | I/V | S | R/Q | D | N/K | A | K/A | N | T |
| Anti-TcdBVHHs | AA | I | S/T | R | D/G | N/S | A/L/T/V/F/P | K/N/V | N/K//S | T/A |

FR3

| | | Position # | | | | | | | | | | | | | | | | |
|---|---|---|---|---|---|---|---|---|---|---|---|---|---|---|---|---|---|---|
| | | 79 | 80 | 81 | 82 | 83 | 84 | 85 | 86 | 87 | 88 | 89 | 90 | 91 | 92 | 93 | 94 | 95 | 96 |
| Reference Sequence | AA | V/L/M | Y | L | Q | M | N/D | S/N | L | K/R | P | E/D | D | T | A/G | V/I/T/M | Y | Y | C |
| Anti-TcdBVHHs | AA | V/L | Y/H/D/S | L | Q/E | M | N/D | S/N/R/E | L | K/Q | P/L/S/V | E | D | T | A/G | V/T | Y | Y/F/S | C |

FR4

| | | Position # | | | | | | | | | |
|---|---|---|---|---|---|---|---|---|---|---|---|
| | | 117 | 118 | 119 | 120 | 121 | 122 | 123 | 124 | 125 | 126 | 127 |
| Reference Sequence | AA | W | G | Q | G | T | Q | V | T | V | S | S |
| Anti-TcdBVHHVHHs | AA | W/R | G | Q/K/P | G | T | Q/L | V | T | V | S/A | S |

In embodiments, in cases in which a FR (or CDR) amino acid residue in a VHH polypeptide may be one of several alternative amino acid residues, the alternative amino acid residues will frequently share similar characteristics or properties, e.g., hydrophobicity, polarity, and/or charge. A conservative replacement (also called a conservative substitution) is an amino acid replacement or substitution in a polypeptide or region thereof that changes a given amino acid residue to a different amino acid residue with similar biochemical properties, such as charge, hydrophobicity, and/or size. By way of non-limiting example, the below Table 3 presents amino acids and their 1-letter codes categorized into six main classes based on their structure and the general chemical characteristics of their side chains (R groups).

TABLE 3

| Amino Acids | Class |
|---|---|
| Glycine (G), Alanine (A), Valine (V), Leucine (L), Isoleucine (I) | Aliphatic |
| Serine (S), Cysteine (C), Selenocysteine (U), Threonine (T), Methionine (M) | Hydroxyl or sulfur/selenium containing |
| Proline (P) | Cyclic |
| Phenylalanine (F), Tyrosine (Y), Tryptophan (W) | Aromatic |
| Histidine (H), Lysine (K), Arginine (R) | Basic |
| Aspartate (D), Glutamate (E), Asparagine (N), Glutamine (Q) | Acidic and amides thereof |

In an embodiment, amino acid sequence substitutions or changes in an anti-TcdB VHH polypeptide relative to another anti-TcdB VHH polypeptide comprise conservative amino acid substitutions or changes such that a given amino acid residue is substituted with or replaced by a different amino acid residue with similar biochemical properties, such as charge, hydrophobicity, and/or size. In an embodiment, sequence variation between or among anti-TcdB VHH polypeptides results from one or more conservative amino acid changes and account for the percent sequence variation, e.g., 85%, 86%, 87%, 88%, 90%, 91%, 92%, 93%, 94%, 95%, 96%, 97%, 98%, or 99% sequence variation.

In some embodiments, the VHHs as described herein are humanized using methods and techniques practiced by those having skill in the art. (See. e.g., U.S. Pat. Nos. 8,975,382 and 10,550,174, the contents of which are incorporated by reference herein).

The anti-TcdB VHH antibodies described herein have widespread application as therapeutics in the treatment of disease and pathologies resulting from infection by *C. difficile* pathogenic bacteria and the toxins, particularly, toxin B produced by these pathogens. The described anti-TcdB VHHs described herein are particularly useful for binding to and eradicating the disease-causing the TcdB target protein that intoxicates a subject after *C. difficile* infection and causes debilitating disease, and even death. In embodiments, various embodiments encompass polynucleotides (nucleic acid sequences) that encode the operably linked modular components that constitute the described anti-TcdB VHHs. In embodiments, the anti-TcdB VHHs are recombinantly produced. In embodiments, the anti-TcdB VHHs encompass the proteins (polypeptides) encoded by the polynucleotides. In embodiments, the polynucleotide is DNA. cDNA, RNA. mRNA, and the like. In an embodiment, the anti-TedB VHHs may be humanized or codon-optimized using methods practiced by those having skill in the art.

Polynucleotides Encoding VHHs that Bind to *C. difficile* Toxin B (TcdB)

In some cases, more than one anti-TcdB-binding VHH antibody (i.e., anti-TedB VHH) is coupled or linked (e.g., covalently linked) to other sequences, e.g., a leader amino acid sequence, one or more spacer (flexible spacer) amino acid sequences, or one or more epitope tag amino acid sequences, to produce a multimeric VHH binding molecule containing two or more, e.g., three, four, five, or six. VHHs linked together. In an embodiment, a polynucleotide molecule, such as a recombinant or isolated polynucleotide molecule, encodes a single anti-TcdB VHH or more than one anti-TcdB VHH linked together to form a multimer (i.e., a multimeric anti-TcdB VHH binding molecule). In an embodiment, the polynucleotide encodes a fragment or portion of the anti-TcdB VHH or multimeric anti-TcdB VHH binding molecule, in particular, a fragment or portion that maintains TcdB binding function or TedB binding and neutralizing function. The polynucleotide sequences encoding representative anti-TcdB VHH antibodies as described herein are set forth in SEQ ID NOs: 2, 4, 6, 8, 10, 12, 14, 16, 18, 20, 22 and 24 (Example 1).

In an embodiment, an anti-TcdB VHH can be humanized. i.e., modified to increase its similarity to antibodies or antibody variants produced naturally in humans, using techniques known and practiced in the art. Briefly and by way of nonlimiting example, a humanized antibody can be generated by inserting the appropriate CDR coding sequences (e.g., 'donor' sequences that are responsible for the desired binding properties) into a human antibody "scaffold" (e.g., 'acceptor' sequences) comprising essentially invariant framework region (FR) sequences (FRs). In embodiments, the CDRs of the anti-TcdB VHH antibodies described herein may be inserted into FRs, which provide the structural scaffold that allows the CDRs to bind to, and in certain cases, to neutralize, toxin B. Recombinant DNA methods using an appropriate vector and expression in mammalian cells are employed and routinely practiced in the art to achieve the production of recombinant humanized antibodies.

In an embodiment, the polynucleotide encodes a TcdB binding and neutralizing function, or a functional binding portion thereof, that includes an epitope tag. In embodiments, antibody fragments, microproteins, darpins, anticalins, peptide mimetic molecules, aptamers, synthetic molecules, etc. can be linked to the multimeric anti-TcdB VHH binding molecule. In embodiments, a multimeric anti-TcdB VHH binding molecule may contain two of the same anti-TcdB VHHs, e.g., a dimeric form, or two different anti-TcdB VHHs described herein. In other embodiments, a multimeric anti-TcdB VHH binding molecule may contain more than two anti-TcdB VHHs in combination, e.g., a combination of three, four, or five, etc, anti-TcdB VHHs linked together. In an embodiment, the anti-TcdB VHH components of a multimeric anti-TcdB VHH binding molecule may be linked covalently.

In an embodiment, an anti-TcdB VHH can be modified, for example, by attachment (e.g., directly or indirectly via a linker or spacer) to another anti-TcdB VHH. In some embodiments, anti-TcdB VHH is attached or genetically (recombinantly) fused to another anti-TcdB VHH. Accordingly, a polynucleotide (e.g., DNA) that encodes one anti-TcdB VHH is joined (in reading frame) with the polynucleotide encoding a second anti-TcdB VHH, and so on. In certain embodiments, additional amino acids are encoded within the polynucleotide between the anti-TcdB VHHs so as to produce an unstructured region (e.g., a flexible spacer) that separates the anti-TcdB VHHs, e.g., to better promote independent folding of each anti-TcdB VHH antibody into its active or functional conformation or shape. Commercially available techniques for fusing proteins (or their encoding polynucleotides) may be employed to recombinantly join or couple the anti-TedB VHHs into multimeric anti-TcdB VHHs containing two or more of the same or different anti-TcdB VHHs as described herein.

Polynucleotide sequences encoding the anti-TcdB VHHs or multimeric forms thereof as described herein can be recombinantly expressed and the resulting encoded anti-TedB VHH antibody molecules can be produced at high levels and isolated and/or purified. In an embodiment, the recombinant anti-TcdB VHHs or multimeric forms thereof are produced in soluble form. In an embodiment, a recombinantly produced anti-TcdB VHH is dimeric, such that two anti-TcdB VHHs, same or different, are joined or linked together. In an embodiment, a recombinantly produced anti-TcdB VHH is multimeric, e.g., a tetramer, which contains four anti-TcdB VHH antibodies, the same or a combination of different anti-TcdB VHHs, joined together. By way of example, a tetramer may contain four of the same anti-TcdB VHHs joined together, or a combination of four different anti-TedB VHHs, or two pairs of the same anti-TcdB VHHs, joined together. In an embodiment, the anti-TcdB VHH or multimeric forms thereof are contained in pharmaceutically acceptable compositions for use in treating CDI and/or neutralizing toxin B produced by *C. diff*.

The compositions and methods described herein in various embodiments include an isolated polynucleotide sequence or an isolated polynucleotide molecule that encodes an anti-TcdB VHH or multimeric form thereof. Accordingly, in some embodiments, the isolated polynucleotide sequence or isolated polynucleotide molecule comprises or consists of a polynucleotide sequence that encodes a polypeptide molecule (anti-TcdB VHH) having an amino acid sequence of SEQ ID NOS: 1, 3, 5, 7, 9, 11, 13, 15, 17, 19, 21, 23, or a functional portion thereof, as described herein. In some embodiments, the isolated polynucleotide sequence or isolated polynucleotide molecule comprises or consists of a polynucleotide sequence of SEQ ID NOS: 2, 4, 6, 8, 10, 12, 14, 16, 18, 20, 22, or 24. In an embodiment, a composition comprises a combination of the isolated polynucleotide sequences or isolated polynucleotide molecules as described herein.

Also encompassed by the aspects and embodiments described herein are polynucleotide sequences, DNA or RNA, which are substantially complementary to the DNA sequences encoding the polypeptides described herein, and which specifically hybridize with these DNA sequences under conditions of stringency known to those of skill in the art. As referred to herein, substantially complementary means that the nucleotide sequence of the polynucleotide need not reflect the exact sequence of the original encoding sequences, but must be sufficiently similar in sequence to permit hybridization with a nucleic acid sequence under high stringency conditions. For example, non-complementary bases can be interspersed in a nucleotide sequence, or the sequences can be longer or shorter than the polynucleotide sequence, provided that the sequence has a sufficient number of bases complementary to the sequence to allow hybridization thereto. Conditions for stringency are described, e.g., in Ausubel, F. M., et al., *Current Protocols in Molecular Biology*, (Current Protocol, 1994), and Brown, et al., *Nature,* 366:575 (1993); and further defined in conjunction with certain assays.

Vectors, plasmids, bacteria, viruses, or genetically modified *Spirulina* algal organisms containing one or more of the polynucleotide molecules encoding the anti-TedB VHH amino acid sequence of SEQ ID NO: 1, 3, 5, 7, 9, 11, 13, 15, 17, 19, 21, 23, or a functional portion thereof, are provided. Vectors, plasmids, bacteria, viruses, or genetically modified *Spirulina* algal organisms containing one or more of the polynucleotide molecules of SEQ ID NOS: 2, 4, 6, 8, 10, 12, 14, 16, 18, 20, 22, or 24 are also provided. Suitable vectors for use in eukaryotic and prokaryotic cells are known in the art and are commercially available or readily prepared by the skilled practitioner in the art. Additional vectors can also be found, for example, in Ausubel, F. M., et al., Ibid, and in Sambrook et al., "Molecular Cloning: A Laboratory Manual," 2nd ED. (1989), and other editions.

Any of a variety of expression vectors (prokaryotic or eukaryotic) known to and used by those of ordinary skill in the art may be employed to express recombinant polypeptides described herein. Expression can be achieved in any appropriate host cell that has been transformed or transfected with an expression vector containing a polynucleotide (DNA) molecule that encodes a recombinant polypeptide. Suitable host cells include prokaryotes, yeast and higher eukaryotic cells. By way of example, the host cells employed include, without limitation, *E. coli*, yeast, insect cells, or a mammalian cell line such as COS or CHO. The DNA sequences expressed in this manner can encode any of the polypeptides described herein, including variants thereof.

Uses of plasmids, vectors or viruses containing polynucleotides encoding the anti-TcdB VHHs or multimeric forms thereof as described herein include generation of mRNA or protein in vitro or in vivo. In related embodiments, host cells transformed with the plasmids, vectors, or viruses are provided, as described above. Nucleic acid molecules can be inserted into a construct (such as a prokaryotic expression plasmid, a eukaryotic expression vector, or a viral vector construct, which can, optionally, replicate and/or integrate into a recombinant host cell by known methods. The host cell can be a eukaryote or prokaryote and can include, for example and without limitation, yeast (such as *Pichia pastoris* or *Saccharomyces cerevisiae*), bacteria (such as *E. coli*, or *Bacillus subtilis*), animal cells or tissue (CHO or COS cells), insect Sf) cells (such as baculoviruses infected SF9) cells), or mammalian cells (somatic or embryonic cells, Human Embryonic Kidney (HEK) cells, Chinese hamster ovary (CHO) cells, HeLa cells, human 293 cells and monkey COS-7 cells). Suitable host cells also include a mammalian cell, a bacterial cell, a yeast cell, an insect cell, a plant cell, or a *Spirulina* algal cell.

An anti-TcdB VHH-encoding polynucleotide molecule can be incorporated or inserted into the host cell by known methods. Examples of suitable methods for transfecting or transforming host cells include, without limitation, calcium phosphate precipitation, electroporation, microinjection, infection, lipofection and direct uptake. "Transformation" or "transfection" as appreciated by the skilled practitioner refers to the acquisition of new or altered genetic features by the incorporation of additional nucleic acids, e.g., DNA, into cellular DNA. "Expression" of the genetic information of a host cell is a term of art which refers to the directed transcription of DNA to generate RNA that is, in turn, translated into a polypeptide (anti-TcdB VHH antibody). Procedures for preparing recombinant host cells and incorporating nucleic acids are described in more detail in Sambrook et al., "*Molecular Cloning: A Laboratory Manual,*" Second Edition (1989) and Ausubel, et al. "*Current Protocols in Molecular Biology*," (1992), and later editions, for example.

A transfected or transformed host cell is maintained under suitable conditions for expression and recovery of the polypeptides described herein. In certain embodiments, the cells are maintained in a suitable buffer and/or growth medium or nutrient source for growth of the cells and expression (and secretion) of the gene product(s) into the growth medium. The type of growth medium is not critical to the aspects and embodiments herein and is generally known to those skilled in the art, such as, for example, growth medium and nutrient sources that include sources of carbon, nitrogen and sulfur. Examples include Luria-Bertani (LB) broth, Superbroth, Dulbecco's Modified Eagles Media (DMEM), RPMI-1640, M199 and Grace's insect media. The growth medium can contain a buffering agent, as commonly used in the art. The pH of the buffered growth medium may be selected and is generally a pH that is tolerated by, or optimal for, growth of the host cell, which is maintained under a suitable temperature and atmosphere.

In another aspect, an RNA polynucleotide, in particular, mRNA, encodes the anti-TcdB VHHs or multimeric forms thereof as described herein. mRNA encoding the anti-TcdB VHHs or multimeric forms thereof may contain a 5' cap structure, a 5' UTR, an open reading frame, a 3' UTR and poly-A sequence followed by a C30 stretch and a histone stem loop sequence (Thess, A. et al., 2015, *Mol Ther,* 23(9); 1456-1464; Thran, M. et al., 2017, *EMBO Molecular Medicine*, DOI: 10.15252/emmm.201707678). Sequences may be codon-optimized for human use using techniques and protocols known and used by those skilled in the art. In an embodiment, the mRNA sequences do not include chemically modified bases. mRNAs encoding the anti-TcdB VHHs or multimeric forms thereof as described herein may be capped enzymatically or further polyadenylated for in vivo studies/use.

Expression of proteins, which normally have a shortened serum half-life, by encoding mRNA, particularly sequence optimized, unmodified mRNA, advantageously prolongs the bioavailability of these proteins for in vivo activity. (see, e.g., K. Kariko et al, 2012, *Mol. Ther.,* 20:948-953; Thess, A. et al., 2015, Mol Ther, 23(9); 1456-1464;). Accordingly, anti-TcdB VHHs or multimeric forms thereof with an estimated serum half-life of 1-2 days are likely to benefit from being encoded by mRNA. Of note, the half-lives of neutralizing VHH protein serum titers at one to three days after treatment were estimated to be, on average, 1.5-fold higher than from day three onward, even without target-specific mRNA optimization. (Mukherjee et al., 2014, *PLOS ONE,* 9e106422). In general, one to three days after treatment, both mRNA and protein half-lives contribute to the kinetics of serum titers, while after day three forward, the kinetics is almost exclusively determined by the properties of the expressed protein.

Multimeric Forms of the Anti-TcdB VHHs

Multimeric forms of the anti-TcdB VHH antibodies described herein are encompassed by the present disclosure. Such multimeric anti-TcdB VHHs contain more than one anti-TcdB VHH antibody that binds to TcdB. In an embodiment, a multimer of anti-TcdB VHH antibodies contains two anti-TcdB VHHs, same or different, that bind to TcdB. Such a multimeric form of the anti-TcdB VHH molecules constitutes a dimeric multimer. In an embodiment, the dimeric multimer comprises two of the same anti-TcdB VHH antibodies coupled using a flexible linker. In an embodiment, the dimeric multimer comprises two, different anti-TcdB VHH antibodies coupled using a flexible linker. In an embodiment, the two, different anti-TcdB VHH antibodies bind to different, nonoverlapping epitopes of TcdB.

In another embodiment, a multimer of anti-TcdB VHH antibodies contains more than two (e.g., three, four, five, six, etc.) anti-TcdB VHHs, same or different, that bind to TcdB. Such a multimeric form of the anti-TcdB VHH molecules may comprise three or more of the same anti-TcdB VHH antibodies coupled using flexible linkers. In an embodiment, the anti-TcdB VHH multimer comprises a combination or mixture of the anti-TcdB VHH antibodies described herein coupled using a flexible linker. In some cases, the multimeric form of the anti-TcdB VHH antibodies may contain more than one of the same anti-TcdB VHH antibody and/or different, or different combinations of, anti-TcdB VHH antibodies coupled using flexible linker or spacer peptides. Nonlimiting examples of flexible linking amino acid sequences include amino acid sequence GGGGS (SEQ ID NO: 63); GGGGSGGGGSGGGGS (SEQ ID NO: 64), or a functional portion thereof: EPKTPKPQGGGGSGGGGSGGGGSQGVQSQVQLVE (SEQ ID NO: 65); or EPKTPKPQ (SEQ ID NO: 66). In certain embodiments, the anti-TcdB VHH amino acid sequences described herein are coupled to epitope tag amino acid sequences as described infra, or to other sequences. In another embodiment, a dimerization agent that complexes peptide fragments each containing at least about 5 to 25 amino acids, 25 to 50 amino acids, 50 to 100 amino acids, 100 to 150 amino acids, and 150 amino acids to about 200 amino acids may be used. Multimerization agents and methods of using the agents for forming multimeric binding proteins can be found, for example, in U.S. Pat. Nos. 9,023,352, 8,349,326 and 7,763.445, each of which is incorporated by reference herein in its entirety.

In embodiments, the multimeric forms of the anti-TcdB VHH antibodies described herein both bind to TcdB and neutralize its activity.

Epitope Tags and Antibodies Thereto

In certain embodiments, an anti-TcdB VHH antibody, or a dimeric or multimeric form thereof, includes a single epitope tag (single tag sequence) or multiple tags (multiple tag sequences), to which anti-tag antibodies specifically bind. For example, a multimeric VHH may include at least one, or two or more, epitope tags in the molecule. Such epitope tags, which are specifically bindable by the anti-epitope tag antibodies, are useful in detecting VHHs bound to toxin antigens. In addition, such tags may facilitate clearance of VHHs bound to toxin antigens following binding of the tags by anti-tag antibody. By way of nonlimiting example, a tag may constitute an O-tag epitope of amino acid sequence DELGPRLMGK (SEQ ID NO: 61) or an E-tag epitope of amino acid sequence GAPVPYPDPLEPR (SEQ ID NO: 62). The epitope tags may be placed at the amino terminus, carboxy terminus, or internally within a multimeric VHH molecule. Such tags and/or anti-tag antibodies are described for example, in (U.S. Pat. Nos. 8,349,326; 9,023,352, WO 2019/094095A1) and U.S. Pat. Nos. 7,943,345; 8,114,634 and 8,865,871), the contents of which are incorporated herein by reference in their entireties. An example of an anti-O tag monoclonal antibody (IgG1) suitable for binding the DELGPRLMGK (SEQ ID NO: 61) tag sequence is described in WO 2019/094095A1, the contents of which are fully incorporated by reference. By way of illustrative example, peroxidase labeled antibodies that bind the anti-O-tag antibody may be used to detect these anti-tag antibodies in assays in which samples are incubated with goat anti-O-tag-HRP conjugated antibody (Bethyl labs) diluted 1:5000 in blocking solution for 1 hour at RT with rocking and were washed as above before adding TMB microwell peroxidase substrate (KPL) to develop (incubated for 10-40 min). Development was stopped with 1M $H_2SO_4$ and the plates were read at 450 nm on an ELx808 Ultra Microplate Reader (Bio-Tek instruments), (Mukherjee, J. et al., 2012, *PloS ONE* 7; e29941).

In some cases, an albumin binding peptide (DICL-PRWGCLWED (SEQ ID NO: 71)), may be included at the 3' end of an anti-TcdB VHH antibody or multimeric form thereof. In certain embodiments, the presence of an epitope tag operably linked, coupled, or fused to a VHH antibody or multimeric form thereof, wherein the tag is bound by an anti-epitope tag antibody, induces clearance of the toxin-bound VHH molecule from the body. In an embodiment, the binding of one or more epitope tags in an anti-TcdB VHH molecule by anti-epitope tag antibody(ies) may synergistically induce clearance of TcdB from the body following binding by the VHH or multimeric form thereof.

In an aspect, an anti-tag (i.e., anti-epitope tag) antibody may be administered to a subject who is also treated with or administered an anti-TcdB VHH or multimeric form thereof containing one or more epitope tags, or a pharmaceutical composition thereof. The anti-tag antibodies bind to the epitope tags of the anti-TcdB VHH, which, in turn, binds to one or more toxin B proteins, thereby forming a complex that is rapidly cleared from the body (Sepulveda, J. et al., 2010, *Infect. Immun.,* 78(2); 756-763; Mukherjee, J. et al., 2012, PLOS ONE, 7(1); e29941. PMCID: PMC3253120). In an embodiment, an anti-epitope tag monoclonal antibody of a specific isotype, for example IgG1, or a binding fragment or portion thereof that binds to the tag sequence, or a molecule containing its CDR components that bind to the tag sequence, may be provided to a subject who is also administered one or more anti-TcdB VHHs or a multimeric form thereof as described herein. The administration or co-administration of an anti-tag antibody advantageously enhances clearance from the body of a complex formed by toxin TcdB bound by anti-TcdB VHH or a multimeric form thereof, which is, in turn, bound by an anti-epitope tag antibody or binding portion thereof.

In certain embodiments, an anti-tag antibody may also effect or facilitate immunoglobulin effector functions. Anti-tag antibodies may include, for example, IgA, IgD, IgE, IgG, and IgM immunoglobulins and subtypes thereof. An immune response to an epitope tag included in an anti-TcdB VHH or multimeric form thereof may involve the elicitation of specific monoclonal antibodies and/or polyclonal antibodies that specifically bind to the tag. Immunoglobulin effector functions may involve, for example, interaction(s) between the Fc portion of the immunoglobulin and receptors or other protein molecules in a subject or cells thereof. Depending on the immunoglobulin type, the effector functions result in clearance of the disease agent (e.g., excretion, degradation, lysis or phagocytosis). In an embodiment, an anti-tag antibody of one immunoglobulin effector type binds to an anti-TedB VHH or multimeric form thereof which comprises one or more epitope tags. In embodiments in which a multimeric form of an anti-TcdB VHH comprises at least one epitope tag, or two or more epitope tags, an anti-tag antibody, or binding portion thereof, binds to each of the tags of the multimeric molecule. In embodiments, the epitope tags may be the same or different in a given anti-TcdB VHH multimeric molecule. Without wishing to be bound by theory, the presence of more than one epitope tag bindable by an anti-epitope tag antibody, or binding portion thereof, in a multimeric form of an anti-TcdB VHH may increase the rate and/or level of clearance of toxin B bound to the anti-TcdB VHH multimer in a subject.

Suitable methods of producing or isolating antibody fragments having the requisite binding specificity and affinity for binding to an epitope tag include for example, methods which select recombinant antibody from a library or by PCR (e.g., U.S. Pat. No. 5,455,030) and U.S. Pat. No. 7,745,587 each of which is incorporated by reference herein in its entirety).

Functional fragments of antibodies, including fragments of chimeric, humanized, primatized, veneered, or single chain antibodies, can also be produced. Functional fragments or portions of the foregoing antibodies include those which are reactive with the toxin protein. For example, antibody fragments capable of binding to the toxin protein or a portion thereof, include, but not limited to, scFvs, Fabs, VHHs, Fv, Fab, Fab' and F(ab')$_2$. Such fragments can be produced by enzymatic cleavage or by recombinant techniques. For instance, papain or pepsin cleavage are used generate Fab or F(ab')$_2$ antibody fragments, respectively. Antibody fragments are produced in a variety of truncated forms using antibody-encoding genes in which one or more stop codons has been introduced upstream of the natural stop site. For example, a chimeric gene encoding a F(ab')$_2$ heavy chain peptide portion can be designed to include DNA sequences encoding the CH$_1$ peptide domain and hinge region of an immunoglobulin heavy chain.

Pharmaceutical Compositions

Also featured herein are methods for treating or preventing pathologies and disease caused by toxin B produced by *C. difficile* following infection of a subject by *C. difficile* microorganisms. The methods include administering to a subject in need thereof an amount of an anti-TcdB VHH or multimeric anti-TcdB VHH binding molecule that is effective to specifically bind to and optimally neutralize *C. difficile* toxin B. In an embodiment, if an anti-TcdB VHH or multimeric anti-TcdB VHH binding molecule includes an epitope tag, an anti-epitope tag antibody may be administered to the subject. (see, e.g., WO 2019/094095A1, the contents of which is incorporated by reference herein in its entirety). In an embodiment, an anti-TcdB VHH or multimeric anti-TcdB VHH binding molecule is provided or used in a pharmaceutical composition.

Typically, a carrier or excipient is included in a composition as described herein, such as a pharmaceutically acceptable carrier or excipient, which includes, for example, sterile water, aqueous saline solution, aqueous buffered saline solutions, aqueous sucrose, dextrose, or mannose solutions, aqueous glycerol solutions, ethanol, calcium carbonate, albumin, starch, cellulose, silica gel, polyethylene glycol (PEG), dried skim milk, rice flour, magnesium stearate, and the like, or combinations thereof. The terms "pharmaceutically acceptable carrier" and a "carrier" refer to any generally acceptable excipient or drug delivery device that is relatively inert and non-toxic.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's The Science and Practice of Pharmacy Ed*. by LWW 21$^{st}$ EQ. PA, 2005 discloses various carriers used in formulating pharmaceutical compositions and known techniques for the preparation thereof. Carriers are selected to prolong dwell time for example following any route of administration, including IP, IV, subcutaneous, mucosal, sublingual, inhalation or other form of intranasal administration, or other route of administration.

Some examples of materials that can serve as pharmaceutically acceptable carriers include, but are not limited to, sugars such as glucose, and sucrose: starches such as corn starch and potato starch: cellulose and its derivatives such as sodium carboxymethyl cellulose, ethyl cellulose, and cellulose acetate: powdered tragacanth: malt: gelatin: talc: excipients such as cocoa butter and suppository waxes: oils such as peanut oil, cottonseed oil, safflower oil, sesame oil, olive oil, corn oil, and soybean oil: glycols such as propylene glycol: esters such as ethyl oleate and ethyl laurate: agar: buffering agents such as magnesium hydroxide and aluminum hydroxide: alginic acid: pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The preparation of such compositions and solutions ensuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, intravenous, oral, and the like.

In certain embodiments, these compositions optionally further comprise one or more additional therapeutic agents. In certain embodiments, the additional therapeutic agent(s) is/are selected from antibiotics particularly antibacterial compounds, anti-viral compounds, anti-fungals. In some embodiment, additional therapeutic agent(s) may include one or more of growth factors, anti-inflammatory agents, vasopressor agents, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), hepatocyte growth factor (HGF), and hyaluronic acid.

In an aspect, according to the methods of treatment described herein, immunization is promoted by contacting the subject with a pharmaceutical composition containing an anti-TcdB VHH or multimeric form thereof, as described herein. Thus, methods are provided for immunization, comprising administering to a subject in need thereof, such as a subject infected with *C. diff.* or a subject having CDI or symptoms thereof, a therapeutically effective amount of a pharmaceutical composition comprising an anti-TedB VHH or multimeric form thereof as active agent for a time necessary to achieve the desired result. It will be appreciated that the methods encompass protectively administering a composition comprising an anti-TcdB VHH or multimeric form thereof as a preventive or therapeutic measure to ameliorate, reduce, abrogate, or diminish infection or the effects thereof by *C. difficile*, thus, minimizing complications associated with a slow development of immunity or response to infection (especially in compromised patients such as those who are nutritionally challenged, or at risk patients such as the elderly or infants).

A therapeutically effective dose refers to that amount of active agent which ameliorates at least one symptom or condition. Therapeutic efficacy and toxicity of active agents can be determined by standard pharmaceutical procedures in cell cultures or experimental animals, e.g., $ED_{50}$ (the dose that is therapeutically effective in 50% of the population) and $LD_{50}$ (the dose that is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices are especially useful. The data obtained from cell culture assays and from animal studies are used in formulating a range of dosages for human administration. By way of example, a therapeutic dose may be at least about 1 μg per kg, at least about 5, 10, 50, 100, 500 μg per kg, at least about 1 mg/kg, 5, 10, 50 or 100 mg/kg body weight of a composition or active component thereof per body weight of the subject, although the doses may be more or less depending on age, health status, history of prior infection, and immune status of the subject as would be known by one of skill in the art. Doses may be divided or unitary and may be administered once daily, or repeated at appropriate intervals.

Administration of Pharmaceutical Compositions

After formulation with an appropriate pharmaceutically acceptable carrier in a desired dosage, a pharmaceutical composition comprising an anti-TcdB VHH or multimeric form thereof, or an anti-TcdB VHH or multimeric form thereof, can be administered to humans and other mammals by routes known and practiced in the art.

The administration of an anti-TcdB VHH or multimeric form thereof, or a pharmaceutical composition comprising of an anti-TedB VHH or multimeric form thereof, as a therapeutic for the treatment or prevention of disease or pathology caused by toxin B produced by *C. difficile* following infection may be by any suitable means that results in a concentration of the therapeutic that, combined with other components, if desired, is effective in ameliorating, reducing, eliminating, abating, or stabilizing disease, pathology, or the symptoms thereof in a subject. The therapeutic may be administered systemically, for example, formulated in a pharmaceutically-acceptable composition or buffer such as physiological saline.

Routes of administration include, for example and without limitation, subcutaneous, intravenous, intraperitoneal, intramuscular, intrathecal, intraperitoneal, or intradermal injections that provide continuous, sustained levels of the therapeutic in the subject. Other routes include, without limitation, gastrointestinal, esophageal, oral, rectal, intravaginal, etc. The amount of the therapeutic to be administered varies depending upon the manner of administration, the age and body weight of the subject, and with the clinical symptoms of the bacterial infection or associated disease, pathology, or symptoms. Generally, amounts will be in the range of those used for other agents used in the treatment of disease or pathology associated with *C. difficile* infection, although in certain instances, lower amounts may be suitable because of the increased range of protection and treatment afforded by the described anti-TcdB VHHs or multimeric forms thereof as therapeutics. A composition is administered at a dosage that ameliorates, decreases, diminishes, abates, alleviates, or eliminates the effects of the bacterial (microorganism) infection or disease (e.g., CID or the symptoms thereof) as determined by a method known to one skilled in the art.

In embodiments, a therapeutic or prophylactic treatment agent may be contained in any appropriate amount in any suitable carrier substance, and is generally present in an amount of 1-95% by weight of the total weight of the composition. The composition may be provided in a dosage form that is suitable for parenteral (e.g., subcutaneous, intravenous, intramuscular, intrathecal, or intraperitoneal) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions may in some cases be formulated to release the active agent substantially immediately upon administration or at any predetermined time or time period after administration. The latter types of compositions are generally known as controlled release formulations, which include (i) formulations that create a substantially constant concentration of a therapeutic agent or drug within the body over an extended period of time; (ii) formulations that after a predetermined lag time create a substantially constant concentration of a therapeutic agent or drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with an organ, such as the gut or gastrointestinal system; (v) formulations that allow for convenient dosing, such that doses are administered, for example, once every one or two weeks; and (vi) formulations that target a disease using carriers or chemical derivatives to deliver the therapeutic agent or drug to a particular cell type. For some applications, controlled release formulations obviate the need for frequent dosing during the day to sustain a therapeutic level in plasma, serum, or blood. In an embodiment, one or more anti-TcdB VHHs or multimeric forms thereof may be formulated with one or more additional components for administration to a subject in need, e.g., patients who have contracted *C. difficile* infection and suffer from the serious repercussions of toxin production by these microorganisms.

Any of a number of strategies can be pursued in order to obtain controlled release of a therapeutic agent in which the rate of release outweighs the rate of metabolism of the therapeutic agent or drug in question. In one example, controlled release is obtained by appropriate selection of various formulation parameters and ingredients, including, e.g., various types of controlled release compositions and coatings. Thus, the therapeutic agent or drug may be formulated with appropriate excipients into a pharmaceutical composition that, upon administration, releases the therapeutic agent or drug in a controlled manner. Examples include single or multiple unit tablet or capsule compositions, oil solutions, suspensions, emulsions, microcapsules, microspheres, molecular complexes, nanoparticles, patches, and liposomes.

Compositions for parenteral or oral use may be provided in unit dosage forms (e.g., in single-dose ampules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent (i.e., an anti-TcdB VHH or multimeric form thereof) that reduces or ameliorates a disease, pathology, or symptom thereof, such as CID, *C. difficile*-associated diarrhea (CDAD), pseudomembranous colitis (PMC), bowel inflammation, enterocytic detachment, alteration, disruption, or elimination of natural intestinal microflora, and/or paralytic ileus caused by *C. difficile* infection, the composition may include suitable parenterally acceptable carriers and/or excipients. In some cases, an active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

In some embodiments, compositions comprising an anti-TcdB VHH or multimeric form thereof are sterilized and, if desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. In some embodiments, an anti-TcdB VHH or multimeric form thereof are combined, where desired, with other active substances, e.g., enzyme inhibitors, to reduce metabolic degradation. An effective amount of a pharmaceutical composition can vary according to choice or type of anti-TcdB VHH or multimeric form thereof as described herein, the particular composition formulated, the mode of administration and the age, weight and physical health or overall condition of the patient, for example. In an embodiment, an effective amount of an anti-TcdB VHH or multimeric form thereof and/or anti-epitope tag antibody is an amount which is capable of reducing one or more symptoms of disease or pathology caused by *C. diff.* infection and the production of its toxins, namely, toxin B.

In certain embodiments, a composition includes one or more polynucleotide sequences that encode one or more anti-TcdB VHHs or multimeric forms thereof as described herein. In an embodiment, a polynucleotide sequence encoding an anti-TcdB VHH or multimeric form thereof is in the form of a DNA molecule or multimer. In some embodiments, the composition includes a plurality of nucleotide sequences each encoding an anti-TcdB VHH or multimeric form thereof, or any combination of anti-TcdB VHHs described herein, such that the anti-TcdB VHH antibodies or multimers thereof are expressed and produced in situ. In such compositions, a polynucleotide sequence is administered using any of a variety of delivery systems known to those of ordinary skill in the art, including eukaryotic, bacterial, viral vector nucleic acid expression systems, or *Spirulina*-based delivery as described infra. Suitable nucleic acid expression systems contain appropriate nucleotide sequences operably linked for expression in a patient (such as suitable promoter and termination signals). Bacterial delivery systems involve administration of a bacterium that secretes or expresses the polypeptide on its cell surface, e.g., probiotic *E. coli* as described infra. In an embodiment, a polynucleotide molecule encoding an anti-TcdB VHH or multimeric form thereof can be introduced using a viral expression system (e.g., vaccinia or other pox virus, retrovirus, lentivirus, or adenovirus associated virus (AAV)), which uses a non-pathogenic (defective), replication competent virus. Techniques for incorporating nucleic acid (DNA) into such expression systems are well known to and practiced by those of ordinary skill in the art. The nucleic acid (DNA) can also be "naked," as described, for example, in Ulmer et al., 1993, *Science*, 259:1745-1749 and as reviewed by Cohen, 1993, *Science* 259:1691-1692. The uptake of naked DNA can be increased by the use of nanoparticles comprising DNA or coating the DNA onto biodegradable beads, which are efficiently transported into recipient cells.

Therapeutic Methods

Methods of treating disease, conditions, pathology and/or symptoms thereof associated with *C. difficile* infection are provided. The methods comprise administering a therapeutically effective amount of an anti-TcdB VHH or multimeric form thereof as described herein, or a pharmaceutical composition comprising these agents to a subject (e.g., a mammal such as a human). In an embodiment, the method is for treating a subject suffering from or susceptible to CDI, *C. difficile*-associated diarrhea (CDAD), pseudomembranous colitis (PMC), bowel inflammation, enterocytic detachment, alteration, disruption, or elimination of natural intestinal microflora, and/or paralytic ileus caused by *C. difficile* infection, or a symptom thereof. The method includes administering to the subject a therapeutically effective amount of an anti-TcdB VHH, multimeric form thereof, or composition thereof sufficient to treat the disease, illness, condition, disorder and/or symptom thereof, under conditions such that the disease or disorder and/or symptom thereof is treated.

The therapeutic methods include prophylactic as well as therapeutic treatment. In an embodiment, the treatment method includes administering a therapeutically effective amount of an anti-TcdB VHH or multimeric form thereof as described herein, or a pharmaceutical composition comprising these agents, before or during the time that a subject is administered one or more antibiotics, or a treatment involving a course of antibiotics, to treat a different bacterial disease or infection. As will be appreciated by the skilled practitioner in the art, antibiotic treatment can disturb, disrupt, or otherwise adversely affect the normal microflora, microfauna and microbiome in the GI tract of a subject, thereby allowing *C. difficile* bacteria to proliferate, or overproliferate, causing CDI and other *C. difficile* promoted disease or disorders and symptoms thereof. Accordingly, providing a subject with an anti-TcdB VHH or multimeric form of the anti-TcdB VHHs provides a beneficially useful and practical prophylactic and/or therapeutic treatment regimen for a subject in need.

A subject or patient includes an animal, particularly a mammal, and more particularly, a human. Such an anti-TcdB VHH or multimeric form thereof as described herein, or a pharmaceutical composition comprising these agents, used as therapeutics in treatments will be suitably administered to subjects or patients suffering from, having, susceptible to, or at risk for a disease, disorder, or symptom thereof caused by or associated with infection by *C. difficile* microorganisms and toxin B produced by *C. diff*. Determination of patients who are "susceptible" or "at risk" can be made by any objective or subjective determination obtained by the use of a diagnostic test or based upon the opinion of a patient or a health care provider (e.g., genetic test, enzyme or protein marker, family history, and the like). Identifying a subject in need of such treatment can be in the judgment of a subject himself or herself, or of a health care/medical professional and can be subjective (e.g., opinion) or objective (e.g., measurable or quantifiable by a test or diagnostic method).

Methods of Delivery

In an embodiment, an anti-TcdB VHH or multimeric form thereof as described herein, or a pharmaceutical composition comprising these agents, can be administered to a subject in need of treatment for intoxication by a toxin B protein (TcdB). In an embodiment, a mixture of anti-TcdB VHHs or multimeric forms thereof can be administered to a subject in need of treatment for infection or intoxication by *C. diff*. In an embodiment, the anti-TcdB VHH or multimeric form thereof may include one or more epitope tag sequences to which anti-epitope tag antibody(ies) specifically bind. In another embodiment in which the anti-TcdB VHH or multimeric form thereof administered to a subject includes one or more epitope tag sequences, a specific anti-epitope tag antibody can also be administered to the subject.

In some embodiments, the administration of two or more anti-TcdB VHHs or multimeric forms thereof may increase the effectiveness of the therapy to treat infection by *C. diff*, and TcdB production and reduce the severity of one or more negative symptoms related to exposure of the subject to TcdB. In an embodiment, administering to a subject the anti-TcdB VHH or multimeric form thereof that includes one or more, e.g., two, epitope tag sequences may result in improved therapy, treatment, or protection against disease caused by *C. diff*, and its production of TcdB. In an embodiment, the epitope tag sites of the anti-TcdB VHH or multimeric form thereof are bound by a specific anti-tag antibody. The administration of an anti-TcdB VHH or multimeric form thereof as described herein, or a composition comprising the agent, and the administration of one or more anti-epitope tag antibodies may be performed simultaneously or sequentially in time. In an embodiment, an anti-TcdB VHH or multimeric form thereof is administered before, after, or at the same time as the administration of another anti-TcdB VHH or multimeric form thereof, or before administration of an anti-tag antibody, provided that the anti-TcdB VHH(s) or multimeric form(s) thereof and/or the anti-tag antibody(ies) are administered close enough in time to have the desired effect (e.g., before the anti-TcdB VHHs or multimeric forms thereof have been cleared by the body). Accordingly, "co-administration" embraces the administration of an anti-TcdB VHH or multimeric form thereof and a subsequent anti-TcdB VHH or multimeric form thereof, or the anti-tag antibody, at time points that will achieve effective treatment of disease caused by *C. diff*. toxin B, such as reduction in the level of toxin B and disease and symptoms associated with the presence of the toxin. The described methods are not limited by time intervals between which an anti-TcdB VHH or multimeric form thereof and/or the anti-tag antibody(ies) are administered: provided that these agents, or compositions containing these agents, are administered close enough in time to produce or achieve the desired effect. In an embodiment, only an anti-TedB VHH or multimeric form thereof is administered to a subject in need thereof. In another embodiment, an anti-TcdB VHH or multimeric form thereof and an anti-epitope tag antibody are premixed and administered together, or are not premixed but are co-administered within minutes of each other. In other embodiments, the anti-TcdB VHH or multimeric form thereof and anti-epitope tag antibody (ies) are co-administered with other medications, drugs, compounds, or compositions suitable for treating the disease agent.

In yet other embodiments, an anti-TcdB VHH or multimeric form thereof, or a composition containing the agent (s), is administered to a subject prior to the potential risk of exposure to infection by toxin B-producing *C. difficile* in order to protect a subject from disease and symptoms caused by toxin B. For example, an anti-TcdB VHH or multimeric form thereof and/or anti-epitope tag antibody ("clearing antibody") is administered minutes, hours or days prior to the risk of exposure to infection by *C. difficile*. Alternatively, an anti-TcdB VHH or multimeric form thereof is administered concomitantly with the risk of exposure of a subject to infectious *C. difficile* microorganisms and production of toxin B (i.e., the target of the anti-TcdB VHH or multimeric form thereof), or slightly after the risk of exposure. For example, an anti-TcdB VHH or multimeric form thereof is administered to a subject at the moment that the subject contacts, enters, or passes through an environment (e.g., room, hallway, building, and field) containing a risk of exposure to *C. difficile* microorganisms.

The methods described herein provide treating or protecting a subject from intoxication and disease (and the symptoms thereof) caused by the toxin B protein produced by *C. difficile* bacteria that have infected the subject. In accordance with the method, one or more anti-TcdB VHHs or multimeric forms thereof and, optionally, an anti-tag antibody(ies) as described herein are administered to the affected or at risk subject. Administration ameliorates, reduces, or alleviates the severity of one or more symptoms of the *C. diff*.-induced disease or condition. The presence, absence, or severity of symptoms is measured, for example, using physical examination, tests and diagnostic procedures known and practiced in the art. In certain embodiments, the presence, absence and/or level of *C. diff*. and/or its produced toxin B protein are measured using methods known and employed in the art. Symptoms or levels of the toxin B protein can be measured at one or more time points (e.g., before, during and after treatment, or any combination thereof) during the course of treatment with an anti-TcdB VHH or multimeric form thereof to determine if the treatment is effective. A decrease, reduction, or no change in the levels of the toxin B protein, or in the severity of symptoms associated therewith indicates that treatment is effective, and an increase in the level of toxin B, or in the severity of symptoms in a subject indicates that treatment is not effective. In various embodiments, the symptoms and levels of toxin B are measured using methods known and employed in the art. Specific, yet nonlimiting, symptoms that are monitored in subjects with *C. difficile* infection may include watery diarrhea, cramping/tenderness (mild symptoms); severe watery diarrhea, colitis, severe abdominal cramping/ tenderness, rapid heart rate, fever, blood in stool, dehydration, loss of appetite and weight, swollen abdomen, kidney failure and increase leukocyte count (severe symptoms). Treatment or protection from intoxication by toxin B is assessed as increased survival and reduction, alleviation, or prevention of symptoms. Methods, compositions and kits involving the use of the anti-TcdB VHHs or multimeric forms thereof described herein decrease and alleviate the symptoms of *C. diff.* infection and toxin B production and also improve survival from exposure to the *C. diff.* bacteria themselves.

Modes of Delivery of Anti-TcdB VHHs for Treatment of CDI

The anti-TcdB VHHs or multimeric forms thereof described herein can serve as effective parenteral therapeutics, e.g., in several animal models and in patients. These anti-TcdB VHHs or multimeric forms may substantially improve functional stability in the harsh proteolytic conditions of the GI tract. A number of different modes of delivery may be employed to administer these VHH molecules, such as enteric delivery, intravenous or subcutaneous delivery. In addition, suitable oral delivery modes and systems as described herein may circumvent or overcome loss of protein stability associated with the provision of protein therapeutics in the environment of the GI tract. In embodiments, the anti-TcdB VHHs and multimeric forms thereof are employed in oral, enteric, or parenteral delivery systems and offer more stable therapeutics for treating TcdB intoxication and CDI caused by *C. difficile* infection.

Spirulina-Based Oral or Enteric Treatment of CDI

In an aspect, the anti-TcdB VHHs or multimeric forms thereof described herein are delivered orally or enterically using genetically modified cyanobacteria or *Spirulina*, a blue-green alga, as described, for example, in U.S. Pat. No. 10,131,870 (Lumen Biosciences) and WO 2016/040499 A1, the contents of which are incorporated by reference herein in their entireties. In an embodiment, *Spirulina* algae are non-naturally occurring, stable transformants comprising at least one introduced targeted nucleotide mutation in their genome. In embodiments, the *Spirulina* is *Arthrospira platensis* or *Arthrospira maxima*. In some embodiments, the *Spirulina* is *Arthrospira platensis* NIES-39 or *Arthrospira* sp. PCC 8005. *Spirulina* modified to contain one or more stable, targeted mutations are suitable for molecularly engineering to harbor and express polynucleotides encoding the anti-TcdB binding polypeptides (anti-TcdB VHHs) as described herein and for producing and manufacturing products for therapeutic use. In an embodiment, the *Spirulina* organisms are engineered to express protease stable anti-TcdB VHHs. In an embodiment, such engineered *Spirulina* organisms are orally delivered to a subject in need for the treatment of CDI in the subject. In another embodiment, such engineered *Spirulina* organisms are enterically delivered to a subject in need for the treatment of CDI in the subject. Protease-stable anti-TcdB VHHs that neutralize TcdB toxin may thus be provided to the subject. Engineered *Spirulina* have been demonstrated be capable of expressing functional VHHs directed against an enteric pathogen at high levels (e.g., >1% dry mass); therapeutic efficacy of such a VHH product expressed by engineered *Spirulina* has also be shown.

Probiotic *E. coli* Engineered to Secrete or Express TcdB-Binding VHH

The human gastrointestinal (GI) tract contains a complex symbiotic microbiota that is estimated to comprise more than 40,000 species and in some regions more than $10^{11}$ organisms. The microbiota of the GI tract aids in maintaining immune homeostasis in the gut-associated lymphoid tissues, optimizing nutritional uptake, and supporting gut development. The entire intestinal epithelium is overlaid with a thick mucus layer, which, in conjunction with an effective immune system, keep the enormous bacterial load strictly sequestered on the luminal side of the gut, thus preventing penetration across the epithelial barrier. (See. e.g., K. Gronbach et al., 2010, *Infect Immun*, 78(7); 3036-3046).

The importance of the cross talk between the microbiota, intestinal epithelial cells, and the innate and adaptive components of the immune system is shown by a variety of intestinal pathological conditions, including Crohn's disease, ulcerative colitis, pouchitis, irritable bowel syndrome, necrotizing enterocolitis (NEC), and CDI. Immature or genetically compromised immunity results in exaggerated intestinal inflammation or disruption or altered composition of the intestinal mucosa, which, in turn, disturbs the homeostasis between a human host and its intestinal microbial symbionts. Pathological events, such as infection by pathogens, e.g., *C. difficile*, change the relative balance between beneficial and aggressive enteric symbionts, convert beneficial bacteria into pathogens, or select for new opportunistic pathogens. A qualitatively and quantitatively changed gastrointestinal microbiota, often termed small bowel bacterial overgrowth (SIBO) or dysbiosis, may contribute substantially to local chronic inflammation in a vicious cycle and provoke bacterial translocation that leads to fatal sepsis.

The foregoing provides the rationale for selective therapeutic manipulation of the abnormal microbiota by probiotics as therapeutics for the intestinal diseases. In general, probiotics are viable microorganisms with beneficial physiological or therapeutic activities. Various in vitro and animal studies with probiotics, including *Escherichia coli* strain Nissle 1917, have demonstrated the capacity of probiotics to reduce intestinal inflammation, to strengthen the intestinal barrier against pathogens, to increase the host innate immune functions, or to prevent adherent and invasive *E. coli* strains from adhering to and invading human intestinal epithelial cells. (Id.) Limited clinical trials using *E. coli* strain Nissle 1917 or other microorganisms have suggested that this therapeutic strategy can be efficacious in patients with GI tract conditions such as chronic idiopathic inflammatory bowel diseases (IBD), irritable bowel syndrome (IBS), and NEC.

In an embodiment, strains of the probiotic *E. coli* Nissle are molecularly engineered to express and secrete functional anti-TcdB VHH polypeptides, or to express the polypeptides produced by these microorganism on their surface. Such anti-TcdB VHH-producing probiotic microorganisms provide an oral therapeutic or treatment modality for delivering the anti-TcdB VHHs to the GI tract to treat *C. difficile* pathologies and their symptoms, such as CDI. By way of example, *E. coli* Nissle strains were engineered to express VHH polypeptides that neutralized Shiga toxin; these microorganisms were shown to establish in the GI tract of animal models where they continued to produce the anti-Shiga toxin VHHs. In the same manner, the anti-TcdB binding and/or neutralizing VHHs described herein and expressed by *E. coli* Nissle strains may be utilized to provide a safe oral therapy for CDI.

Encapsulated Delivery of Anti-TcdB VHH

In another embodiment, encapsulated delivery and packaging technologies that allow orally administered protein therapeutics to pass safely through the stomach and release in the small or large intestine may be used to deliver anti-TcdB VHHs as described herein in the treatment of *C.*

*difficile* infection, CDI and symptoms thereof. Encapsulation and enteric coating techniques and processes commonly known and used in the art are suitable for delivering anti-TcdB VHHs. In embodiments, nanoparticle-based delivery of drugs and biologics and enteric coating of nanoparticles have been described by J. K. Patra et al., 2018, *J. Nanobiotech,* 16, Art. No. 71 (doi.org/10.1186/s12951-018-0392-8); US Publication No. 20200129444, the contents of which are incorporated by reference herein. Nanoparticles engineered to deliver protease-resistant, TcdB-binding and/or neutralizing VHHs may be introduced into the colons of animal models. The animals may be assessed using methods and protocols known and used in the art to determine that these animals are protected from CDI pathology.

mRNA Delivery of TcdB VHH

In an embodiment, a polynucleotide encoding an anti-TcdB VHHs or multimeric form thereof as described herein, in particular, mRNA, in the form of lipid nanoparticles is used to deliver these anti-TcdB binding agents and produce effective and long-lasting antibody titers in subjects who are passively immunized with the mRNA-nanoparticles. In a particular embodiment, the mRNA, which is otherwise unmodified, may be codon optimized to afford efficient expression of an anti-TcdB VHH or multimeric form thereof from the transcribed mRNA. It has been reported that exogenous mRNA has the ability to instruct cells to produce VHHs, as well as other types of antibodies. See, M. Thran et al., 2017, *EMBO Mol. Medicine,* online publication no. DOI 10.15252/emmm.201707678. The advantages of using mRNA for passive immunization are appreciated by those in the art. (See, M. Thran et al., Id.). mRNA-based approaches for therapeutics may be safer and more cost effective compared with DNA-based approaches. Because mRNA does not integrate into a host's DNA and is more transient in nature, mRNA-based protein expression is considered to be easier to control for protein expression.

Substantially Identical Amino Acid and Nucleotide Sequences for VHHs

There is a large body of information in the literature supporting the fact that closely related antibody (Ab) sequences are capable of performing the same binding and therapeutic functions such that this is now generally accepted by those with ordinary skill in the art of immunological sciences. The creation of Abs with small numbers of amino acid sequence variations occurs naturally within mammals and some other animal species during the process of 'affinity maturation' in which Ab-producing cells that bind a newly encountered antigen (Ag) are expanded, and their progeny cells contain random mutations within portions of the Ab coding DNA that results in new; related Ab sequences. The cells expressing Abs that have gained improved binding properties for the new Ag are then selected and expanded, thereby increasing the amount of the improved antibody in the animal. This process continues through multiple generations of mutation and selection until Abs with greatly improved binding properties result, thus providing, for example, better immunity against pathogens expressing or possessing the new Ag. The process of Ab affinity maturation demonstrates that related, yet not identical, Ab amino acid sequences can possess similar target binding properties and perform similar therapeutic functions in vivo.

Example 1 herein provides anti-TcdB VHH antibodies having related sequences that perform similar functions and provide similar therapeutic benefits. The Abs described herein are heavy-chain only, single domain VHH antibodies, which are generated in camelid alpacas, which have been reported to be convenient sources of camelid VHH antibodies (See, e.g., Maass, D. R. et al., 2007, *J. Immunol. Methods,* 324: 13-25). Briefly, alpacas are immunized with a selected *C. difficile* toxin B antigen (TcdB Ag) multiple times to permit the animal to undergo affinity maturation of the anti-TcdB VHHs that are produced. Anti-TcdB VHHs are then isolated and the encoding DNA selected for expression of soluble VHHs that bind TcdB Ag and have potential therapeutic or diagnostic properties. During this process, many examples of closely related anti-TcdB binding VHHs are isolated, which are distinctive, and which are presumably intermediates that result from the affinity maturation process which occurs during anti-TcdB VHH production in alpaca lymphocytes. These related anti-TcdB VHHs are screened for binding to TcdB Ag, and the most promising members of homology groups of TcdB-binding VHHs are identified and become lead candidates for further development.

Similar to all mammalian antibodies, VHHs comprise four, well-conserved 'framework' regions (FRs) which are important in forming the antibody structure. Between the FRs (FR1, FR2, FR3 and FR4) are three much less well-conserved CDRs or hypervariable regions (CDR1, CDR2 and CDR3) which principally interact with and bind to antigenic determinants or epitopes on antigens (Ags), such as TcdB. The CDR sequences vary widely so as to interact and bind to epitopes of Ags. The third CDR, CDR3, is generally the longest in sequence and is most diverse of the CDRs within VHHs, both in size and sequence. By way of nonlimiting example, CDR3 in VHHs can range in size from about 7 to about 28 amino acid residues. The CDR3 regions of VHHs generated in the same alpacas and selected for binding to a common target Ag are highly similar in size (number of amino acids comprising CDR3) and can vary in their amino acid identities. Without being bound by theory, VHHs and CDR3 regions that bind to the same TcdB target Ag are considered to have resulted from affinity maturation of a common precursor VHH within the animal and are classified as a 'homology group'. Individual VHHs within a homology group are classified by their binding to a target Ag, and the members of the VHH homology group are able to 'compete' with each other for binding to the Ag, thus demonstrating that they bind to the same region on the target Ag. In VHH molecules, the CDRs (CDR1, CDR2 and CD3) play a role in the ability of a VHH to bind to the target Ag, e.g., TcdB, in conjunction with CDR1 and CDR2.

Since the FRs are critical for maintaining the structure of a VHH and the positioning of the CDRs for binding to the target Ag, the FRs of VHHs typically do not vary extensively in sequence. However, some VHH FR amino acid sequence variation is permissible, particularly in cases in which an amino acid substitution involves the replacement or substitution of one amino acid with another amino acid having similar properties (e.g., similarity in being charged or uncharged), i.e., a conservative substitution. Such conservative changes in FRs can often be found naturally within VHHs that have undergone affinity maturation in an animal. Similar to the case with FRs, VHH CDRs also typically do not vary extensively in amino acid sequence or type so as not to compromise their ability to specifically bind to Ag. As would be appreciated by one skilled in the art, an estimation of the extent of amino acid sequence variation that can be tolerated within VHHs without compromising their Ag binding ability can be made by observing the variation that occurs naturally within affinity-matured homology groups of VHHs isolated from the same types of animals and which bind to the same Ag.

Figure 6A:
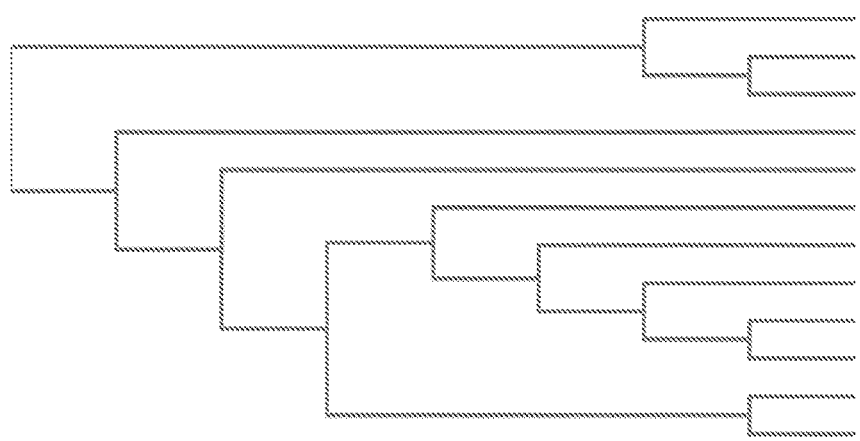

An illustrative example of VHH sequence relatedness and the retention of common antigen binding properties is shown in FIG. 6A. The relatedness among the amino acid sequences of the anti-TcdB VHH polypeptides described in Example 1 herein is represented as a phylogram or phylogenetic tree. These sequences form homology groups and all of the anti-TcdB VHHs bind to TcdB despite variation in amino acid sequence identity, e.g., from approximately 78% to approximately 91% identity. In an embodiment, sequence variation is particularly acceptable in the CDR regions, e.g., CDR1, CDR2, and/or CDR3, while the feature of VHH binding to antigen TcdB is maintained. In an embodiment, amino acid sequence variation results from conservative amino acid substitutions in a VHH sequence. In an embodiment, the conservative amino acid substitutions are in one or more CDR sequences of the VHH polypeptide. In an embodiment, the conservative amino acid substitutions are in one or more FR sequences of the VHH polypeptide. In an embodiment, the conservative amino acid substitutions are in one or more CDR sequences and in one or more FR sequences of the VHH polypeptide.

Another example evidencing that VHH sequence variation is acceptable within related VHHs having the same Ag binding characteristics is described in Tremblay et al., 2013, *Infect Immun* 81:4592-4603. In this report, 11 VHH sequences comprise a large homology group with closely related CDR3 sequences, and the unusual property of cross-specific binding to two different Shiga toxins, Stx1 and Stx2. Two of the more distantly related VHH members of this homology group are characterized as having common Ag binding characteristics. These two related VHHs were found to have 32 amino acid changes in the total VHH sequence of 120 or 121 residues. Thus, a 26% variation in amino acid sequence did not adversely affect the common Ag binding properties of the VHH proteins.

Kits

Provided herein are kits for the treatment or prevention of *C. difficile* infection or disease. In some embodiments, the kit includes an effective amount of one or more anti-TcdB VHHs or multimeric forms thereof as described herein, in unit dosage form. In an embodiment, the kit further contains an anti-epitope tag antibody, in unit dosage form. In other embodiments, the kit includes a therapeutic or prophylactic composition containing an effective amount of one or more anti-TedB VHHs or multimeric forms thereof, in unit dosage form. In still other embodiments, the kit includes a therapeutic or prophylactic composition containing an effective amount of one or more anti-TcdB VHHs or multimeric forms thereof, and an anti-epitope tag antibody, in unit dosage form. In some embodiments, the kit comprises a device, e.g., an automated or implantable device for subcutaneous delivery: an implantable drug-eluting device, or a nebulizer or metered-dose inhaler, for dispersal of the composition or a sterile container which contains a pharmaceutical composition. Non-limiting examples of containers include boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, a pharmaceutical composition is provided together with instructions for administering the pharmaceutical composition containing one or more anti-TedB VHHs or multimeric forms thereof, or one or more anti-TcdB VHHs or multimeric forms thereof and an anti-epitope tag antibody, to a subject having or at risk of contracting or developing an infection or disease or pathology, and/or the symptoms thereof, associated with infection by *C. difficile* and toxin B production by *C. difficile*. The instructions will generally include information about the use of the composition for the treatment or prevention of an infection and intoxication by the *C. difficile* bacteria and toxin B proteins that they produce. In other embodiments, the instructions include at least one of the following: description of the therapeutic/prophylactic agent: dosage schedule and administration for treatment or prevention of infection, disease or symptoms thereof caused by one or more of *C. difficile* bacteria and/or toxin B proteins that they produce: precautions: warnings: indications: counter-indications: overdosage information: adverse reactions: animal pharmacology: clinical studies; and/or references. The instructions may be printed directly on the container (when present), or as a label applied to the container, or as a separate sheet, pamphlet, card, or folder supplied in or with the container.

In another aspect, a kit is provided for treating a subject exposed to, intoxication by, or at risk for exposure to or intoxication by *C. difficile* toxin B, in which the kit includes a pharmaceutical composition for treating a subject at risk for exposure to or who is exposed to (. diff, and/or toxin B produced by *C. diff.*, and the pharmaceutical composition includes at least one recombinant anti-TcdB VHH or multimeric form thereof, such that the anti-TcdB VHH or multimeric form thereof neutralizes *C. diff.* TcdB, thereby treating the subject for exposure to the *C. diff.* disease agent: a container; and, instructions for use. In various embodiments, the instructions for use include instructions for a method for treating a subject at risk for exposure to, exposed to, or intoxicated by the *C. diff.* disease agent using the pharmaceutical composition.

The practice of the present aspects and embodiments described herein employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the aspects and embodiments described herein, and, as such, may be considered in making and practicing the same. Particularly useful techniques for particular embodiments will be discussed in the Examples that follow.

EXAMPLES

Example 1—Anti-*C. difficile* Toxin B (TcdB)-Binding VHHs

Presented in Example 1 are the amino acid and encoding polynucleotide (nucleic acid) sequences of *C. difficile* toxin B (TcdB)-binding VHH polypeptides (anti-TcdB VHHs) as described herein. The amino acids comprising the Complementarity Determining Regions (CDRs) of each of the anti-TcdB VHHs are designated in each VHH polypeptide as follows: CDR1 is designated by a single underline; CDR2 is designated by a double underline; and CDR3 is designated in bold with a single underline.

JZS-A2a (XAF-1) VHH amino acid sequence
(SEQ ID NO: 1)
QVQLAESGGGLVQAGGSLRLSCAAS<u>GSVYTFMG</u>WYRQAPGKTRELVAGI<u>SGGTITK</u>YADS
VKGRFIISRDSPKNTIYLQMNELKVEDTGVYYCNAGDTIAQAMGTRRFPFDRWGQGTQVT
VAS JZS-A2a (XAF-1) polynucleotide sequence
(SEQ ID NO: 2)
CAGGTGCAGCTCGCGGAGTCGGGAGGAGGCTTGGTGCAGGCTGGGGGGTCTCTGAGACTC
TCCTGTGCAGCCTCTGGAAGCGTGTATACTTTTATGGGCTGGTACCGCCAGGCTCCAGGG
AAGACGCGCGAATTGGTCGCAGGGATTTCAGGTGGTACGATCACAAAATATGCAGACTCC
GTGAAGGGCCGATTCATCATCTCCAGAGACAGCCCCAAGAACACAATCTATCTGCAAATG
AACGAGCTAAAAGTTGAAGACACAGGCGTGTATTACTGTAATGCAGGCGACACCATTGCA
CAGGCTATGGGGACGCGGAGGTTTCCGTTCGACCGCTGGGGCCAGGGGACCCAGGTCACC
GTCGCCTCA JZS-B2 (XAF-4) VHH amino acid sequence
(SEQ ID NO: 3)
QVQLAESGGGLVQAGGSLRLSCVGSG<u>TSFPRNYMG</u>WYRQAPGKQRELVAAI<u>SHDGNVE</u>YA
DSVKGRFTISRGNFVNTVALQMNSLKSEDTAVYYCKLVTLRRDEYWGQGTQVTVSS JZS-B2 (XAF-4) polynucleotide sequence
(SEQ ID NO: 4)
CAGGTGCAGCTCGCGGAGTCGGGAGGAGGCTTGGTGCAGGCTGGGGGGTCTCTGAGACTC
TCCTGTGCAGCCTCTGGAAGCGTGTATACTTTTATGGGCTGGTACCGCCAGGCTCCAGGG
AAGACGCGCGAATTGGTCGCAGGGATTTCAGGTGGTACGATCACAAAATATGCAGACTCC
GTGAAGGGCCGATTCATCATCTCCAGAGACAGCCCCAAGAACACAATCTATCTGCAAATG
AACGAGCTAAAAGTTGAAGACACAGGCGTGTATTACTGTAATGCAGGCGACACCATTGCA
CAGGCTATGGGGACGCGGAGGTTTCCGTTCGACCGCTGGGGCCAGGGGACCCAGGTCACC
GTCGCCTCA JZS-B9 (XAF-5) VHH amino acid sequence
(SEQ ID NO: 5)
QLQLVESGGGLVQPGGSLRLSCTS<u>ARFSLINYAIG</u>WFRQAPGQKREGVSLL<u>TSGGATY</u>YA
DSARDRFTISRDNARNTVYLQMNSLKPEDTAVYSCAAGPYSRTLVSRWKVGDGMEYWGKG
TLVTVSS JZS-B9 (XAF-5) polynucleotide sequence
(SEQ ID NO: 6)
CAGTTGCAGCTCGTGGAGTCTGGGGGAGGCCTGGTGCAGCCTGGGGGTTCTCTGAGACTC
TCCTGTACATCTGCGAGATTCTCTTTGATTAATTATGCCATAGGCTGGTTCCGCCAGGCC
CCAGGACAGAAGCGCGAGGGGGTCTCACTACTTACTAGTGGTGGTGCTACATACTATGCT
GACTCCGCGAGGGACCGATTCACCATCTCCAGAGACAACGCCAGGAACACGGTGTATTTG
CAAATGAACAGCCTGAAACCTGAGGACACGGCCGTTTATTCGTGTGCAGCAGGGCCCTAT
TCCCGAACCTTAGTCTCACGTTGGAAGGTGGGGACGGCATGGAGTACTGGGGCAAAGGG
ACCCTAGTCACCGTCTCCTCA JZS-C2 (XAF-6) VHH amino acid sequence
(SEQ ID NO: 7)
QVQLAESGGGLVQPGGSLRLSCAAS<u>GFTSNSYYIG</u>WFRQAPGKGREAVSSI<u>SSSGGSPNY</u>
ANAVKGRFTITRDNANNTVYLQMDNLKPEDTAVYYCAASKFPLTTMASNRYHYWGQGTQV
TVSS JZS-C2 (XAF-6) polynucleotide sequence
(SEQ ID NO: 8)
CAGGTGCAGCTCGCGGAGTCGGGCGGAGGCTTGGTGCAGCCTGGGGGTTCTCTGAGACTC
TCCTGTGCAGCCTCTGGATTCACTTCGAATTCTTATTACATAGGCTGGTTCCGCCAGGCC
CCAGGGAAGGGGCGCGAGGCGGTCTCAAGTATTAGTAGTAGTGGAGGTAGCCCTAACTAT
GCGAATGCCGTGAAGGGCCGATTCACCATAACCAGAGACAACGCCAACAACACGGTCTAT
CTGCAAATGGACAACCTGAAACCTGAGGACACGGCCGTTTATTACTGCGCAGCATCGAAG
TTTCCGCTAACCACTATGGCGTCCAACCGATATCATTACTGGGGTCAGGGGACCCAGGTC
ACCGTCTCCTCA JZS-C10 (XAF-9) VHH amino acid sequence
(SEQ ID NO: 9)
QLQLVETGGLVQAGGSLRLSCVGS<u>GRGPGINVMG</u>WYRQAPGTERELVATW<u>QTGGTTNY</u>AD
SVKGRFTISRDNLKNTVSLQMDSLKPEDTAVYYCYLKKWRDEYWGQGTQVTVSS JZS-C10 (XAF-9) polynucleotide sequence
(SEQ ID NO: 10)
CAGTTGCAGCTGGTGGAGACGGGAGGCTTGGTGCAGGCTGGGGGGTCTCTGAGACTCTCC
TGTGTAGGCTCTGGAAGAGGCCCCGGGATCAATGTCATGGGCTGGTACCGCCAGGCTCCA
GGGACTGAGCGCGAGTTGGTCGCAACTTGGCAAACCGGTGGTACCACAAACTATGCAGAC
TCCGTGAAGGGCCGATTCACCATCTCCAGAGACAACCTCAAGAACACGGTGTCGCTGCAA
ATGGACAGTCTGAAACCTGAGGACACAGCCGTCTATTACTGCTATCTGAAAAAATGGAGA
GATGAGTATTGGGGCCAGGGGACCCAGGTCACCGTCTCCTCA JZS-E4 (XAF-10) VHH amino acid sequence (SEQ ID NO: 11)
QVQLVESGGGLAQAGGSLRLSCAASGSSFSMNVMGWYRQPPGKQRELVATIRSDGITNYA
ESVKGRFTISRDNVKNTVHLEMNRLKAEDTAVYYCFHGRARTGNNADLGSWGQGTQVTVS
S JZS-E4 (XAF-10) polynucleotide sequence (SEQ ID NO: 12)
CAGGTGCAGCTGGTGGAGTCGGGTGGAGGCTTGGCGCAGGCTGGGGGGTCTCTGAGACTC
TCCTGTGCAGCCTCTGGAAGTAGCTTCAGCATGAATGTCATGGGCTGGTACCGCCAGCCT
CCAGGGAAGCAGCGCGAGTTGGTCGCGACTATTCGTAGTGATGGTATCACAAACTATGCA
GAGTCCGTGAAGGGCCGATTCACCATCTCCAGAGACAACGTCAAGAACACAGTGCATCTG
GAAATGAACAGGCTGAAAGCTGAAGACACAGCCGTATATTACTGCTTTCATGGCCGGGCC
CGCACAGGGAATAATGCTGACTTGGGTTCTTGGGGCCAGGGGACCCAGGTCACCGTCTCC
TCG JZS-E6 (XAF-11) VHH amino acid sequence (SEQ ID NO: 13)
QVQLAETGGGLVQAGGSLRLSCAASGRLSERIFMISTMAWYRQVPGKQRELVAEISRLGR
ANYSDSVTDRFIISRDNTKNTVDLQMNSLKPEDTAVYYCNLKPFVDNYRGPGTQVTVSS JZS-E6 (XAF-11) polynucleotide sequence (SEQ ID NO: 14)
CAGGTGCAGCTGGCGGAGACGGGTGGAGGCTTGGTGCAGGCTGGGGGGTCTCTGAGACTC
TCCTGTGCAGCTTCGGGAAGGCTCTCGGAAAGGATCTTCATGATCAGTACGATGGCCTGG
TACCGCCAGGTTCCAGGGAAGCAGCGCGAGTTGGTCGCAGAAATTTCGCGACTTGGTAGG
GCCAACTATTCAGACTCCGTGACGGACCGATTCATCATCTCCAGAGACAACACCAAGAAC
ACGGTGGATCTACAAATGAACAGCCTGAAGCCTGAGGACACAGCCGTCTATTACTGCAAT
CTTAAACCCTTCGTCGACAACTACCGGGGCCCGGGGACCCAGGTCACCGTCTCCTCT JZS-F6 (XAF-12) VHH amino acid sequence (SEQ ID NO: 15)
QLQLAESGGGLVQPGGSLRLSCAASGITFSNVAMSWVRQAPGKGLEWVSTISTGGSSTSY
LDSVKSRFTISRDNAKKTVYLQMNSLKPEDTAVYYCVKGPKYSATIRRPEGQGTQVTVSS JZS-F6 (XAF-12) polynucleotide sequence (SEQ ID NO: 16)
CAGTTGCAGCTCGCGGAGTCCGGCGGAGGCTTGGTGCAGCCTGGGGGGTCTCTGAGACTC
TCCTGTGCAGCCTCTGGAATCACCTTCAGTAACGTTGCCATGAGCTGGGTCCGCCAGGCT
CCAGGAAAGGGGCTCGAGTGGGTCTCAACTATTAGTACGGGCGGTAGTAGTACAAGCTAT
TTAGACTCCGTGAAGAGCCGATTGAGCATCTCCAGAGACAACGCCAAGAAGACGGTGTAT
CTGCAAATGAACAGTCTGAAACCTGAGGACACGGCCGTGTATTACTGTGTAAAAGGGCCC
AAGTATTCCGCTACAATCCGTCGTCCTGAGGGCCAGGGGACCCAGGTCACCGTCTCCTCA JZS-H4 (XAF-13) VHH amino acid sequence (SEQ ID NO: 17)
QLQLVESGGGLVQPGGSLRLSCVASGFNFSVQIMSWVRQAPGKGLEWVSAISTGGASKSY
ADFAKGRFTISRDNAKNTLYLQMNSLQLEDTAVYFCSKGPRTWINSSPRGQGTQVTVSS JZS-H4 (XAF-13) polynucleotide sequence (SEQ ID NO: 18)
CAGTTGCAGCTCGTGGAGTCCGGTGGAGGCTTGGTGCAGCCTGGGGGGTCTCTGAGACTC
TCCTGTGTAGCCTCTGGATTCAACTTCAGTGTGCAGATTATGAGCTGGGTCCGCCAGGCT
CCAGGAAAGGGGCTCGAGTGGGTCTCAGCTATTAGTACTGGTGGCGCTAGCAAAAGTTAT
GCAGACTTCGCGAAGGGCCGATTCACCATCTCCAGAGACAACGCCAAGAACACGCTGTAT
CTGCAAATGAACAGCCTACAACTCGAGGACACGGCCGTGTATTTTGTTCTAAGGGTCCG
AGGACTTGGATCAATTCTAGTCCCCGGGGCCAGGGGACCCAGGTCACCGTCTCCTCG JZS-H9 (XAF-14) VHH amino acid sequence (SEQ ID NO: 19)
QVQLVESGGGLVQPGGSLTINCTVSGTAFSLDTMTWYRQAPGKQRELAADISSSGASNYL
ASVKGRFTISRDNAKSALYLQMNSLKPEDTGTYYCYRGRVRGVWPLDSGMMYWGKGTLVT
VSS JZS-H9 (XAF-14) polynucleotide sequence (SEQ ID NO: 20)
CAGGTGCAGCTGGTGGAGTCCGGTGGAGGCTTGGTGCAGCCTGGGGGCTCTCTGACAATC
AACTGTACAGTCTCTGGAACCGCGTTCAGTCTCGATACCATGACCTGGTACCGCCAGGCT
CCAGGGAAGCAGCGCGAGTTGGCCGCCGATATTAGTAGTAGTGGTGCCTCAAACTATTTA
GCCTCCGTGAAGGGCCGATTCACCATCTCCAGAGATAACGCCAAGAGCGCTCTGTATCTG
CAAATGAACAGCCTGAAACCTGAGGACACAGGCACATATTATTGCTATAGAGGGCGAGTG
CGGGGAGTCTGGCCGTTGGACAGCGGCATGATGTACTGGGGTAAAGGGACCTTGGTCACC
GTCTCCTCA JZT-F7 (XAG-1) VHH amino acid sequence (SEQ ID NO: 21)
QVQLVETGGGLVQAGGSLRLSCAASGSILSSMGWYRQAPGNQREFVASISRTGATDYADS
VAGRFIISRDRGKNTVLALQMDSLKPEDTAVYYCNAGLGMGDPRRPGPWWGQGTQVTVSS -continued JZT-F7 (XAG-1) polynucleotide sequence
(SEQ ID NO: 22)
CAGGTGCAGCTCGTGGAGACTGGAGGAGGCTTGGTGCAGGCTGGGGGGTCTCTGAGACTC
TCCTGTGCAGCCTCTGGAAGCATCCTCAGTTCCATGGGCTGGTACCGCCAGGCTCCAGGA
AACCAGCGCGAGTTCGTCGCGTCTATTTCTCGTACTGGGGCGACGGACTATGCAGACTCC
GTGGCGGGCCGATTCATCATCTCTAGGGACAGAGGCAAGAACACGGTATTAGCGCTGCAA
ATGGACAGCCTGAAACCTGAGGACACAGCCGTCTATTACTGTAATGCAGGATTAGGAATG
GGGGACCCGCGACGGCCCGGTCCGTGGTGGGGCCAGGGAACCCAGGTCACCGTCTCCTCA JZT-G9 (XAG-7) VHH amino acid sequence
(SEQ ID NO: 23)
QVQLAETGGGLVQAGGSLRLSCVSS<u>ERNPGINAMG</u>WYRQAPGSQRELVAV<u>WQTGGSLS</u>YA
DSVKGRFTISRDNLKNTVYLQMNSLKPEDAAVYYCYLKKWRDQYWGQGTRVTVSS JZT-G9 (XAG-7) polynucleotide sequence
(SEQ ID NO: 24)
CAGGTGCAGCTCGCGGAGACTGGTGGAGGCTTGGTTCAGGCAGGCGGGTCTCTGAGACTC
TCCTGTGTAAGCTCTGAAAGAAATCCCGGGATCAATGCCATGGGCTGGTATCGCCAGGCT
CCAGGGAGTCAGCGCGAGTTGGTCGCAGTTTGGCAAACCGGTGGTAGCCTAAGCTATGCA
GACTCCGTGAAGGGTCGATTCACCATCTCCAGAGACAACCTCAAGAACACGGTGTATCTG
CAAATGAACAGTCTGAAACCTGAGGAGCAGCCGTCTATTATTGTTATCTGAAAAAGTGG
AGAGATCAGTATTGGGGCCAGGGGACCCGGGTCACCGTCTCCTCA Framework region (FR) sequences of the representative *C. difficile* toxin B (TcdB)-binding VHH polypeptides (anti-TcdB VHHs) described herein are presented below. Without intending to be limited by theory, in some cases, amino acid residue(s) close or directly adjacent to amino acid residue(s) at the boundaries of FR/CDR regions may be included in the FR sequence or in the CDR sequence, or such residues may vary, e.g., amino acid substitutions such as conservative substitutions, among the VHH polypeptides without adversely affecting the TcdB binding or function of the VHH polypeptides.

JZS-A2a (XAF-1):
FR1: QVQLAESGGGLVQAGGSLRLSCAAS (SEQ ID NO: 72);

FR2: MGWYRQAPGKTRELVAGI (SEQ ID NO: 73);

FR3: YADSVKGRFIISRDSPKNTIYLQMNELKVEDTGVYYC (SEQ ID NO: 74);

FR4: WGQGTQVTVAS (SEQ ID NO: 75).

JZS-B2 (XAF-4):
FR1: QVQLAESGGGLVQAGGSLRLSCVGS (SEQ ID NO: 76);

FR2: MGWYRQAPGKQRELVAAI (SEQ ID NO: 77);

FR3: YADSVKGRFTISRGNFVNTVALQMNSLKSEDTAVYYC (SEQ ID NO: 78);

FR4: WGQGTQVTVSS (SEQ ID NO: 79).

JZS-B9 (XAF-5):
FR1: QLQLVESGGGLVQPGGSLRLSCTSA (SEQ ID NO: 80);

FR2: IGWFRQAPGQKREGVSLL (SEQ ID NO: 81);

FR3: YADSARDRFTISRDNARNTVYLQMNSLKPEDTAVYSC (SEQ ID NO: 82);

FR4: WGKGTLVTVSS (SEQ ID NO: 83).

JZS-C2 (XAF-6):
FR1: QVQLAESGGGLVQPGGSLRLSCAAS (SEQ ID NO: 84);

FR2: IGWFRQAPGKGREAVSSI (SEQ ID NO: 85);

FR3: YANAVKGRFTITRDNANNTVYLQMDNLKPEDTAVYYC (SEQ ID NO: 86);

FR4: WGQGTQVTVSS (SEQ ID NO: 79).

-continued

JZS-C10 (XAF-9):
FR1: QLQLVETGGLVQAGGSLRLSCVGS (SEQ ID NO: 87);

FR2: MGWYRQAPGTERELVATW (SEQ ID NO: 88);

FR3: YADSVKGRFTISRDNLKNTVSLQMDSLKPEDTAVYYC (SEQ ID NO: 89);

FR4: WGQGTQVTVSS (SEQ ID NO: 79).

JZS-E4 (XAF-10):
FR1: QVQLVESGGGLAQAGGSLRLSCAAS (SEQ ID NO: 90);

FR2: MGWYRQPPGKQRELVATI (SEQ ID NO: 91);

FR3: YAESVKGRFTISRDNVKNTVHLEMNRLKAEDTAVYYC (SEQ ID NO: 92);

FR4: WGQGTQVTVSS (SEQ ID NO: 79).

JZS-E6 (XAF-11):
FR1: QVQLAETGGGLVQAGGSLRLSCAAS (SEQ ID NO: 93);

FR2: MAWYRQVPGKQRELVAEI (SEQ ID NO: 94);

FR3: YSDSVTDRFIISRDNTKNTVDLQMNSLKPEDTAVYYC (SEQ ID NO: 95);

FR4: GPGTQVTVSS (SEQ ID NO: 96).

JZS-F6 (XAF-12):
FR1: QLQLAESGGGLVQPGGSLRLSCAAS (SEQ ID NO: 97);

FR2: MSWVRQAPGKGLEWVSTI (SEQ ID NO: 98);

FR3: YLDSVKSRFTISRDNAKKTVYLQMNSLKPEDTAVYYC (SEQ ID NO: 99);

FR4: GQGTQVTVSS (SEQ ID NO: 100).

JZS-H4 (XAF-13):
FR1: QLQLVESGGGLVQPGGSLRLSCVAS (SEQ ID NO: 101);

FR2: MSWVRQAPGKGLEWVSAI (SEQ ID NO: 102);

FR3: YADFAKGRFTISRDNAKNTLYLQMNSLQLEDTAVYFC (SEQ ID NO: 103);

FR4: GQGTQVTVSS (SEQ ID NO: 100).

JZS-H9 (XAF-14):
FR1: QVQLVESGGGLVQPGGSLTINCTVS (SEQ ID NO: 104);

FR2: MTWYRQAPGKQRELAADI (SEQ ID NO: 105);

-continued

FR3: YLASVKGRFTISRDNAKSALYLQMNSLKPEDTGTYYC
(SEQ ID NO: 106);

FR4: WGKGTLVTVSS (SEQ ID NO: 83).

JZT-F7 (XAG-1):
FR1: QVQLVETGGGLVQAGGSLRLSCAAS (SEQ ID NO: 107);

FR2: MGWYRQAPGNQREFVASI (SEQ ID NO: 108);

FR3: YADSVAGRFIISRDRGKNTVLALQMDSLKPEDTAVYYC
(SEQ ID NO: 109);

FR4: WGQGTQVTVSS (SEQ ID NO: 79).

JZT-G9 (XAG-7):
FR1: QVQLAETGGGLVQAGGSLRLSCVSS (SEQ ID NO: 110);

FR2: MGWYRQAPGSQRELVAV (SEQ ID NO: 111);

FR3: YADSVKGRFTISRDNLKNTVYLQMNSLKPEDAAVYYC
(SEQ ID NO: 112);

FR4: WGQGTRVTVSS (SEQ ID NO: 113).

Example 2—VHH-Display Library Preparation from Genes Expressed in Immunized Camelids (Alpacas)

In a general protocol, three alpacas were immunized with TcdB (100 μg) by five successive multi-site subcutaneous (SC) injections at three week intervals. For the first immunization, the adjuvant was alum/CpG and subsequent immunizations used alum. All alpacas achieved ELISA anti-TcdB titers of 1:1,000,000. Blood was obtained from the alpacas for peripheral blood lymphocyte (PBL) preparation seven days after the fifth immunization, and RNA was extracted using the RNEASY kit (Qiagen, Valencia, CA). VHH-display phage libraries were prepared as described in Maass, D. R., et al., 2007 *Internatl J Parasitology*, 37, 953-962 and Tremblay, J. M., et al., 2010 *Toxicon* 56, 990-998.

In a particular aspect, an alpaca that had been immunized with TcdB immunogen 10 years earlier was twice boosted with 100 μg of TcdB immunogen. Following these immunizations, immune peripheral blood lymphocytes (PBL) were obtained from the animal, and a VHH display library was produced from the immune PBLs. This anti-TcdB VHH display library was called JZM-3 and had a complexity of $1.1 \times 10^7$. Another anti-TcdB VHH display library, called JYH-3, was made by combining mRNA obtained from immune PBLs isolated from two other immunized alpacas. The two anti-TcdB VHH display libraries were subjected to a panning technique. (See. e.g., Mukherjee, J., et al., 2012 *PLOS ONE*, 7, e299411; Maass, D. R., et al., 2007 *Internatl J Parasitology*, 37, 953-962 and Tremblay, J. M., et al., 2010 *Toxicon* 56, 990-998). Most toxins, particularly large toxins such as those produced by *C. difficile*, become partially denatured on plastic. Because VHH-binding is highly dependent on protein conformation, anti-TcdB VHH libraries were extensively panned on antibody-captured TcdB to capture and select VHHs that bound to conformationally native TcdB protein. A VHH heterodimer containing two TcdB-neutralizing VHHs, called 5D and E3 (plasmid JXW-2) was used as a reference.

Twenty-five (25) clonally-unrelated, unique anti-TcdB VHH antibody families were generated from the two libraries screened by panning. Based on early screening data including binding and toxin neutralization data, 20 VHHs were selected for expression, purification and characterization. Additional panning and screening for TcdB-neutralizing VHHs was performed to employ capture panning with improved libraries to identify anti-TcdB VHHs that bound to neutralizing epitopes of TcdB. In addition, assays were carried out to identify TcdB-neutralizing VHHs that were resistant to resident proteases in the gastrointestinal tract (GI proteases). Such GI protease resistant anti-TcdB VHHs advantageously provide therapeutics for enteric delivery and effectiveness, for example, by employing *Spirulina* for delivery.

Following additional characterizations, 12 out of the 20 anti-TcdB VHHs that demonstrated the highest apparent affinity for TcdB and/or the highest potency for TcdB-neutralization were selected as representatives for further use and development. The protein sequences and encoding DNA sequences of the 12 anti-TcdB VHH antibodies are provided supra.

The anti-TcdB VHH were purified and their TcdB-neutralization potencies were examined. Briefly, to evaluate the neutralization activities of these VHHs, a dilution series of the individual VHHs were incubated with Vero cells in culture, and the cells were then intoxicated with TcdB. The rounding effects of toxin exposure following culturing the cells with anti-TcdB VHHs were assessed at various times after toxin was added to the cells. As shown in FIGS. 1-4, cell rounding was assessed at 5 hrs post-intoxication with 50 pg/ml of TcdB.

In summary, several hundred individual clones were screened for TcdB-binding; positive clones were characterized; and all new and unique TcdB-binding VHH coding DNAs were re-cloned into an expression vector for soluble protein expression and purification. The purified, quantified VHHs were characterized for their potencies to neutralize TcdB in a cell-based toxicity assay. The more potent neutralizing anti-TcdB VHHs were screened for their resistance to GI tract proteases using assays developed for enteric pharmacokinetic studies. Because panning on native TcdB was employed, as well as a more complex VHH display library prepared from optimally immunized alpacas, it was expected that ten or more unique new VHHs capable of binding TcdB with high affinity (sub-nM affinities) would be identified, and subsequently selected for use.

Example 3—Binding of Anti-TcdB VHHs to TcdB

TcdB binding assays were performed to assess the binding activity of representative anti-TcdB VHH antibodies as described herein and in Yang, Z. et al., 2014, *J Infect Disease*, 210(6); 964-972; doi: 10.1093/infdis/jiu196. In addition, the neutralization activity of the representative anti-TcdB VHH antibodies was assessed in neutralization assays as described herein and in Yang, Z. et al., 2014, Id. In particular, the anti-TcdB VHH antibodies were assayed for specific TcdB binding affinity ($EC_{50}$) and neutralizing potency ($IC_{50}$). The results are presented in Table 4 below: The anti-TcdB antibodies were found to bind to TcdB with varying affinities and/or neutralize TcdB activity with different potencies. In Table 4, the affinity and potency values are designated as "apparent" (rather than "intrinsic"), because they were determined experimentally using appropriate assays as commonly known and practiced in the art.

TABLE 4

| VHH name | Vector name | Apparent affinity, (EC$_{50}$) | Apparent potency, (IC$_{50}$) |
|---|---|---|---|
| JZS-A2a | XAF-1 | >25 nM | >25 nM |
| JZS-B2 | XAF-4 | 0.3 nM | >125 nM |
| JZS-B9 | XAF-5 | 0.2 nM | 1 nM |
| JZS-C2 | XAF-6 | 3 nM | 0.5 nM |
| JZS-C10 | XAF-9 | 0.1 nM | 0.5 nM |
| JZS-E4 | XAF-10 | 2 nM | 1 nM |
| JZS-E6 | XAF-11 | 0.8 nM | 1 nM |
| JZS-F6 | XAF-12 | 0.1 nM | 0.5 nM |
| JZS-H4 | XAF-13 | 0.2 nM | 0.5 nM |
| JZX-H9 | XAF-14 | 1 nM | 15 nM |
| JZT-F7 | XAG-1 | 3 nM | 1 nM |
| JZT-G9 | XAG-7 | 0.1 nM | 3 nM |

Example 4—Neutralization of TedB by Anti-TedB VHHs

Neutralization assays as described in Example 5 infra (and as in Yang, Z. et al., 2014, *J Infect Disease,* 210(6); 964-972; doi: 10.1093/infdis/jiu196) were performed to assess the neutralization activity and apparent potency of the representative anti-TcdB VHHs described herein. The results of the assays are presented in Table 4 above and in FIGS. 1-4. In particular, the assays showed that the anti-TcdB VHHs JZS-C2, JZS-C10, and JZX-E4 (JZS-E4) displayed $IC_{50}$ TcdB-neutralization potency near 0.5 nM. (FIG. 1). The anti-TcdB VHH JZS-E6 displayed $IC_{50}$ TcdB-neutralization potency close to 1 nM; JZS-F6 displayed $IC_{50}$ TcdB-neutralization potency near 0.5 nM; and JZS-H9 displayed $IC_{50}$ TcdB-neutralization potency about 15 nM. (FIG. 2). The anti-TcdB VHH JZS-H4 displayed IC so TcdB-neutralization potency near 0.5 nM; JZT-F7 displayed $IC_{50}$ TcdB-neutralization potency close to 1 nM; and JZT-G9 displayed $IC_{50}$ TcdB-neutralization potency about 3 nM. (FIG. 3). The anti-TcdB VHHs JZS-A2a and JZS-B2 displayed minimal TcdB-neutralizing activity, while JZS-B9 displayed $IC_{50}$ TcdB-neutralization potency close to 1 nM. (FIG. 4). It will be appreciated that because neutralization assays were conducted in vitro, and slight variations may occur from assay to assay, the neutralization potency values are referred to herein as "apparent potency" values.

Example 5—Materials and Methods

Enzyme Linked Immunosorbent Assay (ELISA) EIA/RIA 96 well high binding plates (Corning Costar) coated with 0.5-5 g/ml of recombinantly produced toxin, e.g., rTcdB, overnight at 4° C. were used for immuno-binding assay's (ELISA). Plates were washed 3 times with 1×PBS+0.1% Tween, followed by washing 3 times with 1×PBS. Washed plates were blocked (4-5% non-fat dry milk in 1×PBS+0.1% Tween) for 1 hour at room temperature (RT) with rocking. Serially diluted (1:5) VHH-TcdB binding molecules targeting *C. difficile* toxin B, diluted in blocking solution, were incubated for 1 hour at RT with rocking and washed as above. Equivalent control samples were spiked with a known amount of an irrelevant VHH for use as an internal standard.

Binding of the VHHs to recombinant toxin B coating the wells was detected at A450 nm using horse radish peroxidase (HRP)-labeled anti-E-tag antibody and an ELISA reader. Bound HRP was detected using 3,3',5,5'-tetramethylbenzidine (TMB substrate, Sigma) and values were plotted as a function of the input VHH concentration. Illustratively, the plates were incubated with goat anti-E-tag-HRP conjugated antibody (Bethyl labs) diluted 1:5000 in blocking solution for 1 hour at RT with rocking and were washed as above before adding TMB microwell peroxidase substrate (KPL) to develop (incubated for 10-40 min). Development was stopped with IM $H_2SO_4$ and the plates were read at 450 nm on an ELx808 Ultra Microplate Reader (Bio-Tek instruments), (Mukherjee, J. et al., 2012, *PloS ONE* 7; e29941). VHH levels in unknown samples were determined by comparison of their signals to those of internal standards as previously described (Mukherjee, J. et al., 2014, *PLOS One* 9; e106422; Sheoran, A S et al., 2015, *Infect Immun,* 83:286-291; Moayeri, M. et al., 2016, *Clin Vaccine Immunol*, doi: 10.1128/cvi.00611-15; Sponseller, J K et al., 2014, *J Infect Dis*, doi: 10.1093/infdis/jiu605; Tzipori, S. et al., 1995, *Infect Immun,* 63:3621-3627). $EC_{50}$ values were calculated for the VHH concentration that secreted in a signal equal to 50% of the maximum signal.

Neutralization Assay

Vero cells (ATCC) at a concentration of $2.4\times10^4$ cells/100 μl of medium (DMEM high glucose+1 mM sodium pyruvate, 2 mM L-glutamine, 50U/ml and 50 μg/ml Pen/Strep pH 7.4 (HyClone)) were plated in 96-well plates overnight for 90-95% confluency, prior to addition of anti-TcdB VHH in serial dilutions (in media) (1:5) or from 100 μg/ml-1.0 fg/ml and toxic levels of TedB, such as 0.01 ng/ml to 1 ng/ml TcdB, in a 24 hour cytotoxicity/cell rounding assay (Yang, Z. et al., 2014, *J Infect Disease,* 210(6); 964-972; doi: 10.1093/infdis/jiu196). After 24 hours, toxicity to the cells was assessed by quantifying the percent (%) of cells in the plates that became rounded in each of the wells. Apparent $IC_{50}$ values for the anti-TcdB VHH polypeptides were determined.

Computational Analysis

In general, data are analyzed using GraphPad Prism software version 6. All error bars refer to standard deviations. ELISA data are analyzed using nonlinear regression.

Animal Experiments

Animal experiments involving the anti-TcdB VHHs as described herein are conducted at the Department of Infectious Disease and Global Health, Tufts Cummings School of Veterinary Medicine (North Grafton, USA) in conformance with Tufts University IACUC Protocol #G2016-74. Six- to eight-week-old female CDI mice (Charles River Labs, Wilmington, USA) are randomized based on body weight and receive single intravenous injections of LNP-formulated mRNA into the tail vein. Blood is sampled by retro-orbital bleeding at defined times, and VHH accumulation in sera is measured as described by J. M. Tremblay et al., 2013, *Infec. Immun.,* 81:4592-4603; Mukherjee et al., 2014, *PLOS ONE* 9e106422. In all studies, animals are housed under standard and humane conditions with a standard commercial rodent diet and tap water provided to the animals ad libitum.

All experiments involving animals are performed under protocols approved by Tufts University and National Institute of Allergy and Infectious Diseases (NIAID) Animal Care and Use Committees. Work with alpacas was performed at Tufts under approved protocol Tuskegee University School of Veterinary Medicine (TUSVM) and Institutional Animal Care and Use Committee (IACUC) Protocol #G2015-49. Mouse studies are performed at NIAID under approved protocols LPD8E and LPD9E.

Mouse Systemic Toxin Challenge

For in vivo studies using mice, 6 or 8 week old C57BL/6 or Balb/cJ female mice(Jackson Laboratories, Bar Harbor, ME) are intraperitoneally (IP) injected with a single dose of VHH, e.g., anti-*C. diff.* TcdB VHH (50 μg/mouse), 1 hour prior to IP injection of TcdB (100 or 200 ng/mouse). Mice are monitored for signs and symptoms of toxemia (including: lethargy, depression, anorexia, dehydration, ruffled coat, and hunched posture), e.g., over a predetermined time period, e.g., 10 days. Moribund mice are euthanized following IACUC-approved removal criteria.

Mouse CDI Challenge

In vivo experiments using mice are conducted to mimic the human condition of *C. difficile* infection (CDI) and disease and to facilitate colonization with *C. difficile*. For these experiments, ten 6 week old, C57BL/6 female mice receive filter sterilized antibiotics (kanamycin, gentamycin, colistin, metranidozole, and vancomycin) in drinking water for 5 days followed by 2 days of water alone. After 2 days of drinking the supplemented water, the mice receive one (100 μl) intraperitoneal (IP) injection of clindamycin (2 mg/ml). One day later, mice are orally challenged (Chen, X. et al., 2008, Gastroenterology. 135:1984-1992) with $10^6$ spores of an NAP1/027/BI *C. difficile* strain, designated strain UK6 (Killgore, G. et al., 2008, *J. Clin Microbiol*, 46:431-437) only (control group), or are inoculated with spores and administered anti-TcdB VHH (25-50 μg/mouse) or dimeric or multimeric forms thereof, at 4, 24 and 48 hours post-challenge (treated group). Blood is collected at 72, 96 and 120 hours post-challenge to determine VHH titers. Animals administered anti-TcdB VHH are expected to be less prone to *C. difficile*-associated disease or severe disease, symptoms and outcomes, and to have increased survival (less morbidity and death) compared with control animals that did not receive anti-TcdB VHH. In some experiments, the animals receive a prophylactic dose of anti-TcdB VHH, or dimeric or multimeric forms thereof, prior to inoculation with spores so as to prevent *C. difficile*-associated disease and/or to reduce the severity of disease and symptoms thereof, and/or to improve survival.

Hamster CDI Challenge

In vivo experiments using hamsters are conducted to mimic the human condition of *C. difficile* infection and disease and to facilitate colonization with *C. difficile*. For these experiments, male Golden Syrian hamsters (110-135 g) are administered clindamycin (30 mg/kg) via oral gavage for 5 days prior to oral inoculation with 1000 *C. difficile* strain UK6 spores. Infected control hamsters are administered clindamycin, are inoculated with UK6 spores and are given sterile PBS, by intraperitoneal (IP) administration, 2 times per day for the duration of the experiment. Anti-TcdB VHH-treated hamsters are administered clindamycin, inoculated with spores and are given purified anti-TcdB VHH (1 mg/kg), or dimeric or multimeric forms thereof, by IP administration, 2 times a day for the duration of the experiment. A blood sample is collected at time of euthanasia for detection of anti-TcdB VHH in serum. Necropsies are performed on euthanized animals and tissues are collected for histopathologic examination. Animals administered anti-TcdB VHH are expected to be less prone to *C. difficile*-associated disease or severe disease, symptoms and outcomes, and to have increased survival (less morbidity and death) compared with control animals that did not receive anti-TcdB VHH. In some experiments, the animals receive a prophylactic dose of anti-TcdB VHH, or dimeric or multimeric forms thereof, prior to inoculation with spores so as to prevent *C. difficile*-associated disease and/or to reduce the severity of disease and symptoms thereof, and/or to improve survival.

Pig CDI Challenge

Pigs have been demonstrated to mimic *C. difficile* infection, colonization and disease as experienced by humans. For in vivo experiments using pigs, thirty gnotobiotic piglets are derived via Caesarean section and maintained in sterile isolators for the duration of the experiment (Tzipori, S. et al., 1995, *Infect Immun*, 63:3621-3627). Five groups of piglets are orally inoculated with $10^6$ *C. difficile* UK6 spores (group 1-5) and group 6 was the uninfected control group. Group 1 (n=3) receives anti-TcdB VHH (1 mg/pig) 4 hours prior to, and Group 2 (n=3) 18 hours post oral inoculation with spores. After the initial dose, the treated groups receive 2 doses of anti-TcdB VHH (1 mg/pig) per day either via IP or intra muscular (IM) administration for the duration of the experiment. The anti-TcdB VHH treated group (Group 3; n=9) is given $1.0 \times 10^{11}$ viral particles by IV administration one day prior to oral inoculation with $10^6$ *C. difficile* UK6 spores and 3 days post infection. Group 4 (n=6) receives buffer as control, given 4 hours prior to oral inoculation with $10^6$ *C. difficile* UK6 spores and at 24 hour post inoculation, and then every 12 hours until the termination of the experiment. Group 5 is given control adenovirus expressing an unrelated VHH (n=6), ($1.0 \times 10^{11}$ viral particles) by IV administration one day prior to oral inoculation with $10^6$ *C. difficile* UK6 spores and 3 days post infection. Group 6 (n=3) is uninfected. Fecal samples are collected from all piglets for bacterial culture, and blood samples are collected 1-3 times (when possible) during the experiment and at the time of euthanasia to determine anti-TcdB VHH titers. Necropsies are performed on all animals and tissues are collected for histopathologic examination. Animals administered anti-TcdB VHH are expected to be less prone to *C. difficile*-associated disease or severe disease, symptoms and outcomes, and to have increased survival (less morbidity and death) compared with control animals that did not receive anti-TcdB VHH. In some experiments, the animals receive a prophylactic dose of anti-TcdB VHH, or dimeric or multimeric forms thereof, prior to inoculation with spores so as to prevent *C. difficile*-associated disease and/or to reduce the severity of disease and symptoms thereof, and/or to improve survival.

Histology

Tissue samples from *C. difficile* colonized animals are collected during necropsy and preserved in 10% neutral buffered formalin. Formalin fixed samples are embedded in paraffin, sectioned at 5 μm, and stained using hematoxylin and eosin using routine histochemical techniques at TCSVM Histopathology Service Laboratory. Light microscopic examination and lesion evaluation are performed by a board-certified veterinary pathologist (GB) with results reported for severity (minimal, mild, moderate, marked), epithelial ulceration, luminal contents, and quantification (Sponseller, J K et al., 2014, *J Infect Dis*, doi: 10.1093/infdis/jiu605). Briefly, a quantitative assessment of colitis severity is performed by counting neutrophilic foci in colon sections from each sample. Foci are observed between colonic crypts in the lamina propria in 10 random fields with ×20 magnification.

All publications, patents, published patent applications and sequence database entries mentioned and disclosed herein are hereby incorporated by reference in their entireties as if each individual publication or patent were specifically and individually indicated to be incorporated by reference.

What is claimed is:

1. A polypeptide that specifically binds to *Clostridium difficile* (*C. difficile*) toxin B (TcdB), or a TcdB-binding portion thereof, wherein the polypeptide comprises three complementarity determining regions (CDRs), CDR1, CDR2 and CDR3, and four VHH framework regions (FRs), FR1, FR2, FR3 and FR4, with the general structure FR1-CDR1-FR2-CDR2-FR3-CDR3-FR4, wherein CDR1 comprises amino acid sequence GSVYTF (SEQ ID NO: 25); CDR2 comprises amino acid sequence SGGTITK (SEQ ID NO: 26); and CDR3 comprises amino acid sequence NAGD-TIAQAMGTRRFPFDR (SEQ ID NO: 27);

wherein CDR1 comprises amino acid sequence GTSF-PRNY (SEQ ID NO: 28); CDR2 comprises amino acid sequence SHDGNVE (SEQ ID NO: 29); and CDR3 comprises amino acid sequence KLVTLRRDEY (SEQ ID NO: 30);

wherein CDR1 comprises amino acid sequence RFSLINYA (SEQ ID NO: 31); CDR2 comprises amino acid sequence TSGGATY (SEQ ID NO: 32); and CDR3 comprises amino acid sequence AAGPYSRTLVSRWKVGDGMEY (SEQ ID NO: 33);

wherein CDR1 comprises amino acid sequence GFTSN-SYY (SEQ ID NO: 34); CDR2 comprises amino acid sequence SSSGGSPN (SEQ ID NO: 35); and CDR3 comprises amino acid sequence AASKFPLTTMASN-RYHY (SEQ ID NO: 36);

wherein CDR1 comprises amino acid sequence GRGPG-INV (SEQ ID NO: 37); CDR2 comprises amino acid sequence QTGGTTN (SEQ ID NO: 38); and CDR3 comprises amino acid sequence YLKKWRDEY (SEQ ID NO: 39);

wherein CDR1 comprises amino acid sequence GSSFSMNV (SEQ ID NO: 40); CDR2 comprises amino acid sequence RSDGITN (SEQ ID NO: 41); and CDR3 comprises amino acid sequence FHGRARTGN-NADLGS (SEQ ID NO: 42);

wherein CDR1 comprises amino acid sequence GRL-SERIFMIST (SEQ ID NO: 43); CDR2 comprises amino acid sequence SRLGRAN (SEQ ID NO: 44); and CDR3 comprises amino acid sequence NLKPFVDNYR (SEQ ID NO: 45);

wherein CDR1 comprises amino acid sequence GITFSNVA (SEQ ID NO: 46); CDR2 comprises amino acid sequence STGGSSTS (SEQ ID NO: 47); and CDR3 comprises amino acid sequence VKGPKYSAT-IRRPE (SEQ ID NO: 48);

wherein CDR1 comprises amino acid sequence GFNFSVQI (SEQ ID NO: 49); CDR2 comprises amino acid sequence STGGASKS (SEQ ID NO: 50); and CDR3 comprises amino acid sequence SKGPRTWINSSPR (SEQ ID NO: 51);

wherein CDR1 comprises amino acid sequence GTAFSLDT (SEQ ID NO: 52); CDR2 comprises amino acid sequence SSSGASN (SEQ ID NO: 53); and CDR3 comprises amino acid sequence YRGRVRGVWPLDSGMMY (SEQ ID NO: 54);

wherein CDR1 comprises amino acid sequence GSILSS (SEQ ID NO: 55); CDR2 comprises amino acid sequence SRTGATD (SEQ ID NO: 56); and CDR3 comprises amino acid sequence NAGLGMGDPRRPGPW (SEQ ID NO: 57); or wherein CDR1 comprises amino acid sequence ERNP-GINA (SEQ ID NO: 58); CDR2 comprises amino acid sequence WQTGGSLS (SEQ ID NO: 59); and CDR3 comprises amino acid sequence YLKKWRDQY (SEQ ID NO: 60).

2. The polypeptide of claim 1, wherein the polypeptide neutralizes *C. difficile* toxin B (TcdB) activity.

3. The polypeptide of claim 1, which is a camelid-derived single domain anti-TcdB VHH antibody.

4. The polypeptide or the TedB-binding portion thereof of claim 1, wherein the polypeptide or the TedB-binding portion thereof has at least 85% amino acid sequence identity to a sequence selected from the group consisting of SEQ ID NOs: 1, 3, 5, 7, 9, 11, 13, 15, 17, 19, 21 and 23; wherein amino acid sequence variation occurs in one or more framework (FR) regions of the polypeptide.

5. The polypeptide of claim 4, wherein the sequence variation comprises conservative amino acid substitutions in the one or more framework (FR) regions of the polypeptide.

6. A polypeptide that specifically binds to *C. difficile* toxin B (TcdB), or a TcdB-binding portion thereof, wherein the polypeptide or the TedB-binding portion thereof comprises a sequence selected from the group consisting of SEQ ID NOs: 1, 3, 5, 7, 9, 11, 13, 15, 17, 19, 21 and 23.

7. A polypeptide that specifically binds to *C. difficile* toxin B (TcdB), or a TcdB-binding portion thereof, wherein the polypeptide or the TedB-binding portion thereof consists of a sequence selected from the group consisting of SEQ ID NOs: 1, 3, 5, 7, 9, 11, 13, 15, 17, 19, 21 and 23.

8. A dimeric or multimeric polypeptide comprising two or more anti-TcdB VHH polypeptides or TcdB binding regions thereof comprising a sequence selected from the group consisting of SEQ ID NOs: 1, 3, 5, 7, 9, 11, 13, 15, 17, 19, 21 and 23, wherein the two or more anti-TcdB VHH polypeptides, or the TedB binding regions thereof, are joined with one or more linker peptides.

9. The dimeric or multimeric polypeptide of claim 8, wherein the one or more linker peptides is selected from GGGGS (SEQ ID NO: 63); GGGGSGGGGSGGGGS (SEQ ID NO: 64), or a functional portion thereof;
EPKTPKPQGGGGSGGGGSGGGGSQGVQSQVQLVE (SEQ ID NO: 65); EPKTPKPQ (SEQ ID NO: 66); or a combination thereof.

10. The dimeric or multimeric polypeptide of claim 8, comprising one or more epitope tag sequences specifically bindable by an anti-epitope tag antibody or binding portion thereof.

11. The dimeric or multimeric polypeptide of claim 10, wherein the one or more epitope tag sequences comprises at least one of DELGPRLMGK (SEQ ID NO: 61) or GAPVPYPDPLEPR (SEQ ID NO: 62).

12. An isolated polynucleotide comprising a nucleic acid sequence encoding an anti-TcdB VHH of any one of SEQ ID NOs: 1, 3, 5, 7, 9, 11, 13, 15, 17, 19, 21, or 23.

13. An isolated polynucleotide encoding the polypeptide or the TedB-binding portion thereof of claim 1, wherein the encoded polypeptide or the TcdB-binding portion thereof has at least 85% sequence identity to a sequence selected from the group consisting of SEQ ID NOs: 1, 3, 5, 7, 9, 11, 13, 15, 17, 19, 21, and 23; wherein amino acid sequence variation occurs in one or more framework (FR) regions of the polypeptide.

14. The polypeptide of claim 1, wherein the four VHH FRs are camelid VHH FRs.

15. The polypeptide of claim 2, which is a camelid-derived single domain anti-TcdB VHH antibody.

16. The isolated polynucleotide of claim 13, wherein the encoded polypeptide or the TedB-binding portion thereof has at least 95% amino acid sequence identity to a sequence selected from the group consisting of SEQ ID NOs: 1, 3, 5, 7, 9, 11, 13, 15, 17, 19, 21 and 23.

17. The isolated polynucleotide of claim 13, wherein the sequence variation comprises conservative amino acid substitutions in the one or more framework (FR) regions of the encoded polypeptide.

* * * * *

SEQUENCE LISTING

<160> NUMBER OF SEQ ID NOS: 155

<210> SEQ ID NO 1
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Ala Glu Ser Gly Gly Gly Leu Val Gln Ala Gly Gly
1               5                   10                  15

Ser Leu Arg Leu Ser Cys Ala Ala Ser Gly Ser Val Tyr Thr Phe Met
            20                  25                  30

Gly Trp Tyr Arg Gln Ala Pro Gly Lys Thr Arg Glu Leu Val Ala Gly
        35                  40                  45

Ile Ser Gly Gly Thr Ile Thr Lys Tyr Ala Asp Ser Val Lys Gly Arg
    50                  55                  60

Phe Ile Ile Ser Arg Asp Ser Pro Lys Asn Thr Ile Tyr Leu Gln Met
65                  70                  75                  80

Asn Glu Leu Lys Val Glu Asp Thr Gly Val Tyr Tyr Cys Asn Ala Gly
                85                  90                  95

Asp Thr Ile Ala Gln Ala Met Gly Thr Arg Arg Phe Pro Phe Asp Arg
            100                 105                 110

Trp Gly Gln Gly Thr Gln Val Thr Val Ala Ser
        115                 120

<210> SEQ ID NO 2
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
caggtgcagc tcgcggagtc gggaggaggc ttggtgcagg ctggggggtc tctgagactc      60
tcctgtgcag cctctggaag cgtgtatact tttatgggct ggtaccgcca ggctccaggg     120
aagacgcgcg aattggtcgc agggatttca ggtggtacga tcacaaaata tgcagactcc     180
gtgaagggcc gattcatcat ctccagagac agccccaaga acacaatcta tctgcaaatg     240
aacgagctaa agttgaaga cacaggcgtg tattactgta atgcaggcga caccattgca      300
caggctatgg ggacgcggag gtttccgttc gaccgctggg gccaggggac ccaggtcacc     360
gtcgcctca                                                             369

<210> SEQ ID NO 3
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Ala Glu Ser Gly Gly Gly Leu Val Gln Ala Gly Gly
1               5                   10                  15

Ser Leu Arg Leu Ser Cys Val Gly Ser Gly Thr Ser Phe Pro Arg Asn
            20                  25                  30

```
Tyr Met Gly Trp Tyr Arg Gln Ala Pro Gly Lys Gln Arg Glu Leu Val
            35                  40                  45

Ala Ala Ile Ser His Asp Gly Asn Val Glu Tyr Ala Asp Ser Val Lys
 50                  55                  60

Gly Arg Phe Thr Ile Ser Arg Gly Asn Phe Val Asn Thr Val Ala Leu
 65                  70                  75                  80

Gln Met Asn Ser Leu Lys Ser Glu Asp Thr Ala Val Tyr Tyr Cys Lys
                 85                  90                  95

Leu Val Thr Leu Arg Arg Asp Glu Tyr Trp Gly Gln Gly Thr Gln Val
            100                 105                 110

Thr Val Ser Ser
        115
```

```
<210> SEQ ID NO 4
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
caggtgcagc tcgcggagtc gggaggaggc ttggtgcagg ctgggggtc tctgagactc      60 tcctgtgcag cctctggaag cgtgtatact tttatgggct ggtaccgcca ggctccaggg    120
aagacgcgcg aattggtcgc agggatttca ggtggtacga tcacaaaata tgcagactcc    180
gtgaagggcc gattcatcat ctccagagac agccccaaga acacaatcta tctgcaaatg    240
aacgagctaa agttgaaga cacaggcgtg tattactgta atgcaggcga caccattgca     300
caggctatgg ggacgcggag gtttccgttc gaccgctggg gccaggggac ccaggtcacc    360
gtcgcctca                                                            369
```

```
<210> SEQ ID NO 5
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Leu Gln Leu Val Glu Ser Gly Gly Gly Leu Val Gln Pro Gly Gly
 1               5                  10                  15

Ser Leu Arg Leu Ser Cys Thr Ser Ala Arg Phe Ser Leu Ile Asn Tyr
             20                  25                  30

Ala Ile Gly Trp Phe Arg Gln Ala Pro Gly Gln Lys Arg Glu Gly Val
         35                  40                  45

Ser Leu Leu Thr Ser Gly Gly Ala Thr Tyr Tyr Ala Asp Ser Ala Arg
 50                  55                  60

Asp Arg Phe Thr Ile Ser Arg Asp Asn Ala Arg Asn Thr Val Tyr Leu
 65                  70                  75                  80

Gln Met Asn Ser Leu Lys Pro Glu Asp Thr Ala Val Tyr Ser Cys Ala
                 85                  90                  95

Ala Gly Pro Tyr Ser Arg Thr Leu Val Ser Arg Trp Lys Val Gly Asp
            100                 105                 110

Gly Met Glu Tyr Trp Gly Lys Gly Thr Leu Val Thr Val Ser Ser
            115                 120                 125
```

<210> SEQ ID NO 6
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
cagttgcagc tcgtggagtc tgggggaggc ctggtgcagc ctgggggttc tctgagactc      60
tcctgtacat ctgcgagatt ctctttgatt aattatgcca taggctggtt ccgccaggcc     120
ccaggacaga agcgcgaggg ggtctcacta cttactagtg gtggtgctac atactatgct     180
gactccgcga gggaccgatt caccatctcc agagacaacg ccaggaacac ggtgtatttg     240
caaatgaaca gcctgaaacc tgaggacacg gccgtttatt cgtgtgcagc agggccctat     300
tcccgaacct tagtctcacg ttggaaggtg ggggacggca tggagtactg gggcaaaggg     360
accctagtca ccgtctcctc a                                                381
```

<210> SEQ ID NO 7
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

```
Gln Val Gln Leu Ala Glu Ser Gly Gly Gly Leu Val Gln Pro Gly Gly
1               5                   10                  15

Ser Leu Arg Leu Ser Cys Ala Ala Ser Gly Phe Thr Ser Asn Ser Tyr
            20                  25                  30

Tyr Ile Gly Trp Phe Arg Gln Ala Pro Gly Lys Gly Arg Glu Ala Val
        35                  40                  45

Ser Ser Ile Ser Ser Ser Gly Gly Ser Pro Asn Tyr Ala Asn Ala Val
    50                  55                  60

Lys Gly Arg Phe Thr Ile Thr Arg Asp Asn Ala Asn Asn Thr Val Tyr
65                  70                  75                  80

Leu Gln Met Asp Asn Leu Lys Pro Glu Asp Thr Ala Val Tyr Tyr Cys
                85                  90                  95

Ala Ala Ser Lys Phe Pro Leu Thr Thr Met Ala Ser Asn Arg Tyr His
            100                 105                 110

Tyr Trp Gly Gln Gly Thr Gln Val Thr Val Ser Ser
        115                 120
```

<210> SEQ ID NO 8
<211> LENGTH: 372
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
caggtgcagc tcgcggagtc gggcggaggc ttggtgcagc ctgggggttc tctgagactc      60
tcctgtgcag cctctggatt cacttcgaat tcttattaca taggctggtt ccgccaggcc     120
ccagggaagg ggcgcgaggc ggtctcaagt attagtagta gtggaggtag ccctaactat     180
gcgaatgccg tgaagggccg attcaccata accagagaca cgccaacaa cacggtctat      240
ctgcaaatgg acaacctgaa acctgaggac acggccgttt attactgcgc agcatcgaag     300
```

```
tttccgctaa ccactatggc gtccaaccga tatcattact ggggtcaggg gacccaggtc      360
accgtctcct ca                                                         372
```

<210> SEQ ID NO 9
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Gln Leu Gln Leu Val Glu Thr Gly Gly Leu Val Gln Ala Gly Gly Ser
1               5                   10                  15

Leu Arg Leu Ser Cys Val Gly Ser Gly Arg Gly Pro Gly Ile Asn Val
            20                  25                  30

Met Gly Trp Tyr Arg Gln Ala Pro Gly Thr Glu Arg Glu Leu Val Ala
        35                  40                  45

Thr Trp Gln Thr Gly Gly Thr Thr Asn Tyr Ala Asp Ser Val Lys Gly
    50                  55                  60

Arg Phe Thr Ile Ser Arg Asp Asn Leu Lys Asn Thr Val Ser Leu Gln
65                  70                  75                  80

Met Asp Ser Leu Lys Pro Glu Asp Thr Ala Val Tyr Tyr Cys Tyr Leu
                85                  90                  95

Lys Lys Trp Arg Asp Glu Tyr Trp Gly Gln Gly Thr Gln Val Thr Val
            100                 105                 110

Ser Ser
```

<210> SEQ ID NO 10
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
cagttgcagc tggtggagac gggaggcttg gtgcaggctg ggggtctct gagactctcc      60 tgtgtaggct ctggaagagg ccccgggatc aatgtcatgg gctggtaccg ccaggctcca    120
gggactgagc gcgagttggt cgcaacttgg caaaccggtg gtaccacaaa ctatgcagac    180
tccgtgaagg gccgattcac catctccaga gacaacctca gaacacggt gtcgctgcaa     240 atggacagtc tgaaacctga ggacacagcc gtctattact gctatctgaa aaaatggaga    300
gatgagtatt ggggccaggg gacccaggtc accgtctcct ca                      342
```

<210> SEQ ID NO 11
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Gln Val Gln Leu Val Glu Ser Gly Gly Gly Leu Ala Gln Ala Gly Gly
1               5                   10                  15

Ser Leu Arg Leu Ser Cys Ala Ala Ser Gly Ser Ser Phe Ser Met Asn
            20                  25                  30
```

Val Met Gly Trp Tyr Arg Gln Pro Pro Gly Lys Gln Arg Glu Leu Val
         35                  40                  45

Ala Thr Ile Arg Ser Asp Gly Ile Thr Asn Tyr Ala Glu Ser Val Lys
 50                  55                  60

Gly Arg Phe Thr Ile Ser Arg Asp Asn Val Lys Asn Thr Val His Leu
 65                  70                  75                  80

Glu Met Asn Arg Leu Lys Ala Glu Asp Thr Ala Val Tyr Tyr Cys Phe
                 85                  90                  95

His Gly Arg Ala Arg Thr Gly Asn Asn Ala Asp Leu Gly Ser Trp Gly
            100                 105                 110

Gln Gly Thr Gln Val Thr Val Ser Ser
            115                 120

<210> SEQ ID NO 12
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
caggtgcagc tggtggagtc gggtggaggc ttggcgcagg ctggggggtc tctgagactc     60
tcctgtgcag cctctggaag tagcttcagc atgaatgtca tgggctggta ccgccagcct    120
ccagggaagc agcgcgagtt ggtcgcgact attcgtagtg atggtatcac aaactatgca    180
gagtccgtga aggccgatt caccatctcc agagacaacg tcaagaacac agtgcatctg    240
gaaatgaaca ggctgaaagc tgaagacaca gccgtatatt actgctttca tggccgggcc    300
cgcacaggga ataatgctga cttgggttct tggggccagg gaccccaggt caccgtctcc    360
tcg                                                                  363

<210> SEQ ID NO 13
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Ala Glu Thr Gly Gly Gly Leu Val Gln Ala Gly Gly
 1               5                  10                  15

Ser Leu Arg Leu Ser Cys Ala Ala Ser Gly Arg Leu Ser Glu Arg Ile
             20                  25                  30

Phe Met Ile Ser Thr Met Ala Trp Tyr Arg Gln Val Pro Gly Lys Gln
         35                  40                  45

Arg Glu Leu Val Ala Glu Ile Ser Arg Leu Gly Arg Ala Asn Tyr Ser
 50                  55                  60

Asp Ser Val Thr Asp Arg Phe Ile Ile Ser Arg Asp Asn Thr Lys Asn
 65                  70                  75                  80

Thr Val Asp Leu Gln Met Asn Ser Leu Lys Pro Glu Asp Thr Ala Val
                 85                  90                  95

Tyr Tyr Cys Asn Leu Lys Pro Phe Val Asp Asn Tyr Arg Gly Pro Gly
            100                 105                 110

Thr Gln Val Thr Val Ser Ser
            115

<210> SEQ ID NO 14
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
caggtgcagc tggcggagac gggtggaggc ttggtgcagg ctgggggtc tctgagactc       60 tcctgtgcag cttcgggaag ctctcggaa aggatcttca tgatcagtac gatggcctgg      120
taccgccagg ttccagggaa gcagcgcgag ttggtcgcag aaatttcgcg acttggtagg     180
gccaactatt cagactccgt gacgaccga ttcatcatct ccagagacaa caccaagaac      240
acggtggatc tacaaatgaa cagcctgaag cctgaggaca cagccgtcta ttactgcaat     300
cttaaaccct cgtcgacaa ctaccggggc cggggaccc aggtcaccgt ctcctct         357

<210> SEQ ID NO 15
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Leu Gln Leu Ala Glu Ser Gly Gly Gly Leu Val Gln Pro Gly Gly
1               5                   10                  15

Ser Leu Arg Leu Ser Cys Ala Ala Ser Gly Ile Thr Phe Ser Asn Val
            20                  25                  30

Ala Met Ser Trp Val Arg Gln Ala Pro Gly Lys Gly Leu Glu Trp Val
        35                  40                  45

Ser Thr Ile Ser Thr Gly Gly Ser Ser Thr Ser Tyr Leu Asp Ser Val
    50                  55                  60

Lys Ser Arg Phe Thr Ile Ser Arg Asp Asn Ala Lys Lys Thr Val Tyr
65                  70                  75                  80

Leu Gln Met Asn Ser Leu Lys Pro Glu Asp Thr Ala Val Tyr Tyr Cys
                85                  90                  95

Val Lys Gly Pro Lys Tyr Ser Ala Thr Ile Arg Arg Pro Glu Gly Gln
            100                 105                 110

Gly Thr Gln Val Thr Val Ser Ser
        115                 120

<210> SEQ ID NO 16
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
cagttgcagc tcgcggagtc cggcggaggc ttggtgcagc ctgggggtc tctgagactc       60 tcctgtgcag cctctggaat caccttcagt aacgttgcca tgagctggt ccgccaggct      120 ccaggaaagg ggctcgagtg ggtctcaact attagtacgg gcggtagtag tacaagctat     180
ttagactccg tgaagagccg attcaccatc tccagagaca acgccaagaa gacggtgtat    240
ctgcaaatga acagtctgaa acctgaggac acggccgtgt attactgtgt aaaagggccc    300
aagtattccg ctacaatccg tcgtcctgag ggccagggga cccaggtcac cgtctcctca    360

<210> SEQ ID NO 17
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Leu Gln Leu Val Glu Ser Gly Gly Gly Leu Val Gln Pro Gly Gly
1               5                   10                  15

Ser Leu Arg Leu Ser Cys Val Ala Ser Gly Phe Asn Phe Ser Val Gln
            20                  25                  30

Ile Met Ser Trp Val Arg Gln Ala Pro Gly Lys Gly Leu Glu Trp Val
        35                  40                  45

Ser Ala Ile Ser Thr Gly Gly Ala Ser Lys Ser Tyr Ala Asp Phe Ala
    50                  55                  60

Lys Gly Arg Phe Thr Ile Ser Arg Asp Asn Ala Lys Asn Thr Leu Tyr
65                  70                  75                  80

Leu Gln Met Asn Ser Leu Gln Leu Glu Asp Thr Ala Val Tyr Phe Cys
                85                  90                  95

Ser Lys Gly Pro Arg Thr Trp Ile Asn Ser Ser Pro Arg Gly Gln Gly
            100                 105                 110

Thr Gln Val Thr Val Ser Ser
        115

<210> SEQ ID NO 18
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
cagttgcagc tcgtggagtc cggtggaggc ttggtgcagc ctgggggtc tctgagactc      60 tcctgtgtag cctctggatt caacttcagt gtgcagatta tgagctgggt ccgccaggct    120
ccaggaaagg ggctcgagtg gtctcagct attagtactg gtggcgctag caaaagttat    180
gcagacttcg cgaagggccg attcaccatc tccagagaca cgccaagaa cacgctgtat    240 ctgcaaatga acagcctaca actcgaggac acggccgtgt attttgttc taagggtccg    300 aggacttgga tcaattctag tccccggggc caggggaccc aggtcaccgt ctcctcg      357

<210> SEQ ID NO 19
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Glu Ser Gly Gly Gly Leu Val Gln Pro Gly Gly
1               5                   10                  15

Ser Leu Thr Ile Asn Cys Thr Val Ser Gly Thr Ala Phe Ser Leu Asp
            20                  25                  30

Thr Met Thr Trp Tyr Arg Gln Ala Pro Gly Lys Gln Arg Glu Leu Ala
        35                  40                  45

```
Ala Asp Ile Ser Ser Ser Gly Ala Ser Asn Tyr Leu Ala Ser Val Lys
     50                  55                  60

Gly Arg Phe Thr Ile Ser Arg Asp Asn Ala Lys Ser Ala Leu Tyr Leu
 65                  70                  75                  80

Gln Met Asn Ser Leu Lys Pro Glu Asp Thr Gly Thr Tyr Tyr Cys Tyr
                 85                  90                  95

Arg Gly Arg Val Arg Gly Val Trp Pro Leu Asp Ser Gly Met Met Tyr
                100                 105                 110

Trp Gly Lys Gly Thr Leu Val Thr Val Ser Ser
            115                 120
```

```
<210> SEQ ID NO 20
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
caggtgcagc tggtggagtc cgtggaggc ttggtgcagc ctgggggctc tctgacaatc      60
aactgtacag tctctggaac cgcgttcagt ctcgatacca tgacctggta ccgccaggct    120
ccagggaagc agcgcgagtt ggccgccgat attagtagta gtggtgcctc aaactattta    180
gcctccgtga agggccgatt caccatctcc agagataacg ccaagagcgc tctgtatctg    240
caaatgaaca gcctgaaacc tgaggacaca ggcacatatt attgctatag agggcgagtg    300
cggggagtct ggccgttgga cagcggcatg atgtactggg gtaaagggac cttggtcacc    360
gtctcctca                                                            369
```

```
<210> SEQ ID NO 21
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Glu Thr Gly Gly Gly Leu Val Gln Ala Gly Gly
  1               5                  10                  15

Ser Leu Arg Leu Ser Cys Ala Ala Ser Gly Ser Ile Leu Ser Ser Met
             20                  25                  30

Gly Trp Tyr Arg Gln Ala Pro Gly Asn Gln Arg Glu Phe Val Ala Ser
         35                  40                  45

Ile Ser Arg Thr Gly Ala Thr Asp Tyr Ala Asp Ser Val Ala Gly Arg
 50                  55                  60

Phe Ile Ile Ser Arg Asp Arg Gly Lys Asn Thr Val Leu Ala Leu Gln
 65                  70                  75                  80

Met Asp Ser Leu Lys Pro Glu Asp Thr Ala Val Tyr Tyr Cys Asn Ala
                 85                  90                  95

Gly Leu Gly Met Gly Asp Pro Arg Arg Pro Gly Pro Trp Trp Gly Gln
                100                 105                 110

Gly Thr Gln Val Thr Val Ser Ser
            115                 120
```

```
<210> SEQ ID NO 22
<211> LENGTH: 360
<212> TYPE: DNA
```

<213> ORGANISM: Artificial Sequence
<220> FEATURE:
<223> OTHER INFORMATION: Description of Artificial Sequence: Synthetic
      polynucleotide

<400> SEQUENCE: 22

```
caggtgcagc tcgtggagac tggaggaggc ttggtgcagg ctgggggtc tctgagactc        60 tcctgtgcag cctctggaag catcctcagt tccatgggct ggtaccgcca ggctccagga      120
aaccagcgcg agttcgtcgc gtctatttct cgtactgggg cgacggacta tgcagactcc     180
gtggcgggcc gattcatcat ctctagggac agaggcaaga acacggtatt agcgctgcaa     240
atggacagct gaaacctga ggacacagcc gtctattact gtaatgcagg attaggaatg      300
ggggacccgc gacggcccgg tccgtggtgg ggccagggaa cccaggtcac cgtctcctca      360
```

<210> SEQ ID NO 23
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Gln Val Gln Leu Ala Glu Thr Gly Gly Gly Leu Val Gln Ala Gly Gly
1               5                   10                  15

Ser Leu Arg Leu Ser Cys Val Ser Ser Glu Arg Asn Pro Gly Ile Asn
            20                  25                  30

Ala Met Gly Trp Tyr Arg Gln Ala Pro Gly Ser Gln Arg Glu Leu Val
        35                  40                  45

Ala Val Trp Gln Thr Gly Gly Ser Leu Ser Tyr Ala Asp Ser Val Lys
    50                  55                  60

Gly Arg Phe Thr Ile Ser Arg Asp Asn Leu Lys Asn Thr Val Tyr Leu
65                  70                  75                  80

Gln Met Asn Ser Leu Lys Pro Glu Asp Ala Ala Val Tyr Tyr Cys Tyr
                85                  90                  95

Leu Lys Lys Trp Arg Asp Gln Tyr Trp Gly Gln Gly Thr Arg Val Thr
            100                 105                 110

Val Ser Ser
        115
```

<210> SEQ ID NO 24
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
caggtgcagc tcgcggagac tggtggaggc ttggttcagg caggcgggtc tctgagactc        60
tcctgtgtaa gctctgaaag aaatcccggg atcaatgcca tgggctggta tcgccaggct     120
ccagggagtc agcgcgagtt ggtcgcagtt tggcaaaccg gtggtagcct aagctatgca     180
gactccgtga aggtcgatt caccatctcc agagacaacc tcaagaacac ggtgtatctg       240
caaatgaaca gtctgaaacc tgaggacgca gccgtctatt attgttatct gaaaaagtgg     300
agagatcagt attggggcca ggggacccgg gtcaccgtct cctca                     345
```

<210> SEQ ID NO 25

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Ser Val Tyr Thr Phe
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Gly Gly Thr Ile Thr Lys
1               5

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asn Ala Gly Asp Thr Ile Ala Gln Ala Met Gly Thr Arg Arg Phe Pro
1               5                   10                  15

Phe Asp Arg

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Thr Ser Phe Pro Arg Asn Tyr
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser His Asp Gly Asn Val Glu
1               5

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 30

Lys Leu Val Thr Leu Arg Arg Asp Glu Tyr
1               5                   10

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Phe Ser Leu Ile Asn Tyr Ala
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Ser Gly Gly Ala Thr Tyr
1               5

<210> SEQ ID NO 33
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Ala Gly Pro Tyr Ser Arg Thr Leu Val Ser Arg Trp Lys Val Gly
1               5                   10                  15

Asp Gly Met Glu Tyr
            20

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Phe Thr Ser Asn Ser Tyr Tyr
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Ser Ser Gly Gly Ser Pro Asn
1               5
```

```
<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Ala Ser Lys Phe Pro Leu Thr Thr Met Ala Ser Asn Arg Tyr His
1               5                   10                  15

Tyr

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Arg Gly Pro Gly Ile Asn Val
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Thr Gly Gly Thr Thr Asn
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Leu Lys Lys Trp Arg Asp Glu Tyr
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Ser Ser Phe Ser Met Asn Val
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 41

Arg Ser Asp Gly Ile Thr Asn
1               5

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Phe His Gly Arg Ala Arg Thr Gly Asn Asn Ala Asp Leu Gly Ser
1               5                   10                  15

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Arg Leu Ser Glu Arg Ile Phe Met Ile Ser Thr
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Arg Leu Gly Arg Ala Asn
1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asn Leu Lys Pro Phe Val Asp Asn Tyr Arg
1               5                   10

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Ile Thr Phe Ser Asn Val Ala
1               5

<210> SEQ ID NO 47
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Thr Gly Gly Ser Ser Thr Ser
1               5

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Val Lys Gly Pro Lys Tyr Ser Ala Thr Ile Arg Arg Pro Glu
1               5                   10

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Phe Asn Phe Ser Val Gln Ile
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Thr Gly Gly Ala Ser Lys Ser
1               5

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Lys Gly Pro Arg Thr Trp Ile Asn Ser Ser Pro Arg
1               5                   10

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Thr Ala Phe Ser Leu Asp Thr
```

```
1               5
```

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

```
Ser Ser Ser Gly Ala Ser Asn
1               5
```

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

```
Tyr Arg Gly Arg Val Arg Gly Val Trp Pro Leu Asp Ser Gly Met Met
1               5                   10                  15

Tyr
```

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Gly Ser Ile Leu Ser Ser
1               5
```

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Ser Arg Thr Gly Ala Thr Asp
1               5
```

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Asn Ala Gly Leu Gly Met Gly Asp Pro Arg Arg Pro Gly Pro Trp
1               5                   10                  15
```

<210> SEQ ID NO 58
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 58

Glu Arg Asn Pro Gly Ile Asn Ala
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Trp Gln Thr Gly Gly Ser Leu Ser
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Tyr Leu Lys Lys Trp Arg Asp Gln Tyr
1               5

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asp Glu Leu Gly Pro Arg Leu Met Gly Lys
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Ala Pro Val Pro Tyr Pro Asp Pro Leu Glu Pro Arg
1               5                   10

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Gly Gly Gly Ser
1               5
```

```
<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Gly Gly Gly Ser Gly Gly Gly Gly Ser Gly Gly Gly Gly Ser
1               5                   10                  15

<210> SEQ ID NO 65
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Pro Lys Thr Pro Lys Pro Gln Gly Gly Gly Ser Gly Gly Gly
1               5                   10                  15

Gly Ser Gly Gly Gly Gly Ser Gln Gly Val Gln Ser Gln Val Gln Leu
            20                  25                  30

Val Glu

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Glu Pro Lys Thr Pro Lys Pro Gln
1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asp Tyr Lys Asp Asp Asp Asp Lys
1               5

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: SITE
<222> LOCATION: (1)..(10)
<223> OTHER INFORMATION: This sequence may encompass 5-10 residues

<400> SEQUENCE: 68

His His His His His His His His His His
1               5                   10
```

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 69

His His His His His His
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Thr Gly Gly Ser Leu Ser
1               5

<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Ile Cys Leu Pro Arg Trp Gly Cys Leu Trp Glu Asp
1               5                   10

<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Val Gln Leu Ala Glu Ser Gly Gly Gly Leu Val Gln Ala Gly Gly
1               5                   10                  15

Ser Leu Arg Leu Ser Cys Ala Ala Ser
            20                  25

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Met Gly Trp Tyr Arg Gln Ala Pro Gly Lys Thr Arg Glu Leu Val Ala
1               5                   10                  15

Gly Ile

<210> SEQ ID NO 74
<211> LENGTH: 37
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 74

Tyr Ala Asp Ser Val Lys Gly Arg Phe Ile Ile Ser Arg Asp Ser Pro
1               5                   10                  15

Lys Asn Thr Ile Tyr Leu Gln Met Asn Glu Leu Lys Val Glu Asp Thr
            20                  25                  30

Gly Val Tyr Tyr Cys
        35

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Trp Gly Gln Gly Thr Gln Val Thr Val Ala Ser
1               5                   10

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Val Gln Leu Ala Glu Ser Gly Gly Gly Leu Val Gln Ala Gly Gly
1               5                   10                  15

Ser Leu Arg Leu Ser Cys Val Gly Ser
            20                  25

<210> SEQ ID NO 77
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Met Gly Trp Tyr Arg Gln Ala Pro Gly Lys Gln Arg Glu Leu Val Ala
1               5                   10                  15

Ala Ile

<210> SEQ ID NO 78
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Tyr Ala Asp Ser Val Lys Gly Arg Phe Thr Ile Ser Arg Gly Asn Phe
1               5                   10                  15

Val Asn Thr Val Ala Leu Gln Met Asn Ser Leu Lys Ser Glu Asp Thr
            20                  25                  30
```

Ala Val Tyr Tyr Cys
        35

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Trp Gly Gln Gly Thr Gln Val Thr Val Ser Ser
1               5                   10

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Leu Gln Leu Val Glu Ser Gly Gly Gly Leu Val Gln Pro Gly Gly
1               5                   10                  15

Ser Leu Arg Leu Ser Cys Thr Ser Ala
            20                  25

<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ile Gly Trp Phe Arg Gln Ala Pro Gly Gln Lys Arg Glu Gly Val Ser
1               5                   10                  15

Leu Leu

<210> SEQ ID NO 82
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Tyr Ala Asp Ser Ala Arg Asp Arg Phe Thr Ile Ser Arg Asp Asn Ala
1               5                   10                  15

Arg Asn Thr Val Tyr Leu Gln Met Asn Ser Leu Lys Pro Glu Asp Thr
            20                  25                  30

Ala Val Tyr Ser Cys
        35

<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Trp Gly Lys Gly Thr Leu Val Thr Val Ser Ser
1               5                   10

<210> SEQ ID NO 84
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Val Gln Leu Ala Glu Ser Gly Gly Gly Leu Val Gln Pro Gly Gly
1               5                   10                  15

Ser Leu Arg Leu Ser Cys Ala Ala Ser
            20                  25

<210> SEQ ID NO 85
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ile Gly Trp Phe Arg Gln Ala Pro Gly Lys Gly Arg Glu Ala Val Ser
1               5                   10                  15

Ser Ile

<210> SEQ ID NO 86
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Tyr Ala Asn Ala Val Lys Gly Arg Phe Thr Ile Thr Arg Asp Asn Ala
1               5                   10                  15

Asn Asn Thr Val Tyr Leu Gln Met Asp Asn Leu Lys Pro Glu Asp Thr
            20                  25                  30

Ala Val Tyr Tyr Cys
        35

<210> SEQ ID NO 87
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gln Leu Gln Leu Val Glu Thr Gly Gly Leu Val Gln Ala Gly Gly Ser
1               5                   10                  15

Leu Arg Leu Ser Cys Val Gly Ser
            20

<210> SEQ ID NO 88
<211> LENGTH: 18

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Met Gly Trp Tyr Arg Gln Ala Pro Gly Thr Glu Arg Glu Leu Val Ala
1               5                   10                  15

Thr Trp

<210> SEQ ID NO 89
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Tyr Ala Asp Ser Val Lys Gly Arg Phe Thr Ile Ser Arg Asp Asn Leu
1               5                   10                  15

Lys Asn Thr Val Ser Leu Gln Met Asp Ser Leu Lys Pro Glu Asp Thr
            20                  25                  30

Ala Val Tyr Tyr Cys
        35

<210> SEQ ID NO 90
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Val Gln Leu Val Glu Ser Gly Gly Gly Leu Ala Gln Ala Gly Gly
1               5                   10                  15

Ser Leu Arg Leu Ser Cys Ala Ala Ser
            20                  25

<210> SEQ ID NO 91
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Met Gly Trp Tyr Arg Gln Pro Pro Gly Lys Gln Arg Glu Leu Val Ala
1               5                   10                  15

Thr Ile

<210> SEQ ID NO 92
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Tyr Ala Glu Ser Val Lys Gly Arg Phe Thr Ile Ser Arg Asp Asn Val
1               5                   10                  15
```

```
Lys Asn Thr Val His Leu Glu Met Asn Arg Leu Lys Ala Glu Asp Thr
            20                  25                  30

Ala Val Tyr Tyr Cys
        35

<210> SEQ ID NO 93
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Val Gln Leu Ala Glu Thr Gly Gly Gly Leu Val Gln Ala Gly Gly
1               5                   10                  15

Ser Leu Arg Leu Ser Cys Ala Ala Ser
            20                  25

<210> SEQ ID NO 94
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Met Ala Trp Tyr Arg Gln Val Pro Gly Lys Gln Arg Glu Leu Val Ala
1               5                   10                  15

Glu Ile

<210> SEQ ID NO 95
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Tyr Ser Asp Ser Val Thr Asp Arg Phe Ile Ile Ser Arg Asp Asn Thr
1               5                   10                  15

Lys Asn Thr Val Asp Leu Gln Met Asn Ser Leu Lys Pro Glu Asp Thr
            20                  25                  30

Ala Val Tyr Tyr Cys
        35

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Pro Gly Thr Gln Val Thr Val Ser Ser
1               5                   10

<210> SEQ ID NO 97
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 97

Gln Leu Gln Leu Ala Glu Ser Gly Gly Gly Leu Val Gln Pro Gly Gly
1               5                   10                  15

Ser Leu Arg Leu Ser Cys Ala Ala Ser
            20                  25

<210> SEQ ID NO 98
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Met Ser Trp Val Arg Gln Ala Pro Gly Lys Gly Leu Glu Trp Val Ser
1               5                   10                  15

Thr Ile

<210> SEQ ID NO 99
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Tyr Leu Asp Ser Val Lys Ser Arg Phe Thr Ile Ser Arg Asp Asn Ala
1               5                   10                  15

Lys Lys Thr Val Tyr Leu Gln Met Asn Ser Leu Lys Pro Glu Asp Thr
            20                  25                  30

Ala Val Tyr Tyr Cys
                35

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Gln Gly Thr Gln Val Thr Val Ser Ser
1               5                   10

<210> SEQ ID NO 101
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Leu Gln Leu Val Glu Ser Gly Gly Gly Leu Val Gln Pro Gly Gly
1               5                   10                  15

Ser Leu Arg Leu Ser Cys Val Ala Ser
            20                  25
```

<210> SEQ ID NO 102
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Met Ser Trp Val Arg Gln Ala Pro Gly Lys Gly Leu Glu Trp Val Ser
1               5                   10                  15

Ala Ile

<210> SEQ ID NO 103
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Tyr Ala Asp Phe Ala Lys Gly Arg Phe Thr Ile Ser Arg Asp Asn Ala
1               5                   10                  15

Lys Asn Thr Leu Tyr Leu Gln Met Asn Ser Leu Gln Leu Glu Asp Thr
                20                  25                  30

Ala Val Tyr Phe Cys
            35

<210> SEQ ID NO 104
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gln Val Gln Leu Val Glu Ser Gly Gly Gly Leu Val Gln Pro Gly Gly
1               5                   10                  15

Ser Leu Thr Ile Asn Cys Thr Val Ser
                20                  25

<210> SEQ ID NO 105
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Met Thr Trp Tyr Arg Gln Ala Pro Gly Lys Gln Arg Glu Leu Ala Ala
1               5                   10                  15

Asp Ile

<210> SEQ ID NO 106
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Tyr Leu Ala Ser Val Lys Gly Arg Phe Thr Ile Ser Arg Asp Asn Ala
1               5                   10                  15

Lys Ser Ala Leu Tyr Leu Gln Met Asn Ser Leu Lys Pro Glu Asp Thr
            20                  25                  30

Gly Thr Tyr Tyr Cys
            35

<210> SEQ ID NO 107
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Val Gln Leu Val Glu Thr Gly Gly Gly Leu Val Gln Ala Gly Gly
1               5                   10                  15

Ser Leu Arg Leu Ser Cys Ala Ala Ser
            20                  25

<210> SEQ ID NO 108
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Met Gly Trp Tyr Arg Gln Ala Pro Gly Asn Gln Arg Glu Phe Val Ala
1               5                   10                  15

Ser Ile

<210> SEQ ID NO 109
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Tyr Ala Asp Ser Val Ala Gly Arg Phe Ile Ile Ser Arg Asp Arg Gly
1               5                   10                  15

Lys Asn Thr Val Leu Ala Leu Gln Met Asp Ser Leu Lys Pro Glu Asp
            20                  25                  30

Thr Ala Val Tyr Tyr Cys
            35

<210> SEQ ID NO 110
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Val Gln Leu Ala Glu Thr Gly Gly Gly Leu Val Gln Ala Gly Gly
1               5                   10                  15

Ser Leu Arg Leu Ser Cys Val Ser Ser
            20                  25
```

<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Met Gly Trp Tyr Arg Gln Ala Pro Gly Ser Gln Arg Glu Leu Val Ala
1               5                   10                  15

Val

<210> SEQ ID NO 112
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Tyr Ala Asp Ser Val Lys Gly Arg Phe Thr Ile Ser Arg Asp Asn Leu
1               5                   10                  15

Lys Asn Thr Val Tyr Leu Gln Met Asn Ser Leu Lys Pro Glu Asp Ala
                20                  25                  30

Ala Val Tyr Tyr Cys
                35

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Trp Gly Gln Gly Thr Arg Val Thr Val Ser Ser
1               5                   10

<210> SEQ ID NO 114
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Q or V
<220> FEATURE:
<221> NAME/KEY: MOD_RES
<222> LOCATION: (11)..(11)
<223> OTHER INFORMATION: L or S
<220> FEATURE:
<221> NAME/KEY: MOD_RES
<222> LOCATION: (14)..(14)
<223> OTHER INFORMATION: A or P

<400> SEQUENCE: 114

Gln Val Gln Leu Xaa Glu Ser Gly Gly Gly Xaa Val Gln Xaa Gly Gly
1               5                   10                  15

Ser Leu Arg Leu Ser Cys Ala Ala Ser
                20                  25

<210> SEQ ID NO 115
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: S or T
<220> FEATURE:
<221> NAME/KEY: MOD_RES
<222> LOCATION: (9)..(9)
<223> OTHER INFORMATION: A or P
<220> FEATURE:
<221> NAME/KEY: MOD_RES
<222> LOCATION: (14)..(14)
<223> OTHER INFORMATION: R or T
<220> FEATURE:
<221> NAME/KEY: MOD_RES
<222> LOCATION: (15)..(15)
<223> OTHER INFORMATION: L or I
<220> FEATURE:
<221> NAME/KEY: MOD_RES
<222> LOCATION: (16)..(16)
<223> OTHER INFORMATION: S or N
<220> FEATURE:
<221> NAME/KEY: MOD_RES
<222> LOCATION: (18)..(18)
<223> OTHER INFORMATION: A, V or T
<220> FEATURE:
<221> NAME/KEY: MOD_RES
<222> LOCATION: (19)..(19)
<223> OTHER INFORMATION: A, G, V or S
<220> FEATURE:
<221> NAME/KEY: MOD_RES
<222> LOCATION: (20)..(20)
<223> OTHER INFORMATION: S or A

<400> SEQUENCE: 115

Glu Xaa Gly Gly Gly Leu Val Gln Xaa Gly Gly Ser Leu Xaa Xaa Xaa
1               5                   10                  15

Cys Xaa Xaa Xaa
            20

<210> SEQ ID NO 116
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: F, Y or V
<220> FEATURE:
<221> NAME/KEY: MOD_RES
<222> LOCATION: (9)..(9)
<223> OTHER INFORMATION: E, C or G
<220> FEATURE:
<221> NAME/KEY: MOD_RES
<222> LOCATION: (10)..(10)
<223> OTHER INFORMATION: R or L
<220> FEATURE:
<221> NAME/KEY: MOD_RES
<222> LOCATION: (12)..(12)
<223> OTHER INFORMATION: F, G, L or W
<220> FEATURE:
<221> NAME/KEY: MOD_RES
<222> LOCATION: (14)..(14)
<223> OTHER INFORMATION: A, S or T

<400> SEQUENCE: 116

Trp Xaa Arg Gln Ala Pro Gly Lys Xaa Xaa Glu Xaa Val Xaa
1               5                   10

<210> SEQ ID NO 117
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: F, Y or V
<220> FEATURE:
<221> NAME/KEY: MOD_RES
<222> LOCATION: (5)..(5)
<223> OTHER INFORMATION: A or P
<220> FEATURE:
<221> NAME/KEY: MOD_RES
<222> LOCATION: (8)..(8)
<223> OTHER INFORMATION: K, S or Q
<220> FEATURE:
<221> NAME/KEY: MOD_RES
<222> LOCATION: (9)..(9)
<223> OTHER INFORMATION: Q, G, E, K or T
<220> FEATURE:
<221> NAME/KEY: MOD_RES
<222> LOCATION: (10)..(10)
<223> OTHER INFORMATION: R or L
<220> FEATURE:
<221> NAME/KEY: MOD_RES
<222> LOCATION: (12)..(12)
<223> OTHER INFORMATION: L, W or G
<220> FEATURE:
<221> NAME/KEY: MOD_RES
<222> LOCATION: (13)..(13)
<223> OTHER INFORMATION: V or D
<220> FEATURE:
<221> NAME/KEY: MOD_RES
<222> LOCATION: (14)..(14)
<223> OTHER INFORMATION: A or S

<400> SEQUENCE: 117

Trp Xaa Arg Gln Xaa Pro Gly Xaa Xaa Xaa Glu Xaa Xaa Xaa
1               5                   10

<210> SEQ ID NO 118
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: A, Q, T or V
<220> FEATURE:
<221> NAME/KEY: MOD_RES
<222> LOCATION: (3)..(3)
<223> OTHER INFORMATION: D or E
<220> FEATURE:
<221> NAME/KEY: MOD_RES
<222> LOCATION: (5)..(5)
<223> OTHER INFORMATION: V or A
<220> FEATURE:
<221> NAME/KEY: MOD_RES
<222> LOCATION: (10)..(10)
<223> OTHER INFORMATION: T or A
<220> FEATURE:
<221> NAME/KEY: MOD_RES
<222> LOCATION: (11)..(11)
<223> OTHER INFORMATION: I or V

```
<220> FEATURE:
<221> NAME/KEY: MOD_RES
<222> LOCATION: (13)..(13)
<223> OTHER INFORMATION: R or Q
<220> FEATURE:
<221> NAME/KEY: MOD_RES
<222> LOCATION: (15)..(15)
<223> OTHER INFORMATION: N or K
<220> FEATURE:
<221> NAME/KEY: MOD_RES
<222> LOCATION: (17)..(17)
<223> OTHER INFORMATION: K or A
<220> FEATURE:
<221> NAME/KEY: MOD_RES
<222> LOCATION: (20)..(20)
<223> OTHER INFORMATION: V, L or M
<220> FEATURE:
<221> NAME/KEY: MOD_RES
<222> LOCATION: (25)..(25)
<223> OTHER INFORMATION: N or D
<220> FEATURE:
<221> NAME/KEY: MOD_RES
<222> LOCATION: (26)..(26)
<223> OTHER INFORMATION: S or N
<220> FEATURE:
<221> NAME/KEY: MOD_RES
<222> LOCATION: (28)..(28)
<223> OTHER INFORMATION: K or R
<220> FEATURE:
<221> NAME/KEY: MOD_RES
<222> LOCATION: (30)..(30)
<223> OTHER INFORMATION: E or D
<220> FEATURE:
<221> NAME/KEY: MOD_RES
<222> LOCATION: (33)..(33)
<223> OTHER INFORMATION: A or G
<220> FEATURE:
<221> NAME/KEY: MOD_RES
<222> LOCATION: (34)..(34)
<223> OTHER INFORMATION: V, I, T or M

<400> SEQUENCE: 118

Tyr Xaa Xaa Ser Xaa Lys Gly Arg Phe Xaa Xaa Ser Xaa Asp Xaa Ala
1               5                   10                  15

Xaa Asn Thr Xaa Tyr Leu Gln Met Xaa Xaa Leu Xaa Pro Xaa Asp Thr
            20                  25                  30

Xaa Xaa Tyr Tyr Cys
        35

<210> SEQ ID NO 119
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: A, L or S
<220> FEATURE:
<221> NAME/KEY: MOD_RES
<222> LOCATION: (3)..(3)
<223> OTHER INFORMATION: D, N, A or E
<220> FEATURE:
<221> NAME/KEY: MOD_RES
<222> LOCATION: (4)..(4)
<223> OTHER INFORMATION: S, F or A
<220> FEATURE:
<221> NAME/KEY: MOD_RES
<222> LOCATION: (5)..(5)
<223> OTHER INFORMATION: V or A
<220> FEATURE:
<221> NAME/KEY: MOD_RES
<222> LOCATION: (6)..(6)
```

```
<223> OTHER INFORMATION: K, R or T
<220> FEATURE:
<221> NAME/KEY: MOD_RES
<222> LOCATION: (7)..(7)
<223> OTHER INFORMATION: G, S or D
<220> FEATURE:
<221> NAME/KEY: MOD_RES
<222> LOCATION: (10)..(10)
<223> OTHER INFORMATION: T or I
<220> FEATURE:
<221> NAME/KEY: MOD_RES
<222> LOCATION: (12)..(12)
<223> OTHER INFORMATION: S or T
<220> FEATURE:
<221> NAME/KEY: MOD_RES
<222> LOCATION: (14)..(14)
<223> OTHER INFORMATION: D or G
<220> FEATURE:
<221> NAME/KEY: MOD_RES
<222> LOCATION: (15)..(15)
<223> OTHER INFORMATION: N or S
<220> FEATURE:
<221> NAME/KEY: MOD_RES
<222> LOCATION: (16)..(16)
<223> OTHER INFORMATION: A, L, T, V, F or P
<220> FEATURE:
<221> NAME/KEY: MOD_RES
<222> LOCATION: (17)..(17)
<223> OTHER INFORMATION: K, N or V
<220> FEATURE:
<221> NAME/KEY: MOD_RES
<222> LOCATION: (18)..(18)
<223> OTHER INFORMATION: N, K or S
<220> FEATURE:
<221> NAME/KEY: MOD_RES
<222> LOCATION: (19)..(19)
<223> OTHER INFORMATION: T or A
<220> FEATURE:
<221> NAME/KEY: MOD_RES
<222> LOCATION: (20)..(20)
<223> OTHER INFORMATION: V or L
<220> FEATURE:
<221> NAME/KEY: MOD_RES
<222> LOCATION: (21)..(21)
<223> OTHER INFORMATION: Y, H, D or S
<220> FEATURE:
<221> NAME/KEY: MOD_RES
<222> LOCATION: (23)..(23)
<223> OTHER INFORMATION: Q or E
<220> FEATURE:
<221> NAME/KEY: MOD_RES
<222> LOCATION: (25)..(25)
<223> OTHER INFORMATION: N or D
<220> FEATURE:
<221> NAME/KEY: MOD_RES
<222> LOCATION: (26)..(26)
<223> OTHER INFORMATION: S, N, R or E
<220> FEATURE:
<221> NAME/KEY: MOD_RES
<222> LOCATION: (28)..(28)
<223> OTHER INFORMATION: K or Q
<220> FEATURE:
<221> NAME/KEY: MOD_RES
<222> LOCATION: (29)..(29)
<223> OTHER INFORMATION: P, L, S or V
<220> FEATURE:
<221> NAME/KEY: MOD_RES
<222> LOCATION: (33)..(33)
<223> OTHER INFORMATION: A or G
<220> FEATURE:
<221> NAME/KEY: MOD_RES
<222> LOCATION: (34)..(34)
<223> OTHER INFORMATION: V or T
<220> FEATURE:
<221> NAME/KEY: MOD_RES
<222> LOCATION: (36)..(36)
<223> OTHER INFORMATION: Y, F or S

<400> SEQUENCE: 119
```

Tyr Xaa Xaa Xaa Xaa Xaa Arg Phe Xaa Ile Xaa Arg Xaa Xaa Xaa
1               5                   10                  15

Xaa Xaa Xaa Xaa Xaa Leu Xaa Met Xaa Xaa Leu Xaa Xaa Glu Asp Thr
                20                  25                  30

Xaa Xaa Tyr Xaa Cys
        35

<210> SEQ ID NO 120
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Val Gln Leu Ala Glu Ser Gly Gly Gly Leu Val Gln Ala Gly Gly
1               5                   10                  15

Ser Leu Arg Leu Ser Cys Ala Ala Ser Gly Ser Val Tyr Thr Phe Met
                20                  25                  30

Gly Trp Tyr Arg Gln Ala Pro Gly Lys Thr Arg Glu Leu Val Ala Gly
            35                  40                  45

Ile Ser Gly Gly Thr Ile Thr Lys Tyr Ala Asp Ser Val Lys Gly Arg
    50                  55                  60

Phe Ile Ile Ser Arg Asp Ser Pro Lys Asn Thr Ile Tyr Leu Gln Met
65                  70                  75                  80

Asn Glu Leu Lys Val Glu Asp Thr Gly Val Tyr Tyr Cys Asn Ala Gly
                85                  90                  95

Asp Thr Ile Ala Gln Ala Met Gly Thr Arg Arg Phe Pro Phe Asp Arg
            100                 105                 110

Trp Gly Gln Gly Thr Gln Val Thr Val Ala Ser
            115                 120

<210> SEQ ID NO 121
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Ser Gly Gly Gly Leu Val Gln Ala Gly Gly Ser Leu Arg Leu Ser Cys
1               5                   10                  15

Val Gly Ser Gly Arg Gly Pro Gly Ile Asn Val Met Gly Trp Tyr Arg
                20                  25                  30

Gln Ala Pro Gly Thr Glu Arg Glu Leu Val Ala Thr Trp Gln Thr Gly
            35                  40                  45

Gly Thr Thr Asn Tyr Ala Asp Ser Val Lys Gly Arg Phe Thr Ile Ser
    50                  55                  60

Arg Asp Asn Leu Lys Asn Thr Val Ser Leu Gln Met Asp Ser Leu Lys
65                  70                  75                  80

Pro Glu Asp Thr Ala Val Tyr Tyr Cys Tyr Leu Lys Lys Trp Arg Asp
                85                  90                  95

Glu Tyr Trp Gly Gln Gly Thr Gln Val Thr Val Ser Ser
            100                 105

<210> SEQ ID NO 122

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: W or R
<220> FEATURE:
<221> NAME/KEY: MOD_RES
<222> LOCATION: (3)..(3)
<223> OTHER INFORMATION: Q, K or P
<220> FEATURE:
<221> NAME/KEY: MOD_RES
<222> LOCATION: (6)..(6)
<223> OTHER INFORMATION: Q or L
<220> FEATURE:
<221> NAME/KEY: MOD_RES
<222> LOCATION: (10)..(10)
<223> OTHER INFORMATION: S or A

<400> SEQUENCE: 122

Xaa Gly Xaa Gly Thr Xaa Val Thr Val Xaa Ser
1               5                   10

<210> SEQ ID NO 123
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Any amino acid
<220> FEATURE:
<221> NAME/KEY: MOD_RES
<222> LOCATION: (45)..(45)
<223> OTHER INFORMATION: Any amino acid
<220> FEATURE:
<221> NAME/KEY: MOD_RES
<222> LOCATION: (83)..(83)
<223> OTHER INFORMATION: Any amino acid

<400> SEQUENCE: 123

Ser Gly Gly Gly Leu Val Gln Ala Gly Gly Ser Leu Arg Leu Ser Cys
1               5                   10                  15

Ala Ala Ser Gly Thr Val Tyr Thr Phe Met Gly Trp Tyr Arg His Pro
            20                  25                  30

Pro Ser Lys Thr Xaa Gln Leu Asp Ser Gly Ile Tyr Xaa Gly Thr Ile
        35                  40                  45

Ala Asn Tyr Ala Tyr Ser Glu Asn Gly Gln Val Leu Phe Ser Ile Tyr
    50                  55                  60

Arg Arg Asn Asn Thr Ile Tyr Leu His Met Asn Glu Ile Lys Leu Glu
65                  70                  75                  80

Asp Thr Xaa Val Tyr Tyr Cys Tyr Ala Ser Tyr Thr Ile Ala Gln Ala
                85                  90                  95

Met Gly Thr Arg Arg Phe Pro Ile His Arg Trp Gly Pro Gly Asn Pro
            100                 105                 110

Val Thr Val Ala Ser
        115

<210> SEQ ID NO 124
<211> LENGTH: 109
<212> TYPE: PRT
```

<213> ORGANISM: Artificial Sequence
<220> FEATURE:
<223> OTHER INFORMATION: Description of Artificial Sequence: Synthetic
     polypeptide

<400> SEQUENCE: 124

Ser Gly Gly Gly Leu Val Gln Ala Gly Gly Ser Leu Arg Leu Ser Cys
1               5                   10                  15

Ala Thr Ser Gly Ala Asn Leu Gly Ile Asn Ala Met Gly Trp Tyr Arg
            20                  25                  30

Gln Ala Pro Gly Ser Gln Arg Glu Leu Val Ala Thr Trp Gln Thr Gly
        35                  40                  45

Gly Ser Thr Asn Tyr Ala Asp Ser Val Lys Gly Arg Ala Thr Ile Ser
    50                  55                  60

Arg Asp Thr Ala Lys Asn Thr Val Asn Leu Gln Met Asn Ser Leu Lys
65                  70                  75                  80

Pro Glu Asp Thr Ala Val Tyr Tyr Cys Tyr Leu Lys Arg Trp Arg Asn
                85                  90                  95

Asp Tyr Trp Gly Gln Gly Thr Gln Val Thr Val Tyr Ser
            100                 105

<210> SEQ ID NO 125
<211> LENGTH: 108
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 125

Thr Gly Gly Leu Val Gln Ala Gly Gly Ser Leu Arg Leu Ser Cys Val
1               5                   10                  15

Gly Ser Gly Arg Gly Pro Gly Ile Asn Val Met Gly Trp Tyr Arg Gln
            20                  25                  30

Ala Pro Gly Thr Glu Arg Glu Leu Val Ala Thr Trp Gln Thr Gly Gly
        35                  40                  45

Thr Thr Asn Tyr Ala Asp Ser Val Lys Gly Arg Phe Thr Ile Ser Arg
    50                  55                  60

Asp Asn Leu Lys Asn Thr Val Ser Leu Gln Met Asp Ser Leu Lys Pro
65                  70                  75                  80

Glu Asp Thr Ala Val Tyr Tyr Cys Tyr Leu Lys Lys Trp Arg Asp Glu
                85                  90                  95

Tyr Trp Gly Gln Gly Thr Gln Val Thr Val Ser Ser
            100                 105

<210> SEQ ID NO 126
<211> LENGTH: 109
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 126

Thr Gly Gly Gly Leu Val Gln Ala Gly Gly Ser Leu Arg Leu Ser Cys
1               5                   10                  15

Val Ser Ser Glu Arg Asn Pro Gly Ile Asn Ala Met Gly Trp Tyr Arg
            20                  25                  30

Gln Ala Pro Gly Gly Gln Arg Glu Leu Val Ala Val Trp Gln Thr Gly
        35                  40                  45

```
Gly Ser Leu Asn Tyr Ala Asp Ser Val Lys Gly Arg Phe Thr Ile Ser
        50                  55                  60

Arg Asp Asn Leu Lys Asn Thr Val Tyr Leu Gln Met Asn Ser Leu Lys
 65                  70                  75                  80

Pro Glu Asp Thr Ala Val Tyr Tyr Cys Tyr Leu Lys Lys Trp Arg Asp
                 85                  90                  95

Gln Tyr Trp Gly Gln Gly Thr Gln Val Thr Val Ser Ser
            100                 105
```

<210> SEQ ID NO 127
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Thr Gly Gly Gly Leu Val Gln Ala Gly Gly Ser Leu Arg Leu Ser Cys
 1               5                  10                  15

Val Ser Ser Glu Arg Asn Pro Gly Ile Asn Ala Met Gly Trp Tyr Arg
                 20                  25                  30

Gln Ala Pro Gly Ser Gln Arg Glu Leu Val Ala Val Trp Gln Thr Gly
             35                  40                  45

Gly Ser Leu Asn Tyr Ala Asp Ser Val Lys Gly Arg Phe Thr Ile Ser
        50                  55                  60

Arg Asp Asn Leu Lys Asn Thr Val Tyr Leu Gln Met Asn Ser Leu Lys
 65                  70                  75                  80

Pro Glu Asp Thr Ala Val Tyr Tyr Cys Tyr Leu Lys Lys Trp Arg Asp
                 85                  90                  95

Gln Tyr Trp Gly Gln Gly Thr Gln Val Thr Val Ser Ser
            100                 105
```

<210> SEQ ID NO 128
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

```
Thr Gly Gly Gly Leu Val Gln Ala Gly Gly Ser Leu Arg Leu Ser Cys
 1               5                  10                  15

Val Ser Ser Glu Arg Asn Pro Gly Ile Asn Ala Met Gly Trp Tyr Arg
                 20                  25                  30

Ala Pro Gly Ser Gln Arg Glu Leu Val Ala Val Trp Gln Thr Gly Gly
             35                  40                  45

Ser Leu Asn Tyr Ala Asp Phe Val Lys Gly Arg Phe Thr Ile Ser Arg
         50                  55                  60

Asp Asn Leu Lys Asn Thr Val Tyr Leu Gln Met Asn Ser Leu Lys Pro
 65                  70                  75                  80

Glu Asp Thr Ala Val Tyr Tyr Cys Tyr Leu Lys Lys Trp Arg Asp Gln
                 85                  90                  95

Tyr Trp Gly Gln Gly Thr Arg Val Thr Val Ser Ser
            100                 105
```

<210> SEQ ID NO 129

<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Ser Gly Gly Gly Leu Val Gln Ala Gly Gly Ser Leu Arg Leu Ser Cys
1               5                   10                  15

Val Gly Ser Gly Arg Asn Pro Gly Ile Asn Ala Met Gly Trp Tyr Arg
            20                  25                  30

Gln Ala Pro Gly Ser Gln Arg Glu Leu Val Ala Val Trp Gln Thr Gly
        35                  40                  45

Gly Ser Thr Asn Tyr Ala Asp Ser Val Lys Gly Arg Phe Thr Ile Ser
    50                  55                  60

Arg Asp Asn Leu Lys Asn Thr Val Tyr Leu Gln Met Asn Ser Leu Lys
65                  70                  75                  80

Pro Glu Asp Thr Ala Val Tyr Tyr Cys Tyr Leu Lys Lys Trp Arg Asp
                85                  90                  95

Glu Tyr Trp Gly Gln Gly Thr Gln Val Thr Val Ser Ser
            100                 105

<210> SEQ ID NO 130
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Thr Gly Gly Gly Leu Val Gln Ala Gly Gly Ser Leu Arg Leu Ser Cys
1               5                   10                  15

Val Gly Ser Gly Arg Asn Pro Gly Ile Asn Ala Met Gly Trp Tyr Arg
            20                  25                  30

Gln Ala Pro Gly Ser Gln Arg Glu Leu Val Ala Val Trp Gln Thr Gly
        35                  40                  45

Gly Ser Thr Asn Tyr Ala Asp Ser Val Lys Gly Arg Phe Thr Ile Ser
    50                  55                  60

Arg Asp Asn Leu Lys Asn Thr Val Tyr Leu Gln Met Asn Ser Leu Lys
65                  70                  75                  80

Pro Glu Asp Thr Ala Val Tyr Tyr Cys Tyr Leu Lys Lys Trp Arg Asp
                85                  90                  95

Glu Tyr Trp Gly Gln Gly Thr Gln Val Thr Val Ser Ser
            100                 105

<210> SEQ ID NO 131
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Thr Gly Gly Gly Leu Val Gln Ala Gly Gly Ser Leu Arg Leu Ser Cys
1               5                   10                  15

Val Gly Ser Gly Arg Asn Pro Gly Ile Asn Ala Met Gly Trp Tyr Arg
            20                  25                  30

Gln Ala Pro Gly Ser Gln Arg Glu Leu Val Ala Val Trp Gln Thr Gly
            35                  40                  45

Gly Arg Thr Asn Tyr Ala Asp Ser Val Lys Gly Arg Phe Thr Ile Ser
 50                  55                  60

Arg Asp Asn Leu Lys Asn Thr Val Tyr Leu Gln Met Asn Ser Leu Lys
 65                  70                  75                  80

Pro Glu Asp Thr Ala Val Tyr Tyr Cys Tyr Leu Lys Lys Trp Arg Asp
                 85                  90                  95

Glu Tyr Trp Gly Gln Gly Thr Gln Val Thr Val Ser Ser
            100                 105

<210> SEQ ID NO 132
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Ser Gly Gly Gly Leu Val Gln Pro Gly Gly Ser Leu Arg Leu Ser Cys
 1               5                   10                  15

Ala Ala Ser Gly Ile Thr Phe Ser Asn Val Ala Met Ser Trp Val Arg
                20                  25                  30

Gln Ala Pro Gly Lys Gly Leu Glu Trp Val Ser Thr Ile Ser Thr Gly
            35                  40                  45

Gly Ser Ser Thr Ser Tyr Leu Asp Ser Val Lys Ser Arg Phe Thr Ile
 50                  55                  60

Ser Arg Asp Asn Ala Lys Lys Thr Val Tyr Leu Gln Met Asn Ser Leu
 65                  70                  75                  80

Lys Pro Glu Asp Thr Ala Val Tyr Tyr Cys Val Lys Gly Pro Lys Tyr
                 85                  90                  95

Ser Ala Thr Ile Arg Arg Pro Glu Gly Gln Gly Thr Gln Val Thr Val
                100                 105                 110

Ser Ser

<210> SEQ ID NO 133
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Ser Gly Gly Gly Leu Val Gln Pro Gly Gly Ser Leu Arg Leu Ser Cys
 1               5                   10                  15

Ala Ala Ser Gly Phe Thr Phe Ser Asn Val Ala Met Ser Trp Val Arg
                20                  25                  30

Gln Ala Pro Gly Lys Gly Leu Glu Trp Val Ser Thr Ile Ser Thr Gly
            35                  40                  45

Gly Thr Ser Thr Ala Tyr Leu Asp Ser Val Lys Gly Arg Phe Thr Ile
 50                  55                  60

Phe Arg Asp Asn Ala Lys Asn Thr Ala Tyr Leu Gln Met Asn Ser Leu
 65                  70                  75                  80

Lys Pro Glu Asp Thr Ala Met Tyr Tyr Cys Ala Asn Gln Pro Lys Ala
                 85                  90                  95

Leu Ser Thr Ile Ser Arg Pro Lys Gly Gln Gly Thr Gln Val Thr Val

Ser Ser

<210> SEQ ID NO 134
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Thr Gly Gly Gly Ser Val Gln Ile Gly Gly Ser Leu Arg Leu Ser Cys
1               5                   10                  15

Val Thr Ser Gly Phe Thr Phe Ser Lys Asn Ile Met Ser Trp Val Arg
            20                  25                  30

Gln Ala Pro Gly Lys Gly Leu Glu Trp Val Ser Thr Ile Ser Ile Gly
        35                  40                  45

Gly Ala Ala Thr Ser Tyr Ala Asp Ser Val Lys Gly Arg Phe Thr Ile
    50                  55                  60

Ser Arg Asp Asn Ala Asn Asp Thr Leu Tyr Leu Gln Met Asn Asp Leu
65                  70                  75                  80

Lys Pro Glu Asp Thr Ala Val Tyr Tyr Cys Ser Arg Gly Pro Arg Thr
                85                  90                  95

Tyr Ile Asn Thr Ala Ser Arg Gly Gln Gly Thr Gln Val Thr Val Ser
            100                 105                 110

Thr

<210> SEQ ID NO 135
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Ser Gly Gly Gly Leu Val Gln Pro Gly Gly Ser Leu Arg Leu Ser Cys
1               5                   10                  15

Ala Ala Ser Gly Phe Thr Phe Ser Lys Asn Ile Met Ser Trp Val Arg
            20                  25                  30

Gln Ala Pro Gly Lys Gly Leu Glu Trp Val Ser Ala Ile Ser Ile Gly
        35                  40                  45

Gly Val Ser Thr Ser Tyr Ala Asp Ser Val Lys Gly Arg Phe Thr Ile
    50                  55                  60

Ser Arg Asp Asn Ala Lys Asn Thr Leu Tyr Leu Gln Met Asn Ser Leu
65                  70                  75                  80

Lys Pro Glu Asp Thr Ala Val Tyr Phe Cys Val Lys Gly Pro Arg Ser
                85                  90                  95

Ala Ser Gly Asn Ser Asp Asn Arg Gly Lys Gly Thr Leu Val Thr Val
            100                 105                 110

Ser Ser

<210> SEQ ID NO 136
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 136

```
Thr Gly Gly Gly Leu Val Gln Pro Gly Gly Ser Leu Arg Leu Ser Cys
1               5                   10                  15

Val Ala Ser Gly Phe Thr Phe Ser Val Gln Ile Met Ser Trp Val Arg
            20                  25                  30

Gln Ala Pro Gly Lys Gly Leu Glu Trp Val Ser Thr Ile Ser Asn Gly
        35                  40                  45

Gly Val Ser Thr Ser Tyr Ala Asp Ser Ala Lys Gly Arg Phe Thr Ile
    50                  55                  60

Ser Arg Asp Asn Ala Lys Asn Thr Leu Tyr Leu Gln Met Asn Ser Leu
65                  70                  75                  80

Lys Pro Glu Asp Thr Ala Val Tyr Tyr Cys Leu Lys Gly Pro Pro Ser
                85                  90                  95

Trp Ile Asn Ser Ala Ser Arg Gly Gln Gly Thr Gln Val Thr Val Ser
            100                 105                 110

Ser
```

<210> SEQ ID NO 137
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (46)..(46)
<223> OTHER INFORMATION: Any amino acid

<400> SEQUENCE: 137

```
Ser Gly Gly Gly Leu Val Gln Pro Gly Gly Ser Leu Arg Leu Ser Cys
1               5                   10                  15

Val Ala Ser Gly Phe Asn Phe Ser Val Gln Ile Met Ser Trp Val Arg
            20                  25                  30

Gln Ala Pro Gly Lys Gly Leu Glu Trp Val Ser Ala Ile Xaa Thr Gly
        35                  40                  45

Gly Ala Ser Lys Ser Tyr Ala Asp Phe Ala Lys Gly Arg Phe Thr Ile
    50                  55                  60

Ser Arg Asp Asn Ala Lys Asn Thr Leu Tyr Leu Gln Met Asn Ser Leu
65                  70                  75                  80

Gln Leu Glu Asp Thr Ala Val Tyr Phe Cys Ser Lys Gly Pro Arg Thr
                85                  90                  95

Trp Ile Asn Ser Ser Pro Arg Gly Gln Gly Thr Gln Val Thr Val Ser
            100                 105                 110

Ser
```

<210> SEQ ID NO 138
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

```
Ser Gly Gly Gly Leu Val Gln Pro Gly Gly Ser Leu Arg Leu Ser Cys
1               5                   10                  15
```

```
Thr Ser Ala Arg Phe Ser Leu Ile Asn Tyr Ala Ile Gly Trp Phe Arg
            20                  25                  30

Gln Ala Pro Gly Gln Lys Arg Glu Gly Val Ser Leu Leu Thr Ser Gly
        35                  40                  45

Gly Ala Thr Tyr Tyr Ala Asp Ser Ala Arg Asp Arg Phe Thr Ile Ser
    50                  55                  60

Arg Asp Asn Ala Arg Asn Thr Val Tyr Leu Gln Met Asn Ser Leu Lys
65                  70                  75                  80

Pro Glu Asp Thr Ala Val Tyr Ser Cys Ala Ala Gly Pro Tyr Ser Arg
                85                  90                  95

Thr Leu Val Ser Arg Trp Lys Val Gly Asp Gly Met Glu Tyr Trp Gly
            100                 105                 110

Lys Gly Thr Leu Val Thr Val Ser Ser
        115                 120

<210> SEQ ID NO 139
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Ser Gly Gly Gly Leu Val Gln Pro Gly Gly Ser Leu Arg Leu Ser Cys
1               5                   10                  15

Ala Ala Ser Gly Phe Thr Ser Asn Ser Tyr Tyr Ile Gly Trp Phe Arg
            20                  25                  30

Gln Ala Pro Gly Lys Gly Arg Glu Ala Val Ser Ser Ile Ser Ser Ser
        35                  40                  45

Gly Gly Ser Pro Asn Tyr Ala Asn Ala Val Lys Gly Arg Phe Thr Ile
    50                  55                  60

Thr Arg Asp Asn Ala Asn Asn Thr Val Tyr Leu Gln Met Asp Asn Leu
65                  70                  75                  80

Lys Pro Glu Asp Thr Ala Val Tyr Tyr Cys Ala Ala Ser Lys Phe Pro
                85                  90                  95

Leu Thr Thr Met Ala Ser Asn Arg Tyr His Tyr Trp Gly Gln Gly Thr
            100                 105                 110

Gln Val Thr Val Ser Ser
        115

<210> SEQ ID NO 140
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gly Gly Gly Leu Val Gln Ala Gly Gly Ser Leu Thr Ile Asn Cys Thr
1               5                   10                  15

Val Ser Gly Thr Ala Phe Ser Leu Asp Thr Met Thr Trp Tyr Arg Gln
            20                  25                  30

Ala Pro Gly Lys Gln Arg Glu Leu Val Ala Asp Ile Ser Ser Ser Gly
        35                  40                  45

Ala Ser Asn Tyr Leu Ala Ser Val Lys Gly Arg Phe Thr Ile Ser Arg
    50                  55                  60
```

Asp Asn Ala Lys Ser Ala Leu Tyr Leu Gln Met Asn Ser Leu Lys Pro
65                  70                  75                  80

Glu Asp Thr Gly Thr Tyr Tyr Cys Tyr Arg Gly Arg Val Arg Gly Val
            85                  90                  95

Trp Pro Leu Asp Ser Gly Met Met Tyr Trp Gly Lys Gly Thr Leu Val
            100                 105                 110

Thr Val Ser Ser
        115

<210> SEQ ID NO 141
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Thr Gly Gly Gly Leu Val Gln Ala Gly Gly Ser Leu Arg Leu Ser Cys
1               5                   10                  15

Ala Ala Ser Gly Arg Leu Ser Glu Arg Ile Phe Met Ile Ser Thr Met
            20                  25                  30

Ala Trp Tyr Arg Gln Val Pro Gly Lys Gln Arg Glu Leu Val Ala Glu
            35                  40                  45

Ile Ser Arg Leu Gly Arg Ala Asn Tyr Ser Asp Ser Val Thr Asp Arg
50                  55                  60

Phe Ile Ile Ser Arg Asp Asn Thr Lys Asn Thr Val Asp Leu Gln Met
65                  70                  75                  80

Asn Ser Leu Lys Pro Glu Asp Thr Ala Val Tyr Tyr Cys Asn Leu Lys
            85                  90                  95

Pro Phe Val Asp Asn Tyr Arg Gly Pro Gly Thr Gln Val Thr Val Ser
            100                 105                 110

Ser

<210> SEQ ID NO 142
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Ser Gly Gly Gly Leu Ala Gln Ala Gly Gly Ser Leu Arg Leu Ser Cys
1               5                   10                  15

Ala Ala Ser Gly Ser Ser Phe Ser Met Asn Val Met Gly Trp Tyr Arg
            20                  25                  30

Gln Pro Pro Gly Lys Gln Arg Glu Leu Val Ala Thr Ile Arg Ser Asp
            35                  40                  45

Gly Ile Thr Asn Tyr Ala Glu Ser Val Lys Gly Arg Phe Thr Ile Ser
50                  55                  60

Arg Asp Asn Val Lys Asn Thr Val His Leu Glu Met Asn Arg Leu Lys
65                  70                  75                  80

Ala Glu Asp Thr Ala Val Tyr Tyr Cys Phe His Gly Arg Ala Arg Thr
            85                  90                  95

Gly Asn Asn Ala Asp Leu Gly Ser Trp Gly Gln Gly Thr Gln Val Thr
            100                 105                 110

Val Ser Ser

<210> SEQ ID NO 143
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Ser Gly Gly Gly Leu Val Gln Ala Gly Gly Ser Leu Arg Leu Ser Cys
1               5                   10                  15

Ala Ala Ser Gly Asn Ser Tyr Ala Arg Asn Tyr Met Gly Trp Phe Arg
            20                  25                  30

Gln Ala Pro Gly Lys Gln Arg Glu Leu Val Ala Glu Ile Thr Pro Ala
        35                  40                  45

Gly Asp Thr Asn Tyr Ala His Phe Val Lys Gly Arg Phe Thr Thr Ser
    50                  55                  60

Arg Gly Asn Ala Val Asn Thr Val Ser Leu Gln Met Asn Ser Leu Glu
65                  70                  75                  80

Pro Glu Asp Thr Ala Val Tyr Tyr Cys Lys Leu Val Asp Leu Arg Arg
                85                  90                  95

Asn Ala Tyr Trp Gly Gln Gly Thr Gln Val Thr Val Ser Ser
            100                 105                 110

<210> SEQ ID NO 144
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Ser Gly Gly Gly Leu Val Gln Ala Gly Gly Ser Leu Arg Leu Ser Cys
1               5                   10                  15

Val Gly Ser Gly Thr Ser Phe Pro Arg Asn Tyr Met Gly Trp Tyr Arg
            20                  25                  30

Gln Ala Pro Gly Lys Gln Arg Glu Leu Val Ala Ala Ile Ser His Asp
        35                  40                  45

Gly Asn Val Glu Tyr Ala Asp Ser Val Lys Gly Arg Phe Thr Ile Ser
    50                  55                  60

Arg Gly Asn Phe Val Asn Thr Val Ala Leu Gln Met Asn Ser Leu Lys
65                  70                  75                  80

Ser Glu Asp Thr Ala Val Tyr Tyr Cys Lys Leu Val Thr Leu Arg Arg
                85                  90                  95

Asp Glu Tyr Trp Gly Gln Gly Thr Gln Val Thr Val Ser Ser
            100                 105                 110

<210> SEQ ID NO 145
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Ser Gly Gly Asp Leu Val Gln Ala Gly Gly Ser Leu Arg Leu Ser Cys
1               5                   10                  15

Val Gly Ser Gly Thr Ser Phe Pro Arg Asn Tyr Met Gly Trp Tyr Arg
            20                  25                  30

Gln Thr Pro Gly Lys Gln Arg Glu Leu Val Ala Asp Ile Thr Arg Asp
            35                  40                  45

Asp Asn Thr Asn Tyr Ala Asp Ser Val Lys Gly Arg Phe Thr Ile Ser
        50                  55                  60

Arg Gly Asn Ala Val Asn Thr Val His Leu Gln Met Asn Ser Leu Lys
65                  70                  75                  80

Ala Glu Asp Thr Ala Val Tyr Tyr Cys Lys Leu Ala Thr Leu Arg Gly
                85                  90                  95

Asp Gln Tyr Trp Gly Gln Gly Thr Gln Val Thr Val Ser Ser
            100                 105                 110

<210> SEQ ID NO 146
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Ser Gly Gly Gly Leu Val Gln Ala Gly Gly Ser Leu Arg Leu Ser Cys
1               5                   10                  15

Ala Ala Ser Gly Ser Val Tyr Thr Phe Met Gly Trp Tyr Arg Gln Ala
            20                  25                  30

Pro Gly Lys Thr Arg Glu Leu Val Ala Gly Ile Ser Gly Gly Thr Ile
            35                  40                  45

Thr Lys Tyr Ala Asp Ser Val Lys Gly Arg Phe Ile Ile Ser Arg Asp
        50                  55                  60

Ser Pro Lys Asn Thr Ile Tyr Leu Gln Met Asn Glu Leu Lys Val Glu
65                  70                  75                  80

Asp Thr Gly Val Tyr Tyr Cys Asn Ala Gly Asp Thr Ile Ala Gln Ala
                85                  90                  95

Met Gly Thr Arg Arg Phe Pro Phe Asp Arg Trp Gly Gln Gly Thr Gln
            100                 105                 110

Val Thr Val Ala Ser
        115

<210> SEQ ID NO 147
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Ser Gly Gly Gly Leu Val Gln Ala Gly Gly Ser Leu Arg Leu Ser Cys
1               5                   10                  15

Val Ser Ser Glu Arg Asn Pro Gly Ile Asn Ala Met Gly Trp Tyr Arg
            20                  25                  30

Gln Ala Pro Gly Ser Gln Arg Glu Leu Val Ala Val Trp Gln Thr Gly
            35                  40                  45

Gly Ser Leu Asn Tyr Ala Asp Ser Val Lys Gly Arg Phe Thr Ile Ser
        50                  55                  60

Arg Asp Asn Leu Lys Asn Thr Val Tyr Leu Gln Met Asn Ser Leu Lys
65                  70                  75                  80

Pro Glu Asp Thr Ala Val Tyr Tyr Cys Tyr Leu Lys Lys Trp Arg Asp
            85                  90                  95

Gln Tyr Trp Gly Gln Gly Thr Gln Val Thr Val Ser Ser
            100                 105

<210> SEQ ID NO 148
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Ser Gly Gly Gly Leu Val Gln Ala Gly Gly Ser Leu Arg Leu Ser Cys
1               5                   10                  15

Val Gly Ser Gly Arg Asn Pro Gly Ile Asn Ala Met Gly Trp Tyr Arg
            20                  25                  30

Gln Ala Pro Gly Ser Gln Arg Glu Leu Val Ala Val Trp Gln Thr Gly
            35                  40                  45

Gly Arg Thr Asn Tyr Ala Asp Ser Val Lys Gly Arg Phe Thr Ile Ser
        50                  55                  60

Arg Asp Asn Leu Lys Asn Thr Val Tyr Leu Gln Met Asn Ser Leu Lys
65                  70                  75                  80

Pro Glu Asp Thr Ala Val Tyr Tyr Cys Tyr Leu Lys Lys Trp Arg Asp
            85                  90                  95

Glu Tyr Trp Gly Gln Gly Thr Gln Val Thr Val Ser Ser
            100                 105

<210> SEQ ID NO 149
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Ser Gly Gly Gly Leu Val Gln Ala Gly Gly Ser Leu Arg Leu Ser Cys
1               5                   10                  15

Val Ser Ser Glu Arg Asn Pro Gly Ile Asn Ala Met Gly Trp Tyr Arg
            20                  25                  30

Gln Ala Pro Gly Ser Gln Arg Glu Leu Val Ala Val Trp Gln Thr Gly
            35                  40                  45

Gly Ser Leu Asn Tyr Ala Asp Phe Val Lys Gly Arg Phe Thr Ile Ser
        50                  55                  60

Arg Asp Asn Leu Lys Asn Thr Val Tyr Leu Gln Met Asn Ser Leu Lys
65                  70                  75                  80

Pro Glu Asp Thr Ala Val Tyr Tyr Cys Tyr Leu Lys Lys Trp Arg Asp
            85                  90                  95

Gln Tyr Trp Gly Gln Gly Thr Arg Val Thr Val Ser Ser
            100                 105

<210> SEQ ID NO 150
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Ser Gly Gly Gly Leu Val Gln Ala Gly Gly Ser Leu Arg Leu Ser Cys
1               5                   10                  15

Val Ser Ser Glu Arg Asn Pro Gly Ile Asn Ala Met Gly Trp Tyr Arg
            20                  25                  30

Gln Ala Pro Gly Gly Gln Arg Glu Leu Val Ala Val Trp Gln Thr Gly
        35                  40                  45

Gly Ser Leu Asn Tyr Ala Asp Ser Val Lys Gly Arg Phe Thr Ile Ser
    50                  55                  60

Arg Asp Asn Leu Lys Asn Thr Val Tyr Leu Gln Met Asn Ser Leu Lys
65                  70                  75                  80

Pro Glu Asp Thr Ala Val Tyr Tyr Cys Tyr Leu Lys Lys Trp Arg Asp
                85                  90                  95

Gln Tyr Trp Gly Gln Gly Thr Gln Val Thr Val Ser Ser
            100                 105

<210> SEQ ID NO 151
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Ser Gly Gly Gly Leu Val Gln Ala Gly Gly Ser Leu Arg Leu Ser Cys
1               5                   10                  15

Val Ser Ser Glu Arg Asn Pro Gly Ile Asn Ala Met Gly Trp Tyr Arg
            20                  25                  30

Gln Ala Pro Gly Ser Gln Arg Glu Leu Ala Ala Val Trp Gln Thr Gly
        35                  40                  45

Gly Ser Leu Asn Tyr Ala Asp Ser Val Lys Gly Arg Phe Thr Ile Ser
    50                  55                  60

Arg Asp Asn Leu Lys Asn Thr Val Tyr Leu Gln Met Asn Ser Leu Lys
65                  70                  75                  80

Pro Glu Asp Thr Ala Val Tyr Tyr Cys Tyr Leu Lys Lys Trp Arg Asp
                85                  90                  95

Gln Tyr Trp Gly Gln Gly Thr Gln Val Thr Val Ser Ser
            100                 105

<210> SEQ ID NO 152
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Ser Gly Gly Gly Leu Val Gln Ala Gly Gly Ser Leu Arg Leu Ser Cys
1               5                   10                  15

Val Ser Ser Glu Arg Asn Pro Gly Ile Asn Ala Met Gly Trp Tyr Arg
            20                  25                  30

Gln Ala Pro Gly Ser Gln Arg Glu Leu Val Ala Val Trp Gln Thr Gly
        35                  40                  45

Gly Ser Leu Asn Tyr Ala Asp Ser Val Lys Gly Arg Phe Thr Ile Ser
    50                  55                  60

Arg Asp Asn Leu Lys Asn Thr Val Tyr Leu Gln Met Asn Ser Leu Lys
65                  70                  75                  80

Pro Glu Asp Thr Ala Val Tyr Tyr Cys Tyr Gln Lys Lys Trp Arg Asp
                85                  90                  95

Gln Tyr Trp Gly Gln Gly Thr Gln Val Thr Val Ser Ser
            100                 105

<210> SEQ ID NO 153
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Ser Gly Gly Gly Leu Val Gln Ala Gly Gly Ser Leu Arg Leu Ser Cys
1               5                   10                  15

Val Ser Ser Glu Arg Asn Pro Gly Ile Asn Ala Met Gly Trp Tyr Arg
            20                  25                  30

Gln Ala Pro Gly Ser Gln Arg Glu Leu Val Ala Val Trp Gln Thr Gly
        35                  40                  45

Gly Ser Leu Asn Tyr Ala Asp Ser Val Lys Gly Arg Phe Thr Ile Ser
    50                  55                  60

Arg Asp Asn Leu Lys Asn Thr Val Tyr Leu Gln Met Asn Ser Leu Lys
65                  70                  75                  80

Pro Glu Asp Thr Ala Val Tyr Tyr Cys Tyr Leu Lys Lys Trp Arg Asp
                85                  90                  95

Arg Tyr Trp Gly Gln Gly Thr Gln Val Thr Val Ser Ser
            100                 105

<210> SEQ ID NO 154
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Ser Gly Gly Gly Leu Val Gln Ala Gly Gly Ser Leu Arg Leu Ser Cys
1               5                   10                  15

Val Ser Ser Glu Arg Asn Pro Gly Ile Asn Ala Met Gly Trp Tyr Arg
            20                  25                  30

Gln Ala Pro Gly Ser Gln Arg Glu Leu Val Ala Val Trp Gln Thr Gly
        35                  40                  45

Gly Ser Leu Ser Tyr Ala Asp Ser Val Lys Gly Arg Phe Thr Ile Ser
    50                  55                  60

Arg Asp Asn Leu Lys Asn Thr Val Tyr Leu Gln Met Asn Ser Leu Lys
65                  70                  75                  80

Pro Glu Asp Ala Ala Val Tyr Tyr Cys Tyr Leu Lys Lys Trp Arg Asp
                85                  90                  95

Gln Tyr Trp Gly Gln Gly Thr Arg Val Thr Val Ser Ser
            100                 105

<210> SEQ ID NO 155
<211> LENGTH: 109
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 155

```
Thr Gly Gly Gly Leu Val Gln Ala Gly Gly Ser Leu Arg Leu Ser Cys
1               5                   10                  15

Val Ser Ser Glu Arg Asn Pro Gly Ile Asn Ala Met Gly Trp Tyr Arg
            20                  25                  30

Gln Ala Pro Gly Ser Gln Arg Glu Leu Val Ala Val Trp Gln Thr Gly
        35                  40                  45

Gly Ser Leu Ser Tyr Ala Asp Ser Val Lys Gly Arg Phe Thr Ile Ser
    50                  55                  60

Arg Asp Asn Leu Lys Asn Thr Val Tyr Leu Gln Met Asn Ser Leu Lys
65                  70                  75                  80

Pro Glu Asp Ala Ala Val Tyr Tyr Cys Tyr Leu Lys Lys Trp Arg Asp
                85                  90                  95

Gln Tyr Trp Gly Gln Gly Thr Arg Val Thr Val Ser Ser
            100                 105
```